(12) United States Patent
Zhang et al.

(10) Patent No.: US 10,869,927 B2
(45) Date of Patent: Dec. 22, 2020

(54) HUMAN ENDOTHELIN RECEPTOR ANTIBODY AND USE THEREOF

(71) Applicant: Gmax Biopharm LLC., Hangzhou (CN)

(72) Inventors: Cheng Zhang, Hangzhou (CN); Hua Zhang, Hangzhou (CN); Xiaofeng Wang, Hangzhou (CN); Chenjiang Yao, Hangzhou (CN); Yan Jiang, Hangzhou (CN); Min Wang, Hangzhou (CN); Xinxin Shi, Hangzhou (CN); Hao Pan, Hangzhou (CN); Shuqian Jing, Hangzhou (CN)

(73) Assignee: GMAX BIOPHARM LLC, Hangzhou (CN)

( * ) Notice: Subject to any disclaimer, the term of this patent is extended or adjusted under 35 U.S.C. 154(b) by 0 days.

(21) Appl. No.: 16/538,509

(22) Filed: Aug. 12, 2019

(65) Prior Publication Data

US 2019/0365894 A1  Dec. 5, 2019

Related U.S. Application Data

(63) Continuation of application No. 15/537,190, filed as application No. PCT/CN2016/090960 on Jul. 22, 2016, now Pat. No. 10,376,581.

(30) Foreign Application Priority Data

Dec. 1, 2015 (CN) .......................... 2015 1 0867288

(51) Int. Cl.
| | | |
|---|---|---|
| *A61K 39/395* | (2006.01) | |
| *C07K 16/18* | (2006.01) | |
| *C07K 16/28* | (2006.01) | |
| *C07K 16/26* | (2006.01) | |
| *C12N 5/10* | (2006.01) | |
| *C12N 5/12* | (2006.01) | |
| *C12N 15/63* | (2006.01) | |
| *A61P 9/00* | (2006.01) | |
| *A61P 35/00* | (2006.01) | |
| *A61K 39/00* | (2006.01) | |

(52) U.S. Cl.
CPC ........ *A61K 39/39558* (2013.01); *C07K 16/26* (2013.01); *C07K 16/28* (2013.01); *C12N 5/10* (2013.01); *C12N 5/12* (2013.01); *C12N 15/63* (2013.01); *A61K 2039/505* (2013.01); *A61P 9/00* (2018.01); *A61P 35/00* (2018.01); *C07K 2317/24* (2013.01); *C07K 2317/30* (2013.01); *C07K 2317/565* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,331,647 A | 5/1982 | Goldenberg |
| 4,496,689 A | 1/1985 | Mitra |
| 4,518,584 A | 5/1985 | Mark et al. |
| 4,640,835 A | 2/1987 | Shimizu et al. |
| 4,670,417 A | 6/1987 | Iwasaki et al. |
| 4,737,462 A | 4/1988 | Mark et al. |
| 4,751,180 A | 6/1988 | Cousens et al. |
| 4,791,192 A | 12/1988 | Nakagawa et al. |
| 4,935,233 A | 6/1990 | Bell et al. |
| 4,946,778 A | 8/1990 | Ladner et al. |
| 5,011,912 A | 4/1991 | Hopp et al. |
| 5,457,035 A | 10/1995 | Baum et al. |
| 6,133,426 A | 10/2000 | Gonzalez et al. |
| 6,210,924 B1 | 4/2001 | Hu et al. |
| 6,696,245 B2 | 2/2004 | Winter |
| 6,703,199 B1 | 3/2004 | Koide |
| 6,846,634 B1 | 1/2005 | Tomlinson et al. |
| 2003/0039958 A1 | 2/2003 | Holt et al. |
| 2004/0009507 A1 | 1/2004 | Winter et al. |
| 2004/0038291 A2 | 2/2004 | Tomlinson et al. |
| 2004/0202995 A1 | 10/2004 | Wildt et al. |
| 2005/0202512 A1 | 9/2005 | Tomlinson et al. |
| 2005/0238646 A1 | 10/2005 | Ledbetter et al. |

FOREIGN PATENT DOCUMENTS

| | | |
|---|---|---|
| CN | 103728454 A | 4/2014 |
| CN | 105669863 A | 6/2016 |
| JP | 2010-138165 A | 6/2010 |
| WO | 1993/10151 A1 | 5/1993 |
| WO | 1994/10308 A1 | 5/1994 |
| WO | 2012/045776 A1 | 4/2012 |
| WO | 2017/206840 A1 | 12/2017 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Roque et al., "Antibodies and genetically engineered related molecules: production and purification," Biotechnol. Prog. 20:639-654 (2004).

(Continued)

*Primary Examiner* — Christine J Saoud
*Assistant Examiner* — Jon M Lockard
(74) *Attorney, Agent, or Firm* — Jones Day

(57) ABSTRACT

The present invention discloses an antibody specifically binding to a human endothelin receptor and uses thereof, where the antibody can inhibit the functions of the human endothelin receptor. The present invention includes the preparation, cloning, expression, and characterization of the antibody. The present invention can be used to effectively treat pulmonary arterial hypertension, a disease associated with pulmonary arterial hypertension, and a reproductive organ cancer in a human.

9 Claims, 3 Drawing Sheets

Specification includes a Sequence Listing.

(56) References Cited

OTHER PUBLICATIONS

Schier et al., "Isolation of picomolar affinity anti-c-erbB-2 single-chain Fv by molecular evolution of the complementarity determining regions in the center of the antibody binding site," J. Mol. Biol. 263:551-567 (1996).
Sergre et al., "Receptors for secretin, calcitonin, parathyroid hormone (PTH)/PTH-related peptide, vasoactive intestinal peptide, glucagonlike peptide 1, growth hormone-releasing hormone, and glucagon belong to a newly discovered G-protein-linked receptor family," Trends Endocrinol. Metab. 4:309-314 (1993).
Serasli et al., "Review on bosentan, a dual endothelin receptor antagonist for the treatment of pulmonary arterial hypertension," Recent Pat. Cardiovasc. Drug Discov. 5:184-195 (2010).
Simonneau et al., "Clinical classification of pulmonary hypertension," J. Am. Coll. Cardiol. 43:5S-12S (2004).
Sippl et al., "Threading thrills and threats," Structure 4:15-19 (1996).
Thompson et al., "Affinity maturation of a high-affinity human monoclonal antibody against the third hypervariable loop of human immunodeficiency virus: use of phage display to improve affinity and broaden strain reactivity," J. Mol. Biol. 256:77-88 (1996).
Thornton et al., "Protein structure. Prediction of progress at last," Nature 354:105-106 (1991).
Urlaub et al., "Isolation of Chinese hamster cell mutants deficient in dihydrofolate reductase activity," Proc. Natl. Acad. Sci. U.S.A. 77:4216-4220 (1980).
Vaughan et al., "Human antibodies by design," Nat. Biotechnol. 16:535-539 (1998).
Veber et al., "The design of metabolically-stable peptide analogs," Trends Neurosci. 8:392-396 (1985).
Voss et al., "The role of enhancers in the regulation of cell-type-specific transcriptional control," Trends Biochem. Sci. 11:287-289 (1986).
Walder et al., "Oligodeoxynucleotide-directed mutagenesis using the yeast transformation system," Gene 42:133-139 (1986).
Ward et al., "Binding activities of a repertoire of single immunoglobulin variable domains secreted from *Escherichia coli*," Nature 341:544-546 (1989).
Yang et al., "CDR walking mutagenesis for the affinity maturation of a potent human anti-HIV-1 antibody into the picomolar range," J. Mol. Biol. 254:392-403 (1995).
Marks et al., "By-passing immunization: building high affinity human antibodies by chain shuffling," Biotechnology (N.Y.) 10:779-783 (1992).
Gribskov et al., "Profile analysis," Methods Enzymol. 183:146-159 (1990).
Rost et al., "Profile analysis," Methods Enzymol. 183:146-159 (1990).
Galie et al., "The endothelin system in pulmonary arterial hypertension," Cardiovasc. Res. 61:227-237 (2004).
Wendel et al., "Distribution of endothelin receptor subtypes ETA and ETB in the rat kidney.," J. Histochem. Cytochem. 54:1193-1203 (2006).
Ashkenazi et al., "Protection against endotoxic shock by a tumor necrosis factor receptor immunoadhesin," Proc. Natl. Acd. Sci. U.S.A. 88:10535-10539 (1991).
Baron et al., "Co-regulation of two gene activities by tetracycline via a bidirectional promoter," Nucleic Acids Res. 23:3605-3606 (1995).
Barst et al., "Diagnosis and differential assessment of pulmonary arterial hypertension," J. Am. Coll. Cardiol. 13:40S-47S (2004).
Barton et al., "Endothelin: 20 years from discovery to therapy," Can. J. Physiol. Pharmacol. 86:485-498 (2008).
Bauer et al., "A genetic enrichment for mutations constructed by oligodeoxynucleotide-directed mutagenesis," Gene 37:73-81 (1985).
Baum et al., "Molecular characterization of murine and human OX40/OX40 ligand systems: identification of a human OX40 ligand as the HTLV-1-regulated protein gp34," EMBO J. 13:3992-4001 (1994).

Bird et al., "Single-chain antigen-binding proteins," Science 242:423-426 (1988).
Bowie et al., "A method to identify protein sequences that fold into a known three-dimensional structure," Science 253:164-170 (1991).
Brenner et al., "Population statistics of protein structures: lessons from structural classifications," Curr. Op. Struct. Biol. 7:369-376 (1997).
Byrn et al., "Biological properties of a CD4 immunoadhesin," Nature 344:667-670 (1990).
Chou et al., "Conformational parameters for amino acids in helical, beta-sheet, and random coil regions calculated from proteins," Biochemistry 13:211-222 (1974).
Chou et al., "Prediction of protein conformation," Biochemistry 13:222-245 (1974).
Chou et al., "Prediction of the secondary structure of proteins from their amino acid sequence," Adv. Enzymol. Relat. Areas Mol. Biol. 47:45-148 (1978).
Chou et al., "Empirical predictions of protein conformation," Ann. Rev. Biochem. 47:251-276 (1978).
Chou et al., "Prediction of beta-turns," Biophys. J. 26:367-383 (1979).
Craik, "Use of oligonucleotides for site-specific mutagenesis," BioTechniques 3:12-19 (1985).
Crameri et al., "DNA shuffling of a family of genes from diverse species accelerates directed evolution," Nature, 391:288-291 (1998).
De Graaf et al., "Expression of scFvs and scFv fusion proteins in eukaryotic cells," Methods Mol. Biol. 178:379-387 (2002).
Evans et al., "Design of nonpeptidal ligands for a peptide receptor: cholecystokinin antagonists," J. Med. Chem. 30:1229-1239 (1987).
Fanslow et al., "Structural characteristics of CD40 ligand that determine biological function," Semin. Immunol. 6:267-278 (1994).
Gluzman et al., "SV40-transformed simian cells support the replication of early SV40 mutants," Cell 23:175-182 (1981).
Gribskov et al., "Profile analysis: detection of distantly related proteins," Proc. Natl. Acad. Sci. U.S.A. 84:4355-4358 (1987).
Harris, "Processing of C-terminal lysine and arginine residues of proteins isolated from mammalian cell culture," J. Chromatogr. A. 705:129-134 (1995).
Holliger et al., "'Diabodies': small bivalent and bispecific antibody fragments," Proc. Natl. Acad. Sci. U.S.A. 90:6444-6448 (1993).
Holliger et al., "Engineered antibody fragments and the rise of single domains," Nat. Biotechnology, 23:1126-1136 (2005).
Holm et al., "Protein folds and families: sequence and structure alignments," Nucleic Acids Res. 27:244-247 (1999).
Hopp et al., "A short polypeptide marker sequence useful for recombinant protein identification and purification," Bio/Technology 6:1204-1210 (1988).
Hoppe et al., "A parallel three stranded alpha-helical bundle at the nucleation site of collagen triple-helix formation," FEBS Lett. 344:191-195 (1994).
Huston et al, "Protein engineering of antibody binding sites: recovery of specific activity in an anti-digoxin single-chain Fv analogue produced in *Escherichia coli*," Proc. Natl. Acad. Sci. U.S.A. 85:5879-5883 (1988).
Jelinek et al., "Expression cloning and signaling properties of the rat glucagon receptor," Science 259:1614-1616 (1993).
Jones, "Progress in protein structure prediction," Curr. Opin. Struct. Biol. 7:377-387 (1997).
Korndorfer et al., "Crystallographic analysis of an 'anticalin' with tailored specificity for fluorescein reveals high structural plasticity of the lipocalin loop region," Proteins 53:121-129 (2003).
Kortt et al., "Single-chain Fv fragments of anti-neuraminidase antibody NC10 containing five- and ten-residue linkers form dimers and with zero-residue linker a trimer," Protein Eng. 10:423-433 (1997).
Kortt et al., "Dimeric and trimeric antibodies: high avidity scFvs for cancer targeting," Biomol. Eng. 18:95-108 (2001).
Kriangkum et al., "Bispecific and bifunctional single chain recombinant antibodies," Biomol. Eng. 18:31-40 (2001).
Landschulz et al., "The leucine zipper: a hypothetical structure common to a new class of DNA binding proteins," Science 240:1759-1764 (1988).

(56) References Cited

OTHER PUBLICATIONS

Lanitto et al., "Chain shuffling to modify properties of recombinant immunoglobulins," Methods Mol. Biol. 178:303-316 (2002).

Lunde et al., "Troybodies and pepbodies," Biochem. Soc. Trans. 30:500-506 (2002).

Maniatis et al., "Regulation of inducible and tissue-specific gene expression," Science 236:1237-1245 (1987).

McMahan et al., "A novel IL-1 receptor, cloned from B cells by mammalian expression, is expressed in many cell types," EMBO J. 10:2821-2832 (1991).

Moult et al., "The current state of the art in protein structure prediction," Curr. Op. Biotech. 7:422-427 (1996).

Nelson et al., "The endothelin axis: emerging role in cancer," Nat. Rev. Cancer 3:110-113 (2003).

Neylon, "Vascular biology of endothelin signal transduction," Clin. Exp. Pharmacol. Physiol. 26:149-153 (1999).

Nisonoff et al., "Separation of univalent fragments from the bivalent rabbit antibody molecule by reduction of disulfide bonds," Arch. Biochem. Biophys. 89:230-244 (1960).

Nygren et al., "Scaffolds for engineering novel binding sites in proteins," Curr. Opin. Struct. Biol. 7:463-469 (1997).

Patten et al., "Applications of DNA shuffling to pharmaceuticals and vaccines," Curr. Opin. Biotechnol., 8:724-733 (1997).

Poljak, "Production and structure of diabodies," Structure 2:1121-1123 (1994).

Porter, "The hydrolysis of rabbit y-globulin and antibodies with crystalline papain," Biochem. J. 73:119-126 (1959).

Rasmussen et al., "Isolation, characterization and recombinant protein expression in Veggie-CHO: A serum-free CHO host cell line," Cytotechnology 28:31-42 (1998).

Rizo et al., "Constrained peptides: models of bioactive peptides and protein substructures," Ann. Rev. Biochem. 61:387-418 (1992).

* cited by examiner

Figure 1

| CLONE(#) | CHO-ET$_A$R | CHO-DHFR | CLONE(#) | CHO-ET$_A$R | CHO-DHFR | CLONE(#) | CHO-ET$_A$R | CHO-DHFR |
|---|---|---|---|---|---|---|---|---|
| 1B4 | 0.31 | 0.19 | 11D11 | 0.19 | 0.08 | 25B5 | 0.14 | 0.06 |
| 1B7 | 0.29 | 0.07 | 11H12 | 0.26 | 0.09 | 25G8 | 0.37 | 0.06 |
| 1G8 | 0.15 | 0.07 | 12B1 | 0.28 | 0.06 | 25F9 | 0.14 | 0.06 |
| 1G12 | 0.19 | 0.07 | 12F1 | 0.16 | 0.06 | 25B10 | 0.14 | 0.06 |
| 2F5 | 0.28 | 0.11 | 13B9 | 0.17 | 0.07 | 25C11 | 0.77 | 0.07 |
| 2F12 | 0.41 | 0.26 | 13A12 | 0.34 | 0.07 | 25H10 | 0.39 | 0.06 |
| 3A1 | 0.19 | 0.07 | 14G6 | 0.77 | 0.07 | 26 E4 | 0.13 | 0.07 |
| 3 E3 | 0.16 | 0.07 | 14F8 | 0.16 | 0.07 | 27B3 | 0.16 | 0.07 |
| 3F3 | 0.16 | 0.07 | 14A9 | 0.34 | 0.18 | 27D8 | 0.35 | 0.17 |
| 3B7 | 0.16 | 0.09 | 14B9 | 0.37 | 0.06 | 27F12 | 0.18 | 0.08 |
| 3G12 | 0.19 | 0.06 | 14F9 | 0.90 | 0.09 | 28C9 | 0.22 | 0.10 |
| 4B2 | 0.35 | 0.14 | 14 E10 | 0.30 | 0.06 | 30F3 | 0.20 | 0.10 |
| 4C7 | 0.17 | 0.07 | 15F3 | 1.26 | 0.06 | 30A5 | 0.23 | 0.11 |
| 5H1 | 0.14 | 0.07 | 15D7 | 0.16 | 0.06 | 30C11 | 0.14 | 0.07 |
| 5H3 | 0.14 | 0.07 | 15D10 | 0.18 | 0.06 | 30D11 | 0.14 | 0.06 |
| 5C12 | 0.14 | 0.07 | 15G11 | 0.15 | 0.06 | 30H12 | 0.78 | 0.41 |
| 6A1 | 0.21 | 0.07 | 16H4 | 1.07 | 0.07 | 32B7 | 0.84 | 0.50 |
| 6D2 | 0.58 | 0.22 | 18F1 | 0.94 | 0.07 | 32G12 | 0.99 | 0.15 |
| 6D5 | 0.24 | 0.08 | 18F3 | 0.30 | 0.07 | 33F1 | 0.37 | 0.06 |
| 6B6 | 0.49 | 0.25 | 19G12 | 0.48 | 0.07 | 33D6 | 0.39 | 0.08 |
| 6 E8 | 1.76 | 0.41 | 20H1 | 0.30 | 0.06 | 35G3 | 0.53 | 0.07 |
| 8 E2 | 1.33 | 0.06 | 21A1 | 0.91 | 0.07 | 35B8 | 0.61 | 0.07 |
| 8B9 | 0.36 | 0.07 | 21F7 | 0.15 | 0.06 | 36 E9 | 0.29 | 0.05 |
| 8B10 | 0.39 | 0.22 | 21G12 | 0.14 | 0.06 | 36 E11 | 0.34 | 0.06 |
| 8C11 | 0.76 | 0.08 | 22A1 | 0.14 | 0.06 | 36F12 | 1.15 | 0.06 |
| 9D2 | 0.16 | 0.07 | 22C5 | 0.34 | 0.17 | 37B12 | 0.89 | 0.08 |
| 10A2 | 0.16 | 0.07 | 23G1 | 0.15 | 0.06 | 38A5 | 1.75 | 0.08 |
| 10C6 | 0.29 | 0.07 | 23D5 | 0.26 | 0.13 | 38F5 | 1.18 | 0.07 |
| 10B7 | 0.28 | 0.07 | 23 E6 | 1.13 | 0.07 | 40F1 | 0.70 | 0.07 |
| 10A9 | 0.14 | 0.07 | 24C8 | 0.17 | 0.09 | 40F3 | 0.47 | 0.05 |
| 11D1 | 0.25 | 0.07 | 24H10 | 0.17 | 0.06 | 40G2 | 2.22 | 0.08 |
| 11H3 | 0.16 | 0.06 | 24F11 | 0.14 | 0.06 | 40H11 | 0.22 | 0.06 |

SEQUENCE LISTING

```
<160> NUMBER OF SEQ ID NOS: 204

<210> SEQ ID NO 1
<211> LENGTH: 1868
<212> TYPE: DNA
<213> ORGANISM: Homo sapiens

<400> SEQUENCE: 1
gaattcggga aaaagtgaag gtgtaaaagc agcacaagtg caataagaga tatttcctca      60
aatttgcctc aagatggaaa ccctttgcct cagggcatcc ttttggctgg cactggttgg     120
atgtgtaatc agtgataatc ctgagagata cagcacaaat ctaagcaatc atgtggatga     180
tttcaccact tttcgtggca cagagctcag cttcctggtt accactcatc aacccactaa     240
tttggtccta cccagcaatg gctcaatgca caactattgc ccacagcaga ctaaaattac     300
ttcagctttc aaatacatta acactgtgat atcttgtact attttcatcg tgggaatggt     360
ggggaatgca actctgctca ggatcattta ccagaacaaa tgtatgagga atggccccaa     420
cgcgctgata gccagtcttg cccttggaga ccttatctat gtggtcattg atctccctat     480
caatgtattt aagctgctgg ctgggcgctg gcctttcgat cacaatgact ttggcgtatt     540
tctttgcaag ctgttcccct ttttgcagaa gtcctcggtg gggatcaccg tcctcaacct     600
```

-continued

```
ctgcgctctt agtgttgaca ggtacagagc agttgcctcc tggagtcgtg ttcagggaat    660
tgggattcct ttggtaactg ccattgaaat tgtctccatc tggatcctgt cctttatcct    720
ggccattcct gaagcgattg gcttcgtcat ggtacccttt gaatataggg gtgaacagca    780
taaaacctgt atgctcaatg ccacatcaaa attcatggag ttctaccaag atgtaaagga    840
ctggtggctc ttcgggttct atttctgtat gcccttggtg tgcactgcga tcttctacac    900
cctcatgact tgtgagatgt tgaacagaag gaatggcagc ttgagaattg ccctcagtga    960
acatcttaag cagcgtcgag aagtggcaaa acagttttc tgcttggttg taattttgc    1020
tctttgctgg ttccctcttc atttaagccg tatattgaag aaaactgtgt ataacgagat    1080
ggacaagaac cgatgtgaat tacttagttt cttactgctc atggattaca tcggtattaa    1140
cttggcaacc atgaattcat gtataaaccc catagctctg tattttgtga gcaagaaatt    1200
taaaaattgt ttccagtcat gcctctgctg ctgctgttac cagtccaaaa gtctgatgac    1260
ctcggtcccc atgaacggaa caagcatcca gtggaagaac cacgatcaaa acaaccacaa    1320
cacagaccgg agcagccata aggacagcat gaactgacca cccttagaag cactcctcgg    1380
tactcccata atcctctcgg agaaaaaaat cacaaggcaa ctgtgagtcc gggaatctct    1440
tctctgatcc ttcttcctta attcactccc acacccaaga gaaatgctt tccaaaaccg    1500
caagggtaga ctggtttatc cacccacaac atctacgaat cgtacttctt taattgatct    1560
aatttacata ttctgcgtgt tgtattcagc actaaaaaat ggtgggagct gggggagaat    1620
gaagactgtt aaatgaaacc agaaggatat ttactacttt tgcatgaaaa tagagctttc    1680
aagtacatgg ctagctttta tggcagttct ggtgaatgtt caatgggaac tggtcaccat    1740
gaaactttag agattaacga caagattttc tactttttt aagtgatttt tttgtccttc    1800
agccaaacac aatatgggct caagtcactt ttatttgaaa tgtcatttgg tgccagtatc    1860
ccgaattc                                                             1868
```

<210> SEQ ID NO 2
<211> LENGTH: 427
<212> TYPE: PRT
<213> ORGANISM: Homo sapiens

<400> SEQUENCE: 2

```
Met Glu Thr Leu Cys Leu Arg Ala Ser Phe Trp Leu Ala Leu Val Gly
  1               5                  10                  15

Cys Val Ile Ser Asp Asn Pro Glu Arg Tyr Ser Thr Asn Leu Ser Asn
             20                  25                  30

His Val Asp Asp Phe Thr Thr Phe Arg Gly Thr Glu Leu Ser Phe Leu
         35                  40                  45

Val Thr Thr His Gln Pro Thr Asn Leu Val Leu Pro Ser Asn Gly Ser
     50                  55                  60

Met His Asn Tyr Cys Pro Gln Gln Thr Lys Ile Thr Ser Ala Phe Lys
 65                  70                  75                  80

Tyr Ile Asn Thr Val Ile Ser Cys Thr Ile Phe Ile Val Gly Met Val
                 85                  90                  95

Gly Asn Ala Thr Leu Leu Arg Ile Ile Tyr Gln Asn Lys Cys Met Arg
            100                 105                 110

Asn Gly Pro Asn Ala Leu Ile Ala Ser Leu Ala Leu Gly Asp Leu Ile
        115                 120                 125

Tyr Val Val Ile Asp Leu Pro Ile Asn Val Phe Lys Leu Leu Ala Gly
    130                 135                 140
```

Arg Trp Pro Phe Asp His Asn Asp Phe Gly Val Phe Leu Cys Lys Leu
145                 150                 155                 160

Phe Pro Phe Leu Gln Lys Ser Ser Val Gly Ile Thr Val Leu Asn Leu
                165                 170                 175

Cys Ala Leu Ser Val Asp Arg Tyr Arg Ala Val Ala Ser Trp Ser Arg
            180                 185                 190

Val Gln Gly Ile Gly Ile Pro Leu Val Thr Ala Ile Glu Ile Val Ser
        195                 200                 205

Ile Trp Ile Leu Ser Phe Ile Leu Ala Ile Pro Glu Ala Ile Gly Phe
    210                 215                 220

Val Met Val Pro Phe Glu Tyr Arg Gly Glu Gln His Lys Thr Cys Met
225                 230                 235                 240

Leu Asn Ala Thr Ser Lys Phe Met Glu Phe Tyr Gln Asp Val Lys Asp
                245                 250                 255

Trp Trp Leu Phe Gly Phe Tyr Phe Cys Met Pro Leu Val Cys Thr Ala
            260                 265                 270

Ile Phe Tyr Thr Leu Met Thr Cys Glu Met Leu Asn Arg Arg Asn Gly
        275                 280                 285

Ser Leu Arg Ile Ala Leu Ser Glu His Leu Lys Gln Arg Arg Glu Val
    290                 295                 300

Ala Lys Thr Val Phe Cys Leu Val Val Ile Phe Ala Leu Cys Trp Phe
305                 310                 315                 320

Pro Leu His Leu Ser Arg Ile Leu Lys Lys Thr Val Tyr Asn Glu Met
                325                 330                 335

Asp Lys Asn Arg Cys Glu Leu Leu Ser Phe Leu Leu Leu Met Asp Tyr
            340                 345                 350

Ile Gly Ile Asn Leu Ala Thr Met Asn Ser Cys Ile Asn Pro Ile Ala
        355                 360                 365

Leu Tyr Phe Val Ser Lys Lys Phe Lys Asn Cys Phe Gln Ser Cys Leu
    370                 375                 380

Cys Cys Cys Cys Tyr Gln Ser Lys Ser Leu Met Thr Ser Val Pro Met
385                 390                 395                 400

Asn Gly Thr Ser Ile Gln Trp Lys Asn His Asp Gln Asn Asn His Asn
                405                 410                 415

Thr Asp Arg Ser Ser His Lys Asp Ser Met Asn
            420                 425

<210> SEQ ID NO 3
<211> LENGTH: 2696
<212> TYPE: DNA
<213> ORGANISM: Mouse

<400> SEQUENCE: 3
gtctaggagc ctgtggagtc taaggaagat cgcgggaggc gtgttcctcc ggagtttgct    60
tttccttggg agcctcgcgc gcacacccat cccttctagt ctggcaactg tgtctaggag   120
gtggggagcc tctctctgat ccaccggacc atcgctggag cttgcaggct gagcaagatc   180 tcccctaga gaagcctggc tgtccgggga agtttccccg agctgagact gtgctgcagc   240
cctggtcacc cgccaccctg cgcgccaccc tcgttctcca gctcaggctc cggctggccc   300
gtgcgcggac ctggagctgt ctgcttccga ggagctctaa ggtgaaaaaa agaaaggcgt   360
gagaccaaca taagaagact taaaatccag gttaagatga gtatcttttg ccttgcggca   420 tactttggc tgaccatggt gggaggcgta atggctgaca atccggagag atacagcgct   480

| | |
|---|---|
| aatctaagca gccacatgga agacttcacc ccttttccgg ggacggagat caactttctg | 540 |
| ggcaccaccc atcgacccc taatttggcc ctgcctagca atggctcaat gcacggctat | 600 |
| tgcccacagc agactaaaat cacgacagct ttcaaatata ttaacactgt gatatcctgc | 660 |
| accattttca tcgtgggaat ggtggggaac gcaactctac tacgaatcat ttaccaaaac | 720 |
| aagtgtatga ggaacggccc caatgcgctc atagccagcc tggcccttgg agaccttatc | 780 |
| tacgtggtca ttgacctccc catcaacgtg tttaagctct tggcaggacg ctggcctttc | 840 |
| gaccacaatg attttggagt gtttctctgc aagctgttcc ccttcctgca gaagtcctcc | 900 |
| gtgggcatca ccgtcttgaa cctctgtgct ctcagtgtgg acaggtacag agcagtggct | 960 |
| tcctggagcc gagttcaagg aatcgggatc cccttgatta ccgccattga aatcgtctcc | 1020 |
| atctggattc tttccttcat cttggccatc ccggaagcaa tcggcttcgt catggtaccc | 1080 |
| ttcgaataca agggcgagct gcataggacc tgcatgctca acgccacgtc caagttcatg | 1140 |
| gagttttacc aagatgtgaa ggactggtgg ctctttgggt tctacttctg catgcccttg | 1200 |
| gtgtgcacag caatcttcta caccctcatg acctgtgaga tgctcaacag gaggaacggc | 1260 |
| agcttgcgga tcgcccttag tgagcacctc aaacagcgtc gagaagtggc aaagactgtc | 1320 |
| ttctgcttgg ttgtcatctt cgccctgtgc tggttccctc ttcacttaag ccgcattttg | 1380 |
| aagaaaactg tatatgatga gatggataag aaccggtgtg aactgctcag cttcttgctg | 1440 |
| ctaatggatt acatcggcat taacctggca accatgaatt cttgcataaa cccaatagct | 1500 |
| ctatattttg tgagcaagaa attcaaaaat tgttttcagt cctgcctctg ttgctgttgt | 1560 |
| caccagtcca aaagcctcat gacctcggtc cccatgaatg gaacgagtat ccagtggaag | 1620 |
| aaccaagagc agaacaacca caacacggaa cggagcagcc acaaggacag catgaactaa | 1680 |
| ccctccgcag aaacaccgag acgtgtgcct tcaagtccta ggatggaaac aaccattacg | 1740 |
| ccacagatgc gctcccaaaa cctcccaagt ctctcccatg ctccttttct aagtccatcc | 1800 |
| taggaaaagc tctcctgccc tcccaacagc acgtggtgga ccggtcccag ctatagccaa | 1860 |
| tgggtctttc ctgagtactg tatatgattt gcataccgcg catgtcattt ccaacacttg | 1920 |
| aaaattagag ctgggagaaa ggagatgatg gttcaaagaa gccacctagc tgccgccttt | 1980 |
| gcatgaacac agagtttgca agttcatgac cagcttccgt gcagttctat ggaccagctg | 2040 |
| gtgggaactg tccatcctaa gattctagag cagtgggtct caaccttccc aatgctgcag | 2100 |
| ccccttaata cagttcttca ttttccagtg accccccca accacaatat tatttttgt | 2160 |
| tgctacttca attattttga attgttataa ttgtctgata tttctgatag tcttagcctg | 2220 |
| ccctgttaa agggtcatta gcaacccaca agttgagaac cactgcccta gaaattctgt | 2280 |
| tgcgtttcat ggcccatgac tacaatccta aaattggaga ggtgagggaa gatggtcagg | 2340 |
| tgttcaaggt tagcctcatc aacatagttc ggaaaagcca gggctacctg ttctcacaag | 2400 |
| acacaaacag acaaaaagtg tttcaaagtt atggcagatt cattattatt aattattatt | 2460 |
| atcttatagc caaacacatt gtgaggttaa agtactcttt tggaaatgtc accgagtgtt | 2520 |
| ggtactttat aactgcatgg taccctagaa atgatcgttt catcttcttt caatgtactc | 2580 |
| tgaagaaaag aaataggaga gttccagaag ggagatctgg aaaggagata atgtttgaaa | 2640 |
| tgtaaagaag gaaaatatcc aataaaaaaa ttcaaagtct aaaaaaaaaa aaaaaa | 2696 |

<210> SEQ ID NO 4
<211> LENGTH: 427
<212> TYPE: PRT
<213> ORGANISM: Mouse

```
<400> SEQUENCE: 4

Met Ser Ile Phe Cys Leu Ala Ala Tyr Phe Trp Leu Thr Met Val Gly
1               5                   10                  15

Gly Val Met Ala Asp Asn Pro Glu Arg Tyr Ser Ala Asn Leu Ser Ser
            20                  25                  30

His Met Glu Asp Phe Thr Pro Phe Pro Gly Thr Glu Ile Asn Phe Leu
        35                  40                  45

Gly Thr Thr His Arg Pro Pro Asn Leu Ala Leu Pro Ser Asn Gly Ser
    50                  55                  60

Met His Gly Tyr Cys Pro Gln Gln Thr Lys Ile Thr Thr Ala Phe Lys
65                  70                  75                  80

Tyr Ile Asn Thr Val Ile Ser Cys Thr Ile Phe Ile Val Gly Met Val
                85                  90                  95

Gly Asn Ala Thr Leu Leu Arg Ile Ile Tyr Gln Asn Lys Cys Met Arg
            100                 105                 110

Asn Gly Pro Asn Ala Leu Ile Ala Ser Leu Ala Leu Gly Asp Leu Ile
        115                 120                 125

Tyr Val Val Ile Asp Leu Pro Ile Asn Val Phe Lys Leu Leu Ala Gly
    130                 135                 140

Arg Trp Pro Phe Asp His Asn Asp Phe Gly Val Phe Leu Cys Lys Leu
145                 150                 155                 160

Phe Pro Phe Leu Gln Lys Ser Ser Val Gly Ile Thr Val Leu Asn Leu
                165                 170                 175

Cys Ala Leu Ser Val Asp Arg Tyr Arg Ala Val Ala Ser Trp Ser Arg
            180                 185                 190

Val Gln Gly Ile Gly Ile Pro Leu Ile Thr Ala Ile Glu Ile Val Ser
        195                 200                 205

Ile Trp Ile Leu Ser Phe Ile Leu Ala Ile Pro Glu Ala Ile Gly Phe
    210                 215                 220

Val Met Val Pro Phe Glu Tyr Lys Gly Glu Leu His Arg Thr Cys Met
225                 230                 235                 240

Leu Asn Ala Thr Ser Lys Phe Met Glu Phe Tyr Gln Asp Val Lys Asp
                245                 250                 255

Trp Trp Leu Phe Gly Phe Tyr Phe Cys Met Pro Leu Val Cys Thr Ala
            260                 265                 270

Ile Phe Tyr Thr Leu Met Thr Cys Glu Met Leu Asn Arg Arg Asn Gly
        275                 280                 285

Ser Leu Arg Ile Ala Leu Ser Glu His Leu Lys Gln Arg Arg Glu Val
    290                 295                 300

Ala Lys Thr Val Phe Cys Leu Val Val Ile Phe Ala Leu Cys Trp Phe
305                 310                 315                 320

Pro Leu His Leu Ser Arg Ile Leu Lys Lys Thr Val Tyr Asp Glu Met
                325                 330                 335

Asp Lys Asn Arg Cys Glu Leu Leu Ser Phe Leu Leu Leu Met Asp Tyr
            340                 345                 350

Ile Gly Ile Asn Leu Ala Thr Met Asn Ser Cys Ile Asn Pro Ile Ala
        355                 360                 365

Leu Tyr Phe Val Ser Lys Lys Phe Lys Asn Cys Phe Gln Ser Cys Leu
    370                 375                 380

Cys Cys Cys Cys His Gln Ser Lys Ser Leu Met Thr Ser Val Pro Met
385                 390                 395                 400

Asn Gly Thr Ser Ile Gln Trp Lys Asn Gln Glu Gln Asn Asn His Asn
```

```
                    405                 410                 415
Thr Glu Arg Ser Ser His Lys Asp Ser Met Asn
                420                 425

<210> SEQ ID NO 5
<211> LENGTH: 1436
<212> TYPE: DNA
<213> ORGANISM: Rattus

<400> SEQUENCE: 5
gtgagaccaa cataacagga cgtttcttca gatccacatt aagatgggtg tcctttgctt      60
tctggcgtcc ttttggctgg ccctggtggg aggcgcaatc gctgacaatg ctgagagata     120
cagtgctaat ctaagcagcc acgtggagga cttcaccct tttccaggga cagagttcga     180
cttttctggg c accaccttc gaccccctaa tttggccctg cctagcaatg gctcaatgca     240
tggctattgc ccacagcaga caaaaatcac gacggctttc aaatatatca acactgtgat     300
atcctgtacc attttcatcg tgggaatggt ggggaacgcc actctcctaa gaatcattta     360
ccaaaacaag tgtatgagga acggccccaa tgcgctcata gccagcctgg cccttggaga     420
ccttatctac gtggtcattg atctccccat caatgtgttt aagctgttgg cggggcgctg     480
gccttttgac cacaatgatt ttggagtgtt tctctgcaag ctgttcccct ttttgcagaa     540
gtcgtccgtg ggcatcactg tcctgaatct ctgcgctctc agtgtggaca ggtacagagc     600
agtggcttcc tggagccggg ttcaaggaat cgggatcccc ttgattaccg ccattgaaat     660
tgtctccatc tggatccttt cctttatctt ggccatccca gaagcaatcg gcttcgtcat     720
ggtacccttc gaatacaagg gcgagcagca caggacctgc atgctcaacg ccacgaccaa     780
gttcatggag ttttaccaag acgtgaagga ctggtggctc tttggattct acttctgcat     840
gcccttggtg tgcacagcaa tcttctatac cctcatgacc tgtgagatgc tcaacagaag     900
gaatgggagc ttgcggattg ccctcagcga cacctcaag cagcgtcgag aggtggcaaa     960
gaccgtcttc tgcttggttg tcatcttcgc cctgtgctgg ttccctcttc acttaagccg    1020
aattttgaag aaaaccgtct atgatgagat ggataagaac cggtgtgaac tgctcagctt    1080
cttgctgctc atggattaca ttggcattaa cctggcaacc atgaactctt gcataaaccc    1140
aatagctctg tattttgtga gcaagaaatt caaaaattgt tttcagtcat gcctctgttg    1200
ctgttgtcac cagtccaaaa gcctcatgac ctcggtcccc atgaatggaa cgagtatcca    1260
gtggaagaac caggagcaga accacaacac agaacggagc agccacaagg acagcatgaa    1320
ctaaccctgt gcagaagcac cgagcagtgt gccttcgagt cccaggatga acggtcacg     1380
cagcagctgc gctcccaaaa cctcccaggt ctctcccctg cttttgtct aagctt         1436

<210> SEQ ID NO 6
<211> LENGTH: 426
<212> TYPE: PRT
<213> ORGANISM: Rattus

<400> SEQUENCE: 6

Met Gly Val Leu Cys Phe Leu Ala Ser Phe Trp Leu Ala Leu Val Gly
1               5                   10                  15

Gly Ala Ile Ala Asp Asn Ala Glu Arg Tyr Ser Ala Asn Leu Ser Ser
                20                  25                  30

His Val Glu Asp Phe Thr Pro Phe Pro Gly Thr Glu Phe Asp Phe Leu
            35                  40                  45

Gly Thr Thr Leu Arg Pro Pro Asn Leu Ala Leu Pro Ser Asn Gly Ser
```

```
            50                  55                  60
Met His Gly Tyr Cys Pro Gln Gln Thr Lys Ile Thr Ala Phe Lys
 65                  70                  75                  80

Tyr Ile Asn Thr Val Ile Ser Cys Thr Ile Phe Ile Val Gly Met Val
                     85                  90                  95

Gly Asn Ala Thr Leu Leu Arg Ile Ile Tyr Gln Asn Lys Cys Met Arg
                    100                 105                 110

Asn Gly Pro Asn Ala Leu Ile Ala Ser Leu Ala Leu Gly Asp Leu Ile
                115                 120                 125

Tyr Val Val Ile Asp Leu Pro Ile Asn Val Phe Lys Leu Leu Ala Gly
                130                 135                 140

Arg Trp Pro Phe Asp His Asn Asp Phe Gly Val Phe Leu Cys Lys Leu
145                 150                 155                 160

Phe Pro Phe Leu Gln Lys Ser Ser Val Gly Ile Thr Val Leu Asn Leu
                165                 170                 175

Cys Ala Leu Ser Val Asp Arg Tyr Arg Ala Val Ala Ser Trp Ser Arg
                180                 185                 190

Val Gln Gly Ile Gly Ile Pro Leu Ile Thr Ala Ile Glu Ile Val Ser
                195                 200                 205

Ile Trp Ile Leu Ser Phe Ile Leu Ala Ile Pro Glu Ala Ile Gly Phe
                210                 215                 220

Val Met Val Pro Phe Glu Tyr Lys Gly Glu Gln His Arg Thr Cys Met
225                 230                 235                 240

Leu Asn Ala Thr Thr Lys Phe Met Glu Phe Tyr Gln Asp Val Lys Asp
                245                 250                 255

Trp Trp Leu Phe Gly Phe Tyr Phe Cys Met Pro Leu Val Cys Thr Ala
                260                 265                 270

Ile Phe Tyr Thr Leu Met Thr Cys Glu Met Leu Asn Arg Arg Asn Gly
                275                 280                 285

Ser Leu Arg Ile Ala Leu Ser Glu His Leu Lys Gln Arg Arg Glu Val
                290                 295                 300

Ala Lys Thr Val Phe Cys Leu Val Val Ile Phe Ala Leu Cys Trp Phe
305                 310                 315                 320

Pro Leu His Leu Ser Arg Ile Leu Lys Lys Thr Val Tyr Asp Glu Met
                325                 330                 335

Asp Lys Asn Arg Cys Glu Leu Leu Ser Phe Leu Leu Leu Met Asp Tyr
                340                 345                 350

Ile Gly Ile Asn Leu Ala Thr Met Asn Ser Cys Ile Asn Pro Ile Ala
                355                 360                 365

Leu Tyr Phe Val Ser Lys Lys Phe Lys Asn Cys Phe Gln Ser Cys Leu
                370                 375                 380

Cys Cys Cys Cys His Gln Ser Lys Ser Leu Met Thr Ser Val Pro Met
385                 390                 395                 400

Asn Gly Thr Ser Ile Gln Trp Lys Asn Gln Glu Gln Asn His Asn Thr
                405                 410                 415

Glu Arg Ser Ser His Lys Asp Ser Met Asn
                420                 425

<210> SEQ ID NO 7
<211> LENGTH: 33
<212> TYPE: DNA
<213> ORGANISM: Mouse

<400> SEQUENCE: 7
```
agggccagtc agaacattgg cacaagcata cac                          33

<210> SEQ ID NO 8
<211> LENGTH: 11
<212> TYPE: PRT
<213> ORGANISM: Mouse

<400> SEQUENCE: 8

Arg Ala Ser Gln Asn Ile Gly Thr Ser Ile His
1               5                   10

<210> SEQ ID NO 9
<211> LENGTH: 33
<212> TYPE: DNA
<213> ORGANISM: Mouse

<400> SEQUENCE: 9
cgagcaagtg aaaatattta cagttattta gca                          33

<210> SEQ ID NO 10
<211> LENGTH: 11
<212> TYPE: PRT
<213> ORGANISM: Mouse

<400> SEQUENCE: 10

Arg Ala Ser Glu Asn Ile Tyr Ser Tyr Leu Ala
1               5                   10

<210> SEQ ID NO 11
<211> LENGTH: 39
<212> TYPE: DNA
<213> ORGANISM: Mouse

<400> SEQUENCE: 11
cagagcctct ttgatattga tggaaagaca tatttgaat                    39

<210> SEQ ID NO 12
<211> LENGTH: 13
<212> TYPE: PRT
<213> ORGANISM: Mouse

<400> SEQUENCE: 12

Gln Ser Leu Phe Asp Ile Asp Gly Lys Thr Tyr Leu Asn
1               5                   10

<210> SEQ ID NO 13
<211> LENGTH: 33
<212> TYPE: DNA
<213> ORGANISM: Mouse

<400> SEQUENCE: 13
cgggcaagtc aggacattgg tggtagctta aac                          33

<210> SEQ ID NO 14
<211> LENGTH: 11
<212> TYPE: PRT
<213> ORGANISM: Mouse

<400> SEQUENCE: 14

Arg Ala Ser Gln Asp Ile Gly Gly Ser Leu Asn
1               5                   10

<210> SEQ ID NO 15
<211> LENGTH: 33

```
<212> TYPE: DNA
<213> ORGANISM: Mouse

<400> SEQUENCE: 15
agggccagcc agactattag cgacttctta cac                                    33

<210> SEQ ID NO 16
<211> LENGTH: 11
<212> TYPE: PRT
<213> ORGANISM: Mouse

<400> SEQUENCE: 16

Arg Ala Ser Gln Thr Ile Ser Asp Phe Leu His
1               5                   10

<210> SEQ ID NO 17
<211> LENGTH: 33
<212> TYPE: DNA
<213> ORGANISM: Mouse

<400> SEQUENCE: 17
agggcaagtg aggacataca cactcaatta gcc                                    33

<210> SEQ ID NO 18
<211> LENGTH: 11
<212> TYPE: PRT
<213> ORGANISM: Mouse

<400> SEQUENCE: 18

Arg Ala Ser Glu Asp Ile His Thr Gln Leu Ala
1               5                   10

<210> SEQ ID NO 19
<211> LENGTH: 48
<212> TYPE: DNA
<213> ORGANISM: Mouse

<400> SEQUENCE: 19
agatctagtc agtacattgt tcatagtact ggaaccacct atttagaa                    48

<210> SEQ ID NO 20
<211> LENGTH: 16
<212> TYPE: PRT
<213> ORGANISM: Mouse

<400> SEQUENCE: 20

Arg Ser Ser Gln Tyr Ile Val His Ser Thr Gly Thr Thr Tyr Leu Glu
1               5                   10                  15

<210> SEQ ID NO 21
<211> LENGTH: 48
<212> TYPE: DNA
<213> ORGANISM: Mouse

<400> SEQUENCE: 21
agatctagtc attaccttgt tcatgataac ggaaacacct atgttgaa                    48

<210> SEQ ID NO 22
<211> LENGTH: 16
<212> TYPE: PRT
<213> ORGANISM: Mouse

<400> SEQUENCE: 22

Arg Ser Ser His Tyr Leu Val His Asp Asn Gly Asn Thr Tyr Val Glu
```

<210> SEQ ID NO 23
<211> LENGTH: 48
<212> TYPE: DNA
<213> ORGANISM: Mouse

<400> SEQUENCE: 23
agatctagtc agaacattgt ccatagtact ggaaacacct atttagaa            48

<210> SEQ ID NO 24
<211> LENGTH: 16
<212> TYPE: PRT
<213> ORGANISM: Mouse

<400> SEQUENCE: 24

Arg Ser Ser Gln Asn Ile Val His Ser Thr Gly Asn Thr Tyr Leu Glu
1               5                   10                  15

<210> SEQ ID NO 25
<211> LENGTH: 30
<212> TYPE: DNA
<213> ORGANISM: Mouse

<400> SEQUENCE: 25
agtgtcagct caagtgtaag ttacatacac                                30

<210> SEQ ID NO 26
<211> LENGTH: 10
<212> TYPE: PRT
<213> ORGANISM: Mouse

<400> SEQUENCE: 26

Ser Val Ser Ser Ser Val Ser Tyr Ile His
1               5                   10

<210> SEQ ID NO 27
<211> LENGTH: 30
<212> TYPE: DNA
<213> ORGANISM: Mouse

<400> SEQUENCE: 27
agtgccagct caagtgtaag ttacatgtgc                                30

<210> SEQ ID NO 28
<211> LENGTH: 10
<212> TYPE: PRT
<213> ORGANISM: Mouse

<400> SEQUENCE: 28

Ser Ala Ser Ser Ser Val Ser Tyr Met Cys
1               5                   10

<210> SEQ ID NO 29
<211> LENGTH: 18
<212> TYPE: DNA
<213> ORGANISM: Mouse

<400> SEQUENCE: 29
cagggcatta acaattat                                             18

<210> SEQ ID NO 30
<211> LENGTH: 6
<212> TYPE: PRT

```
<213> ORGANISM: Mouse

<400> SEQUENCE: 30

Gln Gly Ile Asn Asn Tyr
1               5

<210> SEQ ID NO 31
<211> LENGTH: 21
<212> TYPE: DNA
<213> ORGANISM: Mouse

<400> SEQUENCE: 31
tatgcttcta agtctatatc t                                            21

<210> SEQ ID NO 32
<211> LENGTH: 7
<212> TYPE: PRT
<213> ORGANISM: Mouse

<400> SEQUENCE: 32

Tyr Ala Ser Lys Ser Ile Ser
1               5

<210> SEQ ID NO 33
<211> LENGTH: 21
<212> TYPE: DNA
<213> ORGANISM: Mouse

<400> SEQUENCE: 33
aatgcaaaaa ccttagcaga a                                            21

<210> SEQ ID NO 34
<211> LENGTH: 7
<212> TYPE: PRT
<213> ORGANISM: Mouse

<400> SEQUENCE: 34

Asn Ala Lys Thr Leu Ala Glu
1               5

<210> SEQ ID NO 35
<211> LENGTH: 21
<212> TYPE: DNA
<213> ORGANISM: Mouse

<400> SEQUENCE: 35
ctggtgtctg aattggactc t                                            21

<210> SEQ ID NO 36
<211> LENGTH: 7
<212> TYPE: PRT
<213> ORGANISM: Mouse

<400> SEQUENCE: 36

Leu Val Ser Glu Leu Asp Ser
1               5

<210> SEQ ID NO 37
<211> LENGTH: 21
<212> TYPE: DNA
<213> ORGANISM: Mouse

<400> SEQUENCE: 37
gccacatcca gcttagattc t                                            21
```

<210> SEQ ID NO 38
<211> LENGTH: 7
<212> TYPE: PRT
<213> ORGANISM: Mouse

<400> SEQUENCE: 38

Ala Thr Ser Ser Leu Asp Ser
1               5

<210> SEQ ID NO 39
<211> LENGTH: 21
<212> TYPE: DNA
<213> ORGANISM: Mouse

<400> SEQUENCE: 39
tatgcttccc aatccatctc t                                         21

<210> SEQ ID NO 40
<211> LENGTH: 7
<212> TYPE: PRT
<213> ORGANISM: Mouse

<400> SEQUENCE: 40

Tyr Ala Ser Gln Ser Ile Ser
1               5

<210> SEQ ID NO 41
<211> LENGTH: 21
<212> TYPE: DNA
<213> ORGANISM: Mouse

<400> SEQUENCE: 41
ggtgcagcca gtttgaaaag t                                         21

<210> SEQ ID NO 42
<211> LENGTH: 7
<212> TYPE: PRT
<213> ORGANISM: Mouse

<400> SEQUENCE: 42

Gly Ala Ala Ser Leu Lys Ser
1               5

<210> SEQ ID NO 43
<211> LENGTH: 21
<212> TYPE: DNA
<213> ORGANISM: Mouse

<400> SEQUENCE: 43
aaagtttcca accgattttc t                                         21

<210> SEQ ID NO 44
<211> LENGTH: 7
<212> TYPE: PRT
<213> ORGANISM: Mouse

<400> SEQUENCE: 44

Lys Val Ser Asn Arg Phe Ser
1               5

<210> SEQ ID NO 45
<211> LENGTH: 21
<212> TYPE: DNA

```
<213> ORGANISM: Mouse

<400> SEQUENCE: 45
gacacatcca aactggcttc t                                              21

<210> SEQ ID NO 46
<211> LENGTH: 7
<212> TYPE: PRT
<213> ORGANISM: Mouse

<400> SEQUENCE: 46

Asp Thr Ser Lys Leu Ala Ser
1               5

<210> SEQ ID NO 47
<211> LENGTH: 21
<212> TYPE: DNA
<213> ORGANISM: Mouse

<400> SEQUENCE: 47
tatacatcaa ctttacagtc a                                              21

<210> SEQ ID NO 48
<211> LENGTH: 7
<212> TYPE: PRT
<213> ORGANISM: Mouse

<400> SEQUENCE: 48

Tyr Thr Ser Thr Leu Gln Ser
1               5

<210> SEQ ID NO 49
<211> LENGTH: 27
<212> TYPE: DNA
<213> ORGANISM: Mouse

<400> SEQUENCE: 49
caacatagtt atagctggcc gtggacg                                        27

<210> SEQ ID NO 50
<211> LENGTH: 9
<212> TYPE: PRT
<213> ORGANISM: Mouse

<400> SEQUENCE: 50

Gln His Ser Tyr Ser Trp Pro Trp Thr
1               5

<210> SEQ ID NO 51
<211> LENGTH: 27
<212> TYPE: DNA
<213> ORGANISM: Mouse

<400> SEQUENCE: 51
cagcatcatt atggtattcc gttcacg                                        27

<210> SEQ ID NO 52
<211> LENGTH: 9
<212> TYPE: PRT
<213> ORGANISM: Mouse

<400> SEQUENCE: 52

Gln His His Tyr Gly Ile Pro Phe Thr
1               5
```

<210> SEQ ID NO 53
<211> LENGTH: 27
<212> TYPE: DNA
<213> ORGANISM: Mouse

<400> SEQUENCE: 53
tggcaaggta cacattttcc gctcacg                                        27

<210> SEQ ID NO 54
<211> LENGTH: 9
<212> TYPE: PRT
<213> ORGANISM: Mouse

<400> SEQUENCE: 54

Trp Gln Gly Thr His Phe Pro Leu Thr
1               5

<210> SEQ ID NO 55
<211> LENGTH: 27
<212> TYPE: DNA
<213> ORGANISM: Mouse

<400> SEQUENCE: 55
ctacaatatg ctagttctcc gtatacg                                        27

<210> SEQ ID NO 56
<211> LENGTH: 9
<212> TYPE: PRT
<213> ORGANISM: Mouse

<400> SEQUENCE: 56

Leu Gln Tyr Ala Ser Ser Pro Tyr Thr
1               5

<210> SEQ ID NO 57
<211> LENGTH: 27
<212> TYPE: DNA
<213> ORGANISM: Mouse

<400> SEQUENCE: 57
caaagtggta cacctttcc gtggacg                                         27

<210> SEQ ID NO 58
<211> LENGTH: 9
<212> TYPE: PRT
<213> ORGANISM: Mouse

<400> SEQUENCE: 58

Gln Ser Gly Asn Thr Phe Pro Trp Thr
1               5

<210> SEQ ID NO 59
<211> LENGTH: 27
<212> TYPE: DNA
<213> ORGANISM: Mouse

<400> SEQUENCE: 59
caacagtata ggagtattcc gtggacg                                        27

<210> SEQ ID NO 60
<211> LENGTH: 9
<212> TYPE: PRT
<213> ORGANISM: Mouse

```
<400> SEQUENCE: 60

Gln Gln Tyr Arg Ser Ile Pro Trp Thr
1               5

<210> SEQ ID NO 61
<211> LENGTH: 27
<212> TYPE: DNA
<213> ORGANISM: Mouse

<400> SEQUENCE: 61
tttcaaggtt cacatttcc attcacg                                         27

<210> SEQ ID NO 62
<211> LENGTH: 9
<212> TYPE: PRT
<213> ORGANISM: Mouse

<400> SEQUENCE: 62

Phe Gln Gly Ser His Phe Pro Phe Thr
1               5

<210> SEQ ID NO 63
<211> LENGTH: 27
<212> TYPE: DNA
<213> ORGANISM: Mouse

<400> SEQUENCE: 63
tttcaaggtt cacatttccc attcacg                                        27

<210> SEQ ID NO 64
<211> LENGTH: 9
<212> TYPE: PRT
<213> ORGANISM: Mouse

<400> SEQUENCE: 64

His Gln Trp Ser Thr Asn Pro Pro Thr
1               5

<210> SEQ ID NO 65
<211> LENGTH: 27
<212> TYPE: DNA
<213> ORGANISM: Mouse

<400> SEQUENCE: 65
cagcagtgga gtagtaaccc acccacg                                        27

<210> SEQ ID NO 66
<211> LENGTH: 9
<212> TYPE: PRT
<213> ORGANISM: Mouse

<400> SEQUENCE: 66

Gln Gln Trp Ser Ser Asn Pro Pro Thr
1               5

<210> SEQ ID NO 67
<211> LENGTH: 24
<212> TYPE: DNA
<213> ORGANISM: Mouse

<400> SEQUENCE: 67
cagcagttta gtaaacttcg gaca                                           24
```

```
<210> SEQ ID NO 68
<211> LENGTH: 8
<212> TYPE: PRT
<213> ORGANISM: Mouse

<400> SEQUENCE: 68

Gln Gln Phe Ser Lys Leu Arg Thr
1               5

<210> SEQ ID NO 69
<211> LENGTH: 36
<212> TYPE: DNA
<213> ORGANISM: Mouse

<400> SEQUENCE: 69
gggttctcac tgaccacttc tggcttgggt gttgcc                          36

<210> SEQ ID NO 70
<211> LENGTH: 12
<212> TYPE: PRT
<213> ORGANISM: Mouse

<400> SEQUENCE: 70

Gly Phe Ser Leu Thr Thr Ser Gly Leu Gly Val Ala
1               5                   10

<210> SEQ ID NO 71
<211> LENGTH: 30
<212> TYPE: DNA
<213> ORGANISM: Mouse

<400> SEQUENCE: 71
ggctacacct ttactagcta ctggatacac                                 30

<210> SEQ ID NO 72
<211> LENGTH: 10
<212> TYPE: PRT
<213> ORGANISM: Mouse

<400> SEQUENCE: 72

Gly Tyr Thr Phe Thr Ser Tyr Trp Ile His
1               5                   10

<210> SEQ ID NO 73
<211> LENGTH: 30
<212> TYPE: DNA
<213> ORGANISM: Mouse

<400> SEQUENCE: 73
ggcctcaaca ttaaagacat ctatattcac                                 30

<210> SEQ ID NO 74
<211> LENGTH: 10
<212> TYPE: PRT
<213> ORGANISM: Mouse

<400> SEQUENCE: 74

Gly Leu Asn Ile Lys Asp Ile Tyr Ile His
1               5                   10

<210> SEQ ID NO 75
<211> LENGTH: 30
<212> TYPE: DNA
<213> ORGANISM: Mouse
```

-continued

<210> SEQ ID NO 75
<211> LENGTH: 30
<212> TYPE: DNA
<213> ORGANISM: Mouse

<400> SEQUENCE: 75
ggttactcat tcaccaacta ctggatacac                               30

<210> SEQ ID NO 76
<211> LENGTH: 10
<212> TYPE: PRT
<213> ORGANISM: Mouse

<400> SEQUENCE: 76

Gly Tyr Ser Phe Thr Asn Tyr Trp Ile His
1               5                   10

<210> SEQ ID NO 77
<211> LENGTH: 30
<212> TYPE: DNA
<213> ORGANISM: Mouse

<400> SEQUENCE: 77
ggattcactt tcagtgacta tcccatgtct                               30

<210> SEQ ID NO 78
<211> LENGTH: 10
<212> TYPE: PRT
<213> ORGANISM: Mouse

<400> SEQUENCE: 78

Gly Phe Thr Phe Ser Asp Tyr Pro Met Ser
1               5                   10

<210> SEQ ID NO 79
<211> LENGTH: 30
<212> TYPE: DNA
<213> ORGANISM: Mouse

<400> SEQUENCE: 79
ggattcactt tcagtagctt tggcatgtct                               30

<210> SEQ ID NO 80
<211> LENGTH: 10
<212> TYPE: PRT
<213> ORGANISM: Mouse

<400> SEQUENCE: 80

Gly Phe Thr Phe Ser Ser Phe Gly Met Ser
1               5                   10

<210> SEQ ID NO 81
<211> LENGTH: 30
<212> TYPE: DNA
<213> ORGANISM: Mouse

<400> SEQUENCE: 81
ggattcactt tcagtaccta tggcatgtct                               30

<210> SEQ ID NO 82
<211> LENGTH: 10
<212> TYPE: PRT
<213> ORGANISM: Mouse

<400> SEQUENCE: 82

Gly Phe Thr Phe Ser Thr Tyr Gly Met Ser
1               5                   10

<210> SEQ ID NO 83
<211> LENGTH: 30
<212> TYPE: DNA
<213> ORGANISM: Mouse

<400> SEQUENCE: 83
ggattcactt tcagtagtta tggcatgtct         30

<210> SEQ ID NO 84
<211> LENGTH: 10
<212> TYPE: PRT
<213> ORGANISM: Mouse

<400> SEQUENCE: 84

Gly Phe Thr Phe Ser Ser Tyr Gly Met Ser
1               5                  10

<210> SEQ ID NO 85
<211> LENGTH: 36
<212> TYPE: DNA
<213> ORGANISM: Mouse

<400> SEQUENCE: 85
gggttttcac tgaccacttc tggtatgggt gtaggc         36

<210> SEQ ID NO 86
<211> LENGTH: 12
<212> TYPE: PRT
<213> ORGANISM: Mouse

<400> SEQUENCE: 86

Gly Phe Ser Leu Thr Thr Ser Gly Met Gly Val Gly
1               5                  10

<210> SEQ ID NO 87
<211> LENGTH: 36
<212> TYPE: DNA
<213> ORGANISM: Mouse

<400> SEQUENCE: 87
ggattttcac tgagcacttc tggtttgggt gtaggc         36

<210> SEQ ID NO 88
<211> LENGTH: 12
<212> TYPE: PRT
<213> ORGANISM: Mouse

<400> SEQUENCE: 88

Gly Phe Ser Leu Ser Thr Ser Gly Leu Gly Val Gly
1               5                  10

<210> SEQ ID NO 89
<211> LENGTH: 24
<212> TYPE: DNA
<213> ORGANISM: Mouse

<400> SEQUENCE: 89
ggattcacct tcagtgatta ttac         24

<210> SEQ ID NO 90
<211> LENGTH: 8
<212> TYPE: PRT
<213> ORGANISM: Mouse

```
<400> SEQUENCE: 90

Gly Phe Thr Phe Ser Asp Tyr Tyr
1               5

<210> SEQ ID NO 91
<211> LENGTH: 48
<212> TYPE: DNA
<213> ORGANISM: Mouse

<400> SEQUENCE: 91
cacatttggt cggatggtga cacgcgctat tacccagccc tgaagaac                    48

<210> SEQ ID NO 92
<211> LENGTH: 16
<212> TYPE: PRT
<213> ORGANISM: Mouse

<400> SEQUENCE: 92

His Ile Trp Ser Asp Gly Asp Thr Arg Tyr Tyr Pro Ala Leu Lys Asn
1               5                   10                  15

<210> SEQ ID NO 93
<211> LENGTH: 36
<212> TYPE: DNA
<213> ORGANISM: Mouse

<400> SEQUENCE: 93
tacattaatc ctgacactga ttatagtgag tacaat                                 36

<210> SEQ ID NO 94
<211> LENGTH: 12
<212> TYPE: PRT
<213> ORGANISM: Mouse

<400> SEQUENCE: 94

Tyr Ile Asn Pro Asp Thr Asp Tyr Ser Glu Tyr Asn
1               5                   10

<210> SEQ ID NO 95
<211> LENGTH: 36
<212> TYPE: DNA
<213> ORGANISM: Mouse

<400> SEQUENCE: 95
aggattgatc ctgcgaacgg taagactgca tatgac                                 36

<210> SEQ ID NO 96
<211> LENGTH: 12
<212> TYPE: PRT
<213> ORGANISM: Mouse

<400> SEQUENCE: 96

Arg Ile Asp Pro Ala Asn Gly Lys Thr Ala Tyr Asp
1               5                   10

<210> SEQ ID NO 97
<211> LENGTH: 36
<212> TYPE: DNA
<213> ORGANISM: Mouse

<400> SEQUENCE: 97
atgattgatc cttccgatgc tgaaactggg ttaaat                                 36
```

```
<210> SEQ ID NO 98
<211> LENGTH: 12
<212> TYPE: PRT
<213> ORGANISM: Mouse

<400> SEQUENCE: 98

Met Ile Asp Pro Ser Asp Ala Glu Thr Gly Leu Asn
1               5                   10

<210> SEQ ID NO 99
<211> LENGTH: 24
<212> TYPE: DNA
<213> ORGANISM: Mouse

<400> SEQUENCE: 99
gttagtgatg gtggtggttc cacc                                           24

<210> SEQ ID NO 100
<211> LENGTH: 8
<212> TYPE: PRT
<213> ORGANISM: Mouse

<400> SEQUENCE: 100

Val Ser Asp Gly Gly Gly Ser Thr
1               5

<210> SEQ ID NO 101
<211> LENGTH: 24
<212> TYPE: DNA
<213> ORGANISM: Mouse

<400> SEQUENCE: 101
attagtagtg ctggtagttt cacc                                           24

<210> SEQ ID NO 102
<211> LENGTH: 8
<212> TYPE: PRT
<213> ORGANISM: Mouse

<400> SEQUENCE: 102

Ile Ser Ser Ala Gly Ser Phe Thr
1               5

<210> SEQ ID NO 103
<211> LENGTH: 51
<212> TYPE: DNA
<213> ORGANISM: Mouse

<400> SEQUENCE: 103
accattaata ctaatggtgg taccacctat tatcgagaca gtgtgaaggg c             51

<210> SEQ ID NO 104
<211> LENGTH: 17
<212> TYPE: PRT
<213> ORGANISM: Mouse

<400> SEQUENCE: 104

Thr Ile Asn Thr Asn Gly Gly Thr Thr Tyr Tyr Arg Asp Ser Val Lys
1               5                   10                  15

Gly

<210> SEQ ID NO 105
<211> LENGTH: 51
<212> TYPE: DNA
```

<213> ORGANISM: Mouse

<400> SEQUENCE: 105
accataaata ctaatggtgg taacacctat tattcagaca atgtgaaggg c          51

<210> SEQ ID NO 106
<211> LENGTH: 17
<212> TYPE: PRT
<213> ORGANISM: Mouse

<400> SEQUENCE: 106

Thr Ile Asn Thr Asn Gly Gly Asn Thr Tyr Tyr Ser Asp Asn Val Lys
1               5                   10                  15
Gly

<210> SEQ ID NO 107
<211> LENGTH: 51
<212> TYPE: DNA
<213> ORGANISM: Mouse

<400> SEQUENCE: 107
accattagta ctaatggtgc caccgccaat tatccagaca gtgtgaaggg c          51

<210> SEQ ID NO 108
<211> LENGTH: 17
<212> TYPE: PRT
<213> ORGANISM: Mouse

<400> SEQUENCE: 108

Thr Ile Ser Thr Asn Gly Ala Thr Ala Asn Tyr Pro Asp Ser Val Lys
1               5                   10                  15
Gly

<210> SEQ ID NO 109
<211> LENGTH: 48
<212> TYPE: DNA
<213> ORGANISM: Mouse

<400> SEQUENCE: 109
cacatttggt gggatgatga taagtactat aatccatccc tgaagagc              48

<210> SEQ ID NO 110
<211> LENGTH: 16
<212> TYPE: PRT
<213> ORGANISM: Mouse

<400> SEQUENCE: 110

His Ile Trp Trp Asp Asp Asp Lys Tyr Tyr Asn Pro Ser Leu Lys Ser
1               5                   10                  15

<210> SEQ ID NO 111
<211> LENGTH: 48
<212> TYPE: DNA
<213> ORGANISM: Mouse

<400> SEQUENCE: 111
cacatttggt gggatgatga taagtactat aatccatccc ttaagaga              48

<210> SEQ ID NO 112
<211> LENGTH: 16
<212> TYPE: PRT
<213> ORGANISM: Mouse

```
<400> SEQUENCE: 112

His Ile Trp Trp Asp Asp Asp Lys Tyr Tyr Asn Pro Ser Leu Lys Arg
1               5                   10                  15

<210> SEQ ID NO 113
<211> LENGTH: 30
<212> TYPE: DNA
<213> ORGANISM: Mouse

<400> SEQUENCE: 113
attagaaatc gggctaatgg ttacacaaca                                    30

<210> SEQ ID NO 114
<211> LENGTH: 10
<212> TYPE: PRT
<213> ORGANISM: Mouse

<400> SEQUENCE: 114

Ile Arg Asn Arg Ala Asn Gly Tyr Thr Thr
1               5                   10

<210> SEQ ID NO 115
<211> LENGTH: 30
<212> TYPE: DNA
<213> ORGANISM: Mouse

<400> SEQUENCE: 115
atgaaggatg atagtctttta ctttgacaac                                   30

<210> SEQ ID NO 116
<211> LENGTH: 10
<212> TYPE: PRT
<213> ORGANISM: Mouse

<400> SEQUENCE: 116

Met Lys Asp Asp Ser Leu Tyr Phe Asp Asn
1               5                   10

<210> SEQ ID NO 117
<211> LENGTH: 30
<212> TYPE: DNA
<213> ORGANISM: Mouse

<400> SEQUENCE: 117
gcaagtgctg gttattattt ttttgacttc                                    30

<210> SEQ ID NO 118
<211> LENGTH: 10
<212> TYPE: PRT
<213> ORGANISM: Mouse

<400> SEQUENCE: 118

Ala Ser Ala Gly Tyr Tyr Phe Phe Asp Phe
1               5                   10

<210> SEQ ID NO 119
<211> LENGTH: 15
<212> TYPE: DNA
<213> ORGANISM: Mouse

<400> SEQUENCE: 119
ggtagggggg cccac                                                    15
```

<210> SEQ ID NO 120
<211> LENGTH: 5
<212> TYPE: PRT
<213> ORGANISM: Mouse

<400> SEQUENCE: 120

Gly Arg Gly Ala His
1               5

<210> SEQ ID NO 121
<211> LENGTH: 33
<212> TYPE: DNA
<213> ORGANISM: Mouse

<400> SEQUENCE: 121
gcaagaattg gcgattacta taatatggac tac                                    33

<210> SEQ ID NO 122
<211> LENGTH: 11
<212> TYPE: PRT
<213> ORGANISM: Mouse

<400> SEQUENCE: 122

Ala Arg Ile Gly Asp Tyr Tyr Asn Met Asp Tyr
1               5                   10

<210> SEQ ID NO 123
<211> LENGTH: 45
<212> TYPE: DNA
<213> ORGANISM: Mouse

<400> SEQUENCE: 123
acaagacatg cttcctacta tagctacgac cattctatgg actac                       45

<210> SEQ ID NO 124
<211> LENGTH: 15
<212> TYPE: PRT
<213> ORGANISM: Mouse

<400> SEQUENCE: 124

Thr Arg His Ala Ser Tyr Tyr Ser Tyr Asp His Ser Met Asp Tyr
1               5                   10                  15

<210> SEQ ID NO 125
<211> LENGTH: 36
<212> TYPE: DNA
<213> ORGANISM: Mouse

<400> SEQUENCE: 125
gcaagacggg ggtacgacgt tgggtgcttt gaccac                                 36

<210> SEQ ID NO 126
<211> LENGTH: 12
<212> TYPE: PRT
<213> ORGANISM: Mouse

<400> SEQUENCE: 126

Ala Arg Arg Gly Tyr Asp Val Gly Cys Phe Asp His
1               5                   10

<210> SEQ ID NO 127
<211> LENGTH: 27
<212> TYPE: DNA
<213> ORGANISM: Mouse

<400> SEQUENCE: 127
gcaagagact acggggctat ggactac                                27

<210> SEQ ID NO 128
<211> LENGTH: 9
<212> TYPE: PRT
<213> ORGANISM: Mouse

<400> SEQUENCE: 128

Ala Arg Asp Tyr Gly Ala Met Asp Tyr
1               5

<210> SEQ ID NO 129
<211> LENGTH: 27
<212> TYPE: DNA
<213> ORGANISM: Mouse

<400> SEQUENCE: 129
gcaactgaaa agggagctat gggctac                                27

<210> SEQ ID NO 130
<211> LENGTH: 9
<212> TYPE: PRT
<213> ORGANISM: Mouse

<400> SEQUENCE: 130

Ala Thr Glu Lys Gly Ala Met Gly Tyr
1               5

<210> SEQ ID NO 131
<211> LENGTH: 57
<212> TYPE: DNA
<213> ORGANISM: Mouse

<400> SEQUENCE: 131
gctcgaagaa ctgagactat gattacgaca gtgctatatt actatgctat ggactac      57

<210> SEQ ID NO 132
<211> LENGTH: 19
<212> TYPE: PRT
<213> ORGANISM: Mouse

<400> SEQUENCE: 132

Ala Arg Arg Thr Glu Thr Met Ile Thr Thr Val Leu Tyr Tyr Tyr Ala
1               5                   10                  15

Met Asp Tyr

<210> SEQ ID NO 133
<211> LENGTH: 54
<212> TYPE: DNA
<213> ORGANISM: Mouse

<400> SEQUENCE: 133
gctcgaagga gggaagttaa cttcggtatt aactattact attctatgga ctac          54

<210> SEQ ID NO 134
<211> LENGTH: 18
<212> TYPE: PRT
<213> ORGANISM: Mouse

<400> SEQUENCE: 134

Ala Arg Arg Arg Glu Val Asn Phe Gly Ile Asn Tyr Tyr Tyr Ser Met
1               5                   10                  15

Asp Tyr

<210> SEQ ID NO 135
<211> LENGTH: 36
<212> TYPE: DNA
<213> ORGANISM: Mouse

<400> SEQUENCE: 135
gtaagagatt cctatcacta cgggtacttc gatgtc                              36

<210> SEQ ID NO 136
<211> LENGTH: 12
<212> TYPE: PRT
<213> ORGANISM: Mouse

<400> SEQUENCE: 136

Val Arg Asp Ser Tyr His Tyr Gly Tyr Phe Asp Val
1               5                   10

<210> SEQ ID NO 137
<211> LENGTH: 324
<212> TYPE: DNA
<213> ORGANISM: Mouse

<400> SEQUENCE: 137
gacatcttgc tgactcagtc tccagccatc ctgtctgtga gtccaggaaa aagagtcagt    60
ttctcctgca gggccagtca gaacattggc acaagcatac actggtatca gcaaagaaca   120
aatggttctc caaggcttct cataaagtat gcttctaagt ctatatctgg gatttcttcc   180
aggtttagtg gcagtggctc agggacagat tttactctta gtatcaacag tgtggagtct   240
gaagatattg cagcttatta ctgtcaacat agttatagct ggccgtggac gttcggtgga   300
ggcaccaagc tggaaatcaa acgg                                          324

<210> SEQ ID NO 138
<211> LENGTH: 108
<212> TYPE: PRT
<213> ORGANISM: Mouse

<400> SEQUENCE: 138

Asp Ile Leu Leu Thr Gln Ser Pro Ala Ile Leu Ser Val Ser Pro Gly
1               5                   10                  15

Lys Arg Val Ser Phe Ser Cys Arg Ala Ser Gln Asn Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Lys Ser Ile Ser Gly Ile Ser Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Ala Tyr Tyr Cys Gln His Ser Tyr Ser Trp Pro Trp
                85                  90                  95

Thr Phe Gly Gly Gly Thr Lys Leu Glu Ile Lys Arg
            100                 105

<210> SEQ ID NO 139
<211> LENGTH: 324
<212> TYPE: DNA
<213> ORGANISM: Mouse

-continued

<400> SEQUENCE: 139

```
gacatccaga tgactcagtc tccagcctcc ctatctacat ctgtgggaga aactgtcacc      60
atcacatgtc gagcaagtga aaatatttac agttatttag catggtatca gcagagacag    120
ggaaaatctc ctcacctcct ggtcaataat gcaaaaacct tagcagaagg tgtgccatca    180
aggttcagtg gcagtggatc aggcacacat ttttctctga ggatcagcgg cctgcagcct    240
gaagattttg ggagttatta ctgtcagcat cattatggta ttccgttcac gttcggaggg    300
gggaccaagt tgtcaataaa acgg                                           324
```

<210> SEQ ID NO 140
<211> LENGTH: 108
<212> TYPE: PRT
<213> ORGANISM: Mouse

<400> SEQUENCE: 140

```
Asp Ile Gln Met Thr Gln Ser Pro Ala Ser Leu Ser Thr Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Arg Gln Gly Lys Ser Pro His Leu Leu Val
        35                  40                  45

Asn Asn Ala Lys Thr Leu Ala Glu Gly Val Pro Ser Arg Phe Ser Gly
    50                  55                  60

Ser Gly Ser Gly Thr His Phe Ser Leu Arg Ile Ser Gly Leu Gln Pro
65                  70                  75                  80

Glu Asp Phe Gly Ser Tyr Tyr Cys Gln His His Tyr Gly Ile Pro Phe
                85                  90                  95

Thr Phe Gly Gly Gly Thr Lys Leu Ser Ile Lys Arg
            100                 105
```

<210> SEQ ID NO 141
<211> LENGTH: 339
<212> TYPE: DNA
<213> ORGANISM: Mouse

<400> SEQUENCE: 141

```
gatgttgtga tgacccagat tccactcact ttgtcggtta ccattggaca accagcctcc     60
atctcttgca agtcaagtca gagcctcttt gatattgatg gaaagacata tttgaattgg    120
ttgttacaga ggccaggcca gtctccaaag cgcctaatct atctggtgtc tgaattggac    180
tctggagtcc ctgacaggtt cactggcagt ggatcaggga cagatttcac actgaaaatc    240
agcagagtgg aggctgagga tttgggagtt tactattgtt ggcaaggtac acattttccg    300
ctcacgttcg gtgctgggac caagctggag ctgaaacgg                           339
```

<210> SEQ ID NO 142
<211> LENGTH: 113
<212> TYPE: PRT
<213> ORGANISM: Mouse

<400> SEQUENCE: 142

```
Asp Val Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Phe Asp Ile
            20                  25                  30

Asp Gly Lys Thr Tyr Leu Asn Trp Leu Leu Gln Arg Pro Gly Gln Ser
        35                  40                  45
```

Pro Lys Arg Leu Ile Tyr Leu Val Ser Glu Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Leu Lys
            100                 105                 110

Arg

<210> SEQ ID NO 143
<211> LENGTH: 324
<212> TYPE: DNA
<213> ORGANISM: Mouse

<400> SEQUENCE: 143
gacatccaga tgacccagtc tccatcctcc ttatctgcct ctctgggaga aagagtcagt    60
ctcacttgtc gggcaagtca ggacattggt ggtagcttaa actggcttca gcagaaacca   120
gatggaacta ttaaacgcct gatctacgcc acatccagct tagattctgg tgtccccaaa   180
aggttcagtg gcagtaggtc tgggtcagtt ttttctctca ccatcaccag ccttgagtct   240
gaagattttg tagactattt ctgtctacaa tatgctagtt ctccgtatac gttcggaggg   300
gggaccaagc tggaaataaa acgg                                          324

<210> SEQ ID NO 144
<211> LENGTH: 108
<212> TYPE: PRT
<213> ORGANISM: Mouse

<400> SEQUENCE: 144

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Gly Ser
                20                  25                  30

Leu Asn Trp Leu Gln Gln Lys Pro Asp Gly Thr Ile Lys Arg Leu Ile
            35                  40                  45

Tyr Ala Thr Ser Ser Leu Asp Ser Gly Val Pro Lys Arg Phe Ser Gly
        50                  55                  60

Ser Arg Ser Gly Ser Val Phe Ser Leu Thr Ile Thr Ser Leu Glu Ser
65                  70                  75                  80

Glu Asp Phe Val Asp Tyr Phe Cys Leu Gln Tyr Ala Ser Ser Pro Tyr
                85                  90                  95

Thr Phe Gly Gly Gly Thr Lys Leu Glu Ile Lys Arg
            100                 105

<210> SEQ ID NO 145
<211> LENGTH: 324
<212> TYPE: DNA
<213> ORGANISM: Mouse

<400> SEQUENCE: 145
gacattgtga tgactcagtc tccagccacc ctgtctgtga ctccaggaga tagagtctct    60
ctttcctgca gggccagcca gactattagc gacttcttac actggtatca acaaaaatca   120
catgagtctc caaggcttct catcaaatat gcttcccaat ccatctctgg gatcccctcc   180
aggttcagtg gcactggatc agggtcagat ttcactctca ctatcaacag tgtggaacct   240

```
gaagatgttg gagtgtatta ctgtcaaagt ggtaacacct ttccgtggac gttcggtgga    300
ggcaccaagc tggaaatcaa acgg                                          324
```

<210> SEQ ID NO 146
<211> LENGTH: 108
<212> TYPE: PRT
<213> ORGANISM: Mouse

<400> SEQUENCE: 146

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Phe
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Thr Gly Ser Gly Ser Asp Phe Thr Leu Thr Ile Asn Ser Val Glu Pro
65                  70                  75                  80

Glu Asp Val Gly Val Tyr Tyr Cys Gln Ser Gly Asn Thr Phe Pro Trp
                85                  90                  95

Thr Phe Gly Gly Gly Thr Lys Leu Glu Ile Lys Arg
            100                 105
```

<210> SEQ ID NO 147
<211> LENGTH: 324
<212> TYPE: DNA
<213> ORGANISM: Mouse

<400> SEQUENCE: 147

```
gacatccaga tgacacaatc ttcatcctcc ttttctggat ttctaggaga cagagtcacc    60
attacttgca gggcaagtga ggacatacac actcaattag cctggtatca gcagaaacca   120
ggaaatgctc ctaggctctt aatatctggt gcagccagtt tgaaaagtgg ggttccttca   180
agattcagtg gcactggatc tggaaaggat tacactctca gcattaccag tcttcagact   240
gaagatgttg ctacatatta ctgtcaacag tataggagta ttccgtggac gttcggtgga   300
ggcaccaagc tggaaatcaa acgg                                          324
```

<210> SEQ ID NO 148
<211> LENGTH: 108
<212> TYPE: PRT
<213> ORGANISM: Mouse

<400> SEQUENCE: 148

```
Asp Ile Gln Met Thr Gln Ser Ser Ser Ser Phe Ser Gly Phe Leu Gly
1               5                   10                  15

Asp Arg Val Thr Ile Thr Cys Arg Ala Ser Glu Asp Ile His Thr Gln
            20                  25                  30

Leu Ala Trp Tyr Gln Gln Lys Pro Gly Asn Ala Pro Arg Leu Leu Ile
        35                  40                  45

Ser Gly Ala Ala Ser Leu Lys Ser Gly Val Pro Ser Arg Phe Ser Gly
    50                  55                  60

Thr Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Arg Ser Ile Pro Trp
                85                  90                  95
```

Thr Phe Gly Gly Gly Thr Lys Leu Glu Ile Lys Arg
            100                 105

<210> SEQ ID NO 149
<211> LENGTH: 339
<212> TYPE: DNA
<213> ORGANISM: Mouse

<400> SEQUENCE: 149
gatgttttga tgacccaaac tccgctctcc ctgcctgtca gtcttggaga tcacgcctcc      60
atctcttgca gatctagtca gtacattgtt catagtactg gaaccaccta tttagaatgg     120
tacctacaga aaccaggcca gtctccacag ctcctgatct acaaagtttc caaccgattt     180
tctggggtcc cagacaggtt cactggcagt ggatcaggga cagatttcac actcaggatc     240
agcagagtgg aggctgagga tctgggagtt tatttctgct ttcaaggttc acattttcca     300
ttcacgttcg gctcggggac aaagttggaa ataaaacgg                            339

<210> SEQ ID NO 150
<211> LENGTH: 113
<212> TYPE: PRT
<213> ORGANISM: Mouse

<400> SEQUENCE: 150

Asp Val Leu Met Thr Gln Thr Pro Leu Ser Leu Pro Val Ser Leu Gly
1               5                   10                  15

Asp His Ala Ser Ile Ser Cys Arg Ser Ser Gln Tyr Ile Val His Ser
            20                  25                  30

Thr Gly Thr Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Phe Cys Phe Gln Gly
                85                  90                  95

Ser His Phe Pro Phe Thr Phe Gly Ser Gly Thr Lys Leu Glu Ile Lys
            100                 105                 110

Arg

<210> SEQ ID NO 151
<211> LENGTH: 339
<212> TYPE: DNA
<213> ORGANISM: Mouse

<400> SEQUENCE: 151
gaagttgtga tgacccaaac tccactctcc ttgcctgtca gtcttggaga tcaagcctcc      60
atctcttgca gatctagtca ttaccttgtt catgataacg gaaacaccta tgttgaatgg     120
tacctgcaga agccaggcca gtctccaaag ctcctgatct acaaggtttc caaccgattt     180
tctggagtcc cagacaggtt tactggcagt ggttcaggga cagatttcac actcaagatc     240
agcagagtgg agtctgagga tctgggaatt tattactgct ttcaaggttc acatttccca     300
ttcacgttcg gctcggggac agagttggaa ataaaacgg                            339

<210> SEQ ID NO 152
<211> LENGTH: 113
<212> TYPE: PRT

<213> ORGANISM: Mouse

<400> SEQUENCE: 152

Glu Val Val Met Thr Gln Thr Pro Leu Ser Leu Pro Val Ser Leu Gly
1               5                   10                  15
Asp Gln Ala Ser Ile Ser Cys Arg Ser Ser His Tyr Leu Val His Asp
            20                  25                  30
Asn Gly Asn Thr Tyr Val Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ser Glu Asp Leu Gly Ile Tyr Tyr Cys Phe Gln Gly
                85                  90                  95
Ser His Phe Pro Phe Thr Phe Gly Ser Gly Thr Glu Leu Glu Ile Lys
            100                 105                 110
Arg

<210> SEQ ID NO 153
<211> LENGTH: 339
<212> TYPE: DNA
<213> ORGANISM: Mouse

<400> SEQUENCE: 153
gatgttttga tgacccaaac tccactctcc ctgcctgtca gtcttggaga tcaagcctcc      60
atctcttgca gatctagtca gaacattgtc catagtactg gaaacaccta tttagaatgg     120
tacctgcaga aaccaggcca gtctccaaag ctcctgattt ataaagtttc caaccgattt     180
tctggggtcc caaacaggtt ccgtggcagt ggatcaggga cagatttcac actcaagatc     240
accagagtgg aggctgagga tctgggaatt tattactgct ttcaaggttc acattttcca     300
ttcacgttcg gctcggggac aaagttggaa ataaaacgg                            339

<210> SEQ ID NO 154
<211> LENGTH: 113
<212> TYPE: PRT
<213> ORGANISM: Mouse

<400> SEQUENCE: 154

Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Asn Ile Val His Ser
            20                  25                  30
Thr Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asn Arg Phe Arg Gly Ser Gly Ser Gly Thr Asp Phe Thr Leu Lys Ile
65                  70                  75                  80
Thr Arg Val Glu Ala Glu Asp Leu Gly Ile Tyr Tyr Cys Phe Gln Gly
                85                  90                  95
Ser His Phe Pro Phe Thr Phe Gly Ser Gly Thr Lys Leu Glu Ile Lys
            100                 105                 110
Arg

-continued

<210> SEQ ID NO 155
<211> LENGTH: 321
<212> TYPE: DNA
<213> ORGANISM: Mouse

<400> SEQUENCE: 155

```
caaattgttc tcacccagtc tccagcaatc atgtctgcat ctccagggga gaaggtcacc    60
atgacctgca gtgtcagctc aagtgtaagt tacatacact ggtaccaaca gaagtcaggc   120
acctccccca aaagatggat ttatgacaca tccaaactgg cttctggagt ccctgctcgc   180
ttcagtggca gtgggtctgg gacctcttac tctctcacaa tcagcagcat ggaggctgaa   240
gatgctgcca cttattactg ccaccagtgg agtactaacc cacccacgtt cggagggggg   300
accaagctgg aaataagacg g                                             321
```

<210> SEQ ID NO 156
<211> LENGTH: 107
<212> TYPE: PRT
<213> ORGANISM: Mouse

<400> SEQUENCE: 156

Gln Ile Val Leu Thr Gln Ser Pro Ala Ile Met Ser Ala Ser Pro Gly
1               5                   10                  15

Glu Lys Val Thr Met Thr Cys Ser Val Ser Ser Ser Val Ser Tyr Ile
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Trp Ser Thr Asn Pro Pro Thr
                85                  90                  95

Phe Gly Gly Gly Thr Lys Leu Glu Ile Arg Arg
            100                 105

<210> SEQ ID NO 157
<211> LENGTH: 321
<212> TYPE: DNA
<213> ORGANISM: Mouse

<400> SEQUENCE: 157

```
caaattgttc tcacccagtc tccagcactc atgtctgcat ctccagggga gaaggtcacc    60
atgacctgca gtgccagctc aagtgtaagt tacatgtgct ggtaccagca gaagccaaga   120
tcctcccca aaccctggat ttatctcaca tccaacctgg cttctggagt ccctgctcgc   180
ttcagtggca gtgggtctgg gacctcttac tctctcacaa tcagtagcat ggaggctgaa   240
gatgctgcca cttattactg ccagcagtgg agtagtaacc cacccacgtt cggtgctggg   300
accaagctgg agctgaaacg g                                             321
```

<210> SEQ ID NO 158
<211> LENGTH: 107
<212> TYPE: PRT
<213> ORGANISM: Mouse

<400> SEQUENCE: 158

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
                 20                  25                  30

Cys Trp Tyr Gln Gln Lys Pro Arg Ser Ser Pro Lys Pro Trp Ile Tyr
             35                  40                  45

Leu Thr Ser Asn Leu Ala Ser Gly Val Pro Ala Arg Phe Ser Gly Ser
 50                      55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Pro Thr
                 85                  90                  95

Phe Gly Ala Gly Thr Lys Leu Glu Leu Lys Arg
            100                 105

<210> SEQ ID NO 159
<211> LENGTH: 321
<212> TYPE: DNA
<213> ORGANISM: Mouse

<400> SEQUENCE: 159
gaaatccaga tgacacagac tccatcctcc ctgtctgcct ctctgggaga cagagtcacc    60
atcacttgca gtgcaagtca gggcattaac aattatttga actggtatca gcagaaacca   120
ggtggaaaga ctagactcct catctattat acatcaactt acagtcagg agtcccatca   180 aggttcagtg gcagtgggtc tgggacacat tattctctca ccatcagcaa tctggaacct   240
gaagatattg ccacttacta ttgtcagcag tttagtaaac ttcggacatt cggtggaggc   300
accaggctgg aaatcaaacg g                                             321

<210> SEQ ID NO 160
<211> LENGTH: 107
<212> TYPE: PRT
<213> ORGANISM: Mouse

<400> SEQUENCE: 160

Glu Ile Gln Met Thr Gln Thr Pro Ser Ser Leu Ser Ala Ser Leu Gly
 1               5                  10                  15

Asp Arg Val Thr Ile Thr Cys Ser Ala Ser Gln Gly Ile Asn Asn Tyr
                 20                  25                  30

Leu Asn Trp Tyr Gln Gln Lys Pro Gly Gly Lys Thr Arg Leu Leu Ile
             35                  40                  45

Tyr Tyr Thr Ser Thr Leu Gln Ser Gly Val Pro Ser Arg Phe Ser Gly
 50                  55                  60

Ser Gly Ser Gly Thr His Tyr Ser Leu Thr Ile Ser Asn Leu Glu Pro
 65                  70                  75                  80

Glu Asp Ile Ala Thr Tyr Tyr Cys Gln Gln Phe Ser Lys Leu Arg Thr
                 85                  90                  95

Phe Gly Gly Gly Thr Arg Leu Glu Ile Lys Arg
            100                 105

<210> SEQ ID NO 161
<211> LENGTH: 324
<212> TYPE: DNA
<213> ORGANISM: Homo sapiens

<400> SEQUENCE: 161
gagattgtgc tgactcagag tccagacttc cagtcagtga cccccaagga gaaagtcacc    60
atcacatgcc gggcaagcca gaacatcggc acaagcattc actggtacca gcagaagccc   120

```
gatcagtccc ctaagctgct gatcaaatat gcctctaaga gtatttcagg ggtgccctct    180
agattcagcg gctccgggtc tggaacagac tttactctga ccattaactc cctggaggct    240
gaagatgccg ctacttacta ttgtcagcat agctactcat ggccttggac attcgggcag    300
gggaccaaag tggaaatcaa acgt                                           324
```

<210> SEQ ID NO 162
<211> LENGTH: 108
<212> TYPE: PRT
<213> ORGANISM: Homo sapiens

<400> SEQUENCE: 162

```
Glu Ile Val Leu Thr Gln Ser Pro Asp Phe Gln Ser Val Thr Pro Lys
1               5                  10                  15

Glu Lys Val Thr Ile Thr Cys Arg Ala Ser Gln Asn Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Lys Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln His Ser Tyr Ser Trp Pro Trp
                85                  90                  95

Thr Phe Gly Gln Gly Thr Lys Val Glu Ile Lys Arg
            100                 105
```

<210> SEQ ID NO 163
<211> LENGTH: 339
<212> TYPE: DNA
<213> ORGANISM: Homo sapiens

<400> SEQUENCE: 163

```
gatattgtga tgacccaaac tccgctctcc ctgtccgtca cccctggaca gccggcctcc     60
atctcttgca gatctagtca gaacattgtt catagtactg aaacacccta tttagaatgg    120
tacctacaga aaccaggcca gtctccacag ctcctgatct acaaagtttc caaccgattt    180
tctggggtcc cagacaggtt cagtggcagt ggatcaggga cagatttcac actcaaaatc    240
agcagagtgg aggctgagga tgttggagtt tattactgct ttcaaggttc acattttcca    300
ttcacgttcg gccaagggac caaggtggaa atcaaacgt                           339
```

<210> SEQ ID NO 164
<211> LENGTH: 113
<212> TYPE: PRT
<213> ORGANISM: Homo sapiens

<400> SEQUENCE: 164

```
Asp Ile Val Met Thr Gln Thr Pro Leu Ser Leu Ser Val Thr Pro Gly
1               5                  10                  15

Gln Pro Ala Ser Ile Ser Cys Arg Ser Ser Gln Asn Ile Val His Ser
            20                  25                  30

Thr Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Phe Gln Gly
              85                  90                  95

Ser His Phe Pro Phe Thr Phe Gly Gln Gly Thr Lys Val Glu Ile Lys
            100                 105                 110

Arg

<210> SEQ ID NO 165
<211> LENGTH: 360
<212> TYPE: DNA
<213> ORGANISM: Mouse

<400> SEQUENCE: 165
caggttactc tgaaagagtc tggccctggg atattgcagc cctcccagac cctcagtctg     60
acttgttctt tctctgggtt ctcactgacc acttctggct gggtgttgc ctggattcgt    120 cagccttcag ggaagggtct ggagtggctg gcacacattt ggtcgatgg tgacacgcgc    180 tattacccag ccctgaagaa ccgactgaca atctccaagg attcctccag caaccaggtc    240
ttcctcaaga tcgcccgtgt ggacactgca gatactgcca catactactg tgctcgaatg    300
aaggatgata gtctttactt tgacaactgg ggccaaggca ctattttcac agtctcctca    360

<210> SEQ ID NO 166
<211> LENGTH: 120
<212> TYPE: PRT
<213> ORGANISM: Mouse

<400> SEQUENCE: 166

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Ser
            20                  25                  30

Gly Leu Gly Val Ala Trp Ile Arg Gln Pro Ser Gly Lys Gly Leu Glu
        35                  40                  45

Trp Leu Ala His Ile Trp Ser Asp Gly Asp Thr Arg Tyr Tyr Pro Ala
    50                  55                  60

Leu Lys Asn Arg Leu Thr Ile Ser Lys Asp Ser Ser Asn Gln Val
65                  70                  75                  80

Phe Leu Lys Ile Ala Arg Val Asp Thr Ala Asp Thr Ala Thr Tyr Tyr
                85                  90                  95

Cys Ala Arg Met Lys Asp Asp Ser Leu Tyr Phe Asp Asn Trp Gly Gln
            100                 105                 110

Gly Thr Ile Phe Thr Val Ser Ser
        115                 120

<210> SEQ ID NO 167
<211> LENGTH: 351
<212> TYPE: DNA
<213> ORGANISM: Mouse

<400> SEQUENCE: 167
cagatccagt tggtgcagtc tggggctgaa ctggcaaaac ctggggcctc agtgaggatg     60
tcctgcgaga cttctggcta caccttact agctactgga tacactggat aaaagagagg    120
cctggacagg gtctggaatg gattggatac attaatcctg acactgatta tagtgagtac    180
aatcagaaat tcaaggacaa ggccagattg actgcagaca atcctccac acagcctac    240 atggagctga acagcctgac atttgatgat tctgcagtct attactgtgc aagtgctggt    300

```
tattattttt tgacttctg gggccaaggc accactctca cagtctcctc a         351
```

<210> SEQ ID NO 168
<211> LENGTH: 117
<212> TYPE: PRT
<213> ORGANISM: Mouse

<400> SEQUENCE: 168

| | | | | | | | | | | | | | | | |
|---|---|---|---|---|---|---|---|---|---|---|---|---|---|---|---|
| Gln | Ile | Gln | Leu | Val | Gln | Ser | Gly | Ala | Glu | Leu | Ala | Lys | Pro | Gly | Ala |
| 1 | | | | 5 | | | | | 10 | | | | | 15 | |
| Ser | Val | Arg | Met | Ser | Cys | Glu | Thr | Ser | Gly | Tyr | Thr | Phe | Thr | Ser | Tyr |
| | | | 20 | | | | | 25 | | | | | 30 | | |
| Trp | Ile | His | Trp | Ile | Lys | Glu | Arg | Pro | Gly | Gln | Gly | Leu | Glu | Trp | Ile |
| | | | 35 | | | | | 40 | | | | | 45 | | |
| Gly | Tyr | Ile | Asn | Pro | Asp | Thr | Asp | Tyr | Ser | Glu | Tyr | Asn | Gln | Lys | Phe |
| | 50 | | | | | 55 | | | | | 60 | | | | |
| Lys | Asp | Lys | Ala | Arg | Leu | Thr | Ala | Asp | Lys | Ser | Ser | Thr | Thr | Ala | Tyr |
| 65 | | | | | 70 | | | | | 75 | | | | | 80 |
| Met | Glu | Leu | Asn | Ser | Leu | Thr | Phe | Asp | Asp | Ser | Ala | Val | Tyr | Tyr | Cys |
| | | | | 85 | | | | | 90 | | | | | 95 | |
| Ala | Ser | Ala | Gly | Tyr | Tyr | Phe | Asp | Phe | Trp | Gly | Gln | Gly | Thr | Thr |
| | | | 100 | | | | | 105 | | | | | 110 | | |
| Leu | Thr | Val | Ser | Ser |
| | | | | 115 |

<210> SEQ ID NO 169
<211> LENGTH: 336
<212> TYPE: DNA
<213> ORGANISM: Mouse

<400> SEQUENCE: 169

```
gaggttcagc tgcagcagtc tggggcagaa cttgtgaaac caggggcctc agtcaagttg      60
tcctgtacaa cttctggcct caacattaaa gacatctata ttcactgggt gaagcagagg     120
cctgaacagg gcctggagtg gattgggagg attgatcctg cgaacggtaa gactgcatat     180
gacctgaagt tccaggccaa ggccactata acagcagaca catcttccaa aacagcctac     240
ctgcacctca gcagcctgac atctgaggac actgccgtct attactgtgg tagggggggcc     300
cactggggcc aaggcaccac tctcacagtc tcctca                              336
```

<210> SEQ ID NO 170
<211> LENGTH: 112
<212> TYPE: PRT
<213> ORGANISM: Mouse

<400> SEQUENCE: 170

| | | | | | | | | | | | | | | | |
|---|---|---|---|---|---|---|---|---|---|---|---|---|---|---|---|
| Glu | Val | Gln | Leu | Gln | Gln | Ser | Gly | Ala | Glu | Leu | Val | Lys | Pro | Gly | Ala |
| 1 | | | | 5 | | | | | 10 | | | | | 15 | |
| Ser | Val | Lys | Leu | Ser | Cys | Thr | Thr | Ser | Gly | Leu | Asn | Ile | Lys | Asp | Ile |
| | | | 20 | | | | | 25 | | | | | 30 | | |
| Tyr | Ile | His | Trp | Val | Lys | Gln | Arg | Pro | Glu | Gln | Gly | Leu | Glu | Trp | Ile |
| | | | 35 | | | | | 40 | | | | | 45 | | |
| Gly | Arg | Ile | Asp | Pro | Ala | Asn | Gly | Lys | Thr | Ala | Tyr | Asp | Leu | Lys | Phe |
| | 50 | | | | | 55 | | | | | 60 | | | | |
| Gln | Ala | Lys | Ala | Thr | Ile | Thr | Ala | Asp | Thr | Ser | Ser | Lys | Thr | Ala | Tyr |
| 65 | | | | | 70 | | | | | 75 | | | | | 80 |
| Leu | His | Leu | Ser | Ser | Leu | Thr | Ser | Glu | Asp | Thr | Ala | Val | Tyr | Tyr | Cys |
| | | | | 85 | | | | | 90 | | | | | 95 | |

Gly Arg Gly Ala His Trp Gly Gln Gly Thr Thr Leu Thr Val Ser Ser
            100                 105                 110

<210> SEQ ID NO 171
<211> LENGTH: 354
<212> TYPE: DNA
<213> ORGANISM: Mouse

<400> SEQUENCE: 171
cagatccagt tggtgcagtc tgggcctcag ctggttaggc ctggggcttc agtgaagata      60
tcctgcgagg cttctggtta ctcattcacc aactactgga tacactgggt gaagcagagg     120
cctggacagg gtcttgagtg gattggcatg attgatcctt ccgatgctga aactgggtta     180
aatcagaagt tcaaggacaa ggccacattg actgtagaca atcctccag cacagcctac      240 atgcaactca gcagcccgac atctgaagac tctgcggtct attactgtgc aagaattggc     300
gattactata atatggacta ctggggtcaa ggaaccctca gtcaccgtct ctca           354

<210> SEQ ID NO 172
<211> LENGTH: 118
<212> TYPE: PRT
<213> ORGANISM: Mouse

<400> SEQUENCE: 172

Gln Ile Gln Leu Val Gln Ser Gly Pro Gln Leu Val Arg Pro Gly Ala
1               5                   10                  15

Ser Val Lys Ile Ser Cys Glu Ala Ser Gly Tyr Ser Phe Thr Asn Tyr
            20                  25                  30

Trp Ile His Trp Val Lys Gln Arg Pro Gly Gln Gly Leu Glu Trp Ile
        35                  40                  45

Gly Met Ile Asp Pro Ser Asp Ala Glu Thr Gly Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Ile Gly Asp Tyr Tyr Asn Met Asp Tyr Trp Gly Gln Gly Thr
            100                 105                 110

Ser Val Thr Val Ser Ser
        115

<210> SEQ ID NO 173
<211> LENGTH: 366
<212> TYPE: DNA
<213> ORGANISM: Mouse

<400> SEQUENCE: 173
gaagtgaagg tggtggagtc tgggggaggt ttagtgcagc ctggagggtc cctgaaactc      60
tcctgtgcag cctctggatt cactttcagt gactatccca tgtcttgggt tcgccagact     120
ccagagaaga gactggagtg ggtcgcatac gttagtgatg gtggtggttc cacctactat     180
ccagacattg taagggccg attcaccatc tcccgagaca tgccaagaa cacccctgta      240 cttcaaatga gcagtctgaa gtctgaggac acggccatgt atttctgtac aagacatgct     300
tcctactata gctacgacca ttctatggac tactggggtc agggaaccctc agtcaccgtc    360 tcatca                                                                366

<210> SEQ ID NO 174
<211> LENGTH: 122
<212> TYPE: PRT
<213> ORGANISM: Mouse

<400> SEQUENCE: 174

Glu Val Lys Val Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Tyr
            20                  25                  30

Pro Met Ser Trp Val Arg Gln Thr Pro Glu Lys Arg Leu Glu Trp Val
        35                  40                  45

Ala Tyr Val Ser Asp Gly Gly Ser Thr Tyr Tyr Pro Asp Ile Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Phe Cys
                85                  90                  95

Thr Arg His Ala Ser Tyr Tyr Ser Tyr Asp His Ser Met Asp Tyr Trp
            100                 105                 110

Gly Gln Gly Thr Ser Val Thr Val Ser Ser
        115                 120

<210> SEQ ID NO 175
<211> LENGTH: 357
<212> TYPE: DNA
<213> ORGANISM: Mouse

<400> SEQUENCE: 175
cagatccagt tggtgcagtc tgggggagac ttagtgaggc ctggagggtc cctgaaactc      60
tcctgtgcag cctctggatt cactttcagt agctttggca tgtcttggat tcgccagact     120
ccagacaaga ggctggagtg gtcgcaacc attagtagtg ctggtagttt cacctactat     180
ccagacagtg tgaagggccg attcaccatc tccagagaca atgccaggaa caccctgtat     240
ctacaaatga acagtctgaa gtctgaggac tcagccatgt attactgtgc aagacggggg     300
tacgacgttg gtgctttga ccactggggc cgaggcacca ctctcacagt ctcctca         357

<210> SEQ ID NO 176
<211> LENGTH: 119
<212> TYPE: PRT
<213> ORGANISM: Mouse

<400> SEQUENCE: 176

Gln Ile Gln Leu Val Gln Ser Gly Gly Asp Leu Val Arg Pro Gly Gly
1               5                   10                  15

Ser Leu Lys Leu Ser Cys Ala Ala Ser Gly Phe Thr Phe Ser Ser Phe
            20                  25                  30

Gly Met Ser Trp Ile Arg Gln Thr Pro Asp Lys Arg Leu Glu Trp Val
        35                  40                  45

Ala Thr Ile Ser Ser Ala Gly Ser Phe Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Lys Ser Glu Asp Ser Ala Met Tyr Tyr Cys
                85                  90                  95

Ala Arg Arg Gly Tyr Asp Val Gly Cys Phe Asp His Trp Gly Arg Gly
            100                 105                 110

Thr Thr Leu Thr Val Ser Ser
        115

<210> SEQ ID NO 177
<211> LENGTH: 348
<212> TYPE: DNA
<213> ORGANISM: Mouse

<400> SEQUENCE: 177
gaggtgcacc tggtggagtc tgggggaggc ttagtgcagc ctggagggtc cctgaaactc    60
tcctgtgcag cctctggatt cactttcagt acctatggca tgtcttgggt tcgccagact   120
ccagacaaga ggctggagtt ggtcgcgacc attaatacta atggtggtac cacctattat   180
cgagacagtg tgaagggccg attcaccatc tccagagaca tgccaagaa caccctgtac   240 ctgcaaatga gcagtctgaa gtctgatgac acagccatgt attactgtgc aagagactac   300
ggggctatgg actactgggg tcaaggaacc tcagtcaccg tctcctca              348

<210> SEQ ID NO 178
<211> LENGTH: 116
<212> TYPE: PRT
<213> ORGANISM: Mouse

<400> SEQUENCE: 178

Glu Val His Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Gly Met Ser Trp Val Arg Gln Thr Pro Asp Lys Arg Leu Glu Leu Val
        35                  40                  45

Ala Thr Ile Asn Thr Asn Gly Gly Thr Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Asp Asp Thr Ala Met Tyr Tyr Cys
                85                  90                  95

Ala Arg Asp Tyr Gly Ala Met Asp Tyr Trp Gly Gln Gly Thr Ser Val
            100                 105                 110

Thr Val Ser Ser
        115

<210> SEQ ID NO 179
<211> LENGTH: 345
<212> TYPE: DNA
<213> ORGANISM: Mouse

<400> SEQUENCE: 179
gatgtgcacc tggtggagtc tgggggaggc ttagtgcagc ctggagggtc cctgacagtc    60
tcctgcgcag cctctggatt cactttcagt acctatggca tgtcttgggt tcgccagact   120
cgagacaaga ggctggagtt ggtcgcaacc ataaatacta atggtggtaa cacctattat   180
tcagacaatg tgaagggccg attcaccatt tccagagaca tgccaagaa caccctgtat   240 ttggaaatga gaggtctgag gtctggggac acagccatgt attactgtgc aagagactac   300
ggggctatgg actactgggg tcaaggaacc tcagtcaccg tctct                  345

<210> SEQ ID NO 180
<211> LENGTH: 115

```
<212> TYPE: PRT
<213> ORGANISM: Mouse

<400> SEQUENCE: 180

Asp Val His Leu Val Glu Ser Gly Gly Gly Leu Val Gln Pro Gly Gly
1               5                   10                  15

Ser Leu Thr Val Ser Cys Ala Ala Ser Gly Phe Thr Phe Ser Thr Tyr
            20                  25                  30

Gly Met Ser Trp Val Arg Gln Thr Arg Asp Lys Arg Leu Glu Leu Val
        35                  40                  45

Ala Thr Ile Asn Thr Asn Gly Gly Asn Thr Tyr Tyr Ser Asp Asn Val
    50                  55                  60

Lys Gly Arg Phe Thr Ile Ser Arg Asp Asn Ala Lys Asn Thr Leu Tyr
65                  70                  75                  80

Leu Glu Met Arg Gly Leu Arg Ser Gly Asp Thr Ala Met Tyr Tyr Cys
                85                  90                  95

Ala Arg Asp Tyr Gly Ala Met Asp Tyr Trp Gly Gln Gly Thr Ser Val
            100                 105                 110

Thr Val Ser
        115

<210> SEQ ID NO 181
<211> LENGTH: 348
<212> TYPE: DNA
<213> ORGANISM: Mouse

<400> SEQUENCE: 181
gaggtgcagc tgcagcagcc tggggggaggc ttagtacagc tggagggtc cctgacactc      60 tcctgtgcaa cctctggatt cactttcagt agttatggca tgtcttgggt tcgccagact     120
ccagccaaga ggctggagtt ggtcgcaacc attagtacta atggtgccac cgccaattat     180
ccagacagtg tgaagggccg attcaccatc tccagacaca atgccaagag caccctgtac     240
ctacaaatgc gcagtctgaa gtctgaggac acagccatgt attactgtgc aactgaaaag     300
ggagctatgg gctactgggg tcaaggaacc tcagtcaccg tctcctca                  348

<210> SEQ ID NO 182
<211> LENGTH: 116
<212> TYPE: PRT
<213> ORGANISM: Mouse

<400> SEQUENCE: 182

Glu Val Gln Leu Gln Gln Pro Gly Gly Gly Leu Val Gln Pro Gly Gly
1               5                   10                  15

Ser Leu Thr Leu Ser Cys Ala Thr Ser Gly Phe Thr Phe Ser Ser Tyr
            20                  25                  30

Gly Met Ser Trp Val Arg Gln Thr Pro Ala Lys Arg Leu Glu Leu Val
        35                  40                  45

Ala Thr Ile Ser Thr Asn Gly Ala Thr Ala Asn Tyr Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Arg Ser Leu Lys Ser Glu Asp Thr Ala Met Tyr Tyr Cys
                85                  90                  95

Ala Thr Glu Lys Gly Ala Met Gly Tyr Trp Gly Gln Gly Thr Ser Val
            100                 105                 110

Thr Val Ser Ser
```

<210> SEQ ID NO 183
<211> LENGTH: 381
<212> TYPE: DNA
<213> ORGANISM: Mouse

<400> SEQUENCE: 183

```
caagttactc taaaagagtc tggccctggg atattgaagc cctcacagac cctcagtctg    60
acttgttctt tctctgggtt ttcactgacc acttctggta tgggtgtagg ctggattcgt   120
cagccttcag ggaagggtct ggagtggctg gcacacattt ggtgggatga tgataagtac   180
tataatccat ccctgaagag ccaggtcaca atctccaagg acacctccag aaaccaggta   240
ttcctcaaga tcaccagtgt ggacactgca gatactgcca cttactactg tgctcgaaga   300
actgagacta tgattacgac agtgctatat tactatgcta tggactactg gggtcaagga   360
acctcagtca ccgtctcctc a                                             381
```

<210> SEQ ID NO 184
<211> LENGTH: 127
<212> TYPE: PRT
<213> ORGANISM: Mouse

<400> SEQUENCE: 184

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Thr Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Val Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Thr Glu Thr Met Ile Thr Thr Val Leu Tyr Tyr Tyr
            100                 105                 110

Ala Met Asp Tyr Trp Gly Gln Gly Thr Ser Val Thr Val Ser Ser
        115                 120                 125

<210> SEQ ID NO 185
<211> LENGTH: 378
<212> TYPE: DNA
<213> ORGANISM: Mouse

<400> SEQUENCE: 185

```
caagttactc taaaagagtc tggccctggg atattgaagc cctcacagac cctcagtctg    60
acttgttctt tctctggatt ttcactgagc acttctggtt tgggtgtagg ctggattcgt   120
cagccttcag ggaagggtct ggagtggctg gcacacattt ggtgggatga tgataagtac   180
tataatccat cccttaagag acagatcaca atctccaagg attcctccag aaaccaggta   240
ttcctcaaga tcaccaatgt ggacactgca gatactgcca cttactactg tgctcgaagg   300
agggaagtta acttcggtat taactattac tattctatgg actactgggg tcaaggaacc   360
tcagtcaccg tctcctca                                                 378
```

<210> SEQ ID NO 186
<211> LENGTH: 126
<212> TYPE: PRT
<213> ORGANISM: Mouse

<400> SEQUENCE: 186

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Leu Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Arg Gln Ile Thr Ile Ser Lys Asp Ser Ser Arg Asn Gln Val
65                  70                  75                  80

Phe Leu Lys Ile Thr Asn Val Asp Thr Ala Asp Thr Ala Thr Tyr Tyr
                85                  90                  95

Cys Ala Arg Arg Arg Glu Val Asn Phe Gly Ile Asn Tyr Tyr Tyr Ser
            100                 105                 110

Met Asp Tyr Trp Gly Gln Gly Thr Ser Val Thr Val Ser Ser
        115                 120                 125

<210> SEQ ID NO 187
<211> LENGTH: 363
<212> TYPE: DNA
<213> ORGANISM: Mouse

<400> SEQUENCE: 187
gaggtgaagc tggtggagtc tggaggacgc ttggtacagc ctgggaattc tctgagactc      60
tcctgtgcaa cttctggatt caccttcagt gattattaca tgagttgggt ccgccagact     120
ccaggaaggg cacttgagtg gttgagtttt attagaaatc gggctaatgg ttacacaaca     180
gagtacagtg catctgtgaa gggtcgattc accatctcca gagataattc ccaaagcatc     240
ctctatcttc acatgagcac cctgagacct gaggacagtg ccacttatta ctgtgtaaga     300
gattcctatc actacgggta cttcgatgtc tggggcgcag ggaccacggt caccgtctcc     360
tca                                                                   363

<210> SEQ ID NO 188
<211> LENGTH: 121
<212> TYPE: PRT
<213> ORGANISM: Mouse

<400> SEQUENCE: 188

Glu Val Lys Leu Val Glu Ser Gly Gly Arg Leu Val Gln Pro Gly Asn
1               5                   10                  15

Ser Leu Arg Leu Ser Cys Ala Thr Ser Gly Phe Thr Phe Ser Asp Tyr
            20                  25                  30

Tyr Met Ser Trp Val Arg Gln Thr Pro Gly Arg Ala Leu Glu Trp Leu
        35                  40                  45

Ser Phe Ile Arg Asn Arg Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu His Met Ser Thr Leu Arg Pro Glu Asp Ser Ala Thr Tyr
                85                  90                  95

Tyr Cys Val Arg Asp Ser Tyr His Tyr Gly Tyr Phe Asp Val Trp Gly
            100                 105                 110

Ala Gly Thr Thr Val Thr Val Ser Ser
        115                 120

<210> SEQ ID NO 189
<211> LENGTH: 360
<212> TYPE: DNA
<213> ORGANISM: Homo sapiens

<400> SEQUENCE: 189
caggtgaccc tgaaggaatc cgggcctact ctggtgaaac ctacccagac tctgactctg    60
acttgtactt ttagcggctt ctcactgacc acatctggac tgggagtggc ttggatcaga   120
cagcctcctg gaaaggccct ggagtggctg gctcacattt ggagcgacgg cgatactcgg   180
tactatccag ccctgaaaaa cagactgact atcaccaagg acacatccaa aaaccaggtg   240
gtcctgacaa tgactaatat gacccccgtc gataccgcaa catactattg cgcccatatg   300
aaggatgact ctctgtactt tgataactgg gggcagggaa ctctggtgac cgtgagcagc   360

<210> SEQ ID NO 190
<211> LENGTH: 120
<212> TYPE: PRT
<213> ORGANISM: Homo sapiens

<400> SEQUENCE: 190

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Thr Thr Ser
            20                  25                  30

Gly Leu Gly Val Ala Trp Ile Arg Gln Pro Pro Gly Lys Ala Leu Glu
        35                  40                  45

Trp Leu Ala His Ile Trp Ser Asp Gly Asp Thr Arg Tyr Tyr Pro Ala
    50                  55                  60

Leu Lys Asn Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Met Lys Asp Asp Ser Leu Tyr Phe Asp Asn Trp Gly Gln
            100                 105                 110

Gly Thr Leu Val Thr Val Ser Ser
        115                 120

<210> SEQ ID NO 191
<211> LENGTH: 348
<212> TYPE: DNA
<213> ORGANISM: Homo sapiens

<400> SEQUENCE: 191
gaggtgcagc tgctggaatc tggggggga ctggtgcagc ctggaggaag cctgagactg    60
agttgtgccg caagtgggtt tacatttagc tcctacggaa tgagctgggt gaggcaggct   120
ccaggcaagg gactggagtg gtctctgca atcagtacca acgagccac agcttactat   180 gccgactccg tgaagggccg gttcactatc tcaagagata cagcaagaa caccctgtat   240 ctgcagatga attctctgcg ggcagaagac acagccgtct actattgcgc tactgagaaa   300
ggggcaatga gccactgggg acagggcaca ctggtgaccg tgagttcc                348

-continued

<210> SEQ ID NO 192
<211> LENGTH: 116
<212> TYPE: PRT
<213> ORGANISM: Homo sapiens

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ala Ile Ser Thr Asn Gly Ala Thr Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Lys Gly Ala Met Ser His Trp Gly Gln Gly Thr Leu Val
            100                 105                 110

Thr Val Ser Ser
        115

<210> SEQ ID NO 193
<211> LENGTH: 318
<212> TYPE: DNA
<213> ORGANISM: Mouse

<400> SEQUENCE: 193
gctgatgctg caccaactgt atccatcttc ccaccatcca gtgagcagtt aacatctgga      60
ggtgcctcag tcgtgtgctt cttgaacaac ttctacccca agacatcaa tgtcaagtgg      120 aagattgatg gcagtgaacg acaaaatggc gtcctgaaca gttggactga tcaggacagc     180
aaagacagca cctacagcat gagcagcacc ctcacgttga ccaaggacga gtatgaacga     240
cataacagct atacctgtga ggccactcac aagacatcaa cttcacccat tgtcaagagc     300
ttcaacagga atgagtgt                                                    318

<210> SEQ ID NO 194
<211> LENGTH: 106
<212> TYPE: PRT
<213> ORGANISM: Mouse

<400> SEQUENCE: 194

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 195
<211> LENGTH: 315
<212> TYPE: DNA
<213> ORGANISM: Mouse

<400> SEQUENCE: 195

```
ggtcagccca agtccactcc cactctcacc gtgtttccac cttcctctga ggagctcaag      60
gaaaacaaag ccacactggt gtgtctgatt ccaactttt ccccgagtgg tgtgacagtg     120
gcctggaagg caaatggtac acctatcacc cagggtgtgg acacttcaaa tcccaccaaa     180
gagggcaaca agttcatggc cagcagcttc tacatttga catcggacca gtggagatct     240
cacaacagtt ttacctgtca agttacacat gaaggggaca ctgtggagaa gagtctgtct     300
cctgcagaat gtctc                                                     315
```

<210> SEQ ID NO 196
<211> LENGTH: 105
<212> TYPE: PRT
<213> ORGANISM: Mouse

<400> SEQUENCE: 196

```
Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Gly Asn Lys
    50                  55                  60

Phe Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100                 105
```

<210> SEQ ID NO 197
<211> LENGTH: 975
<212> TYPE: DNA
<213> ORGANISM: Mouse

<400> SEQUENCE: 197

```
gccaaaacaa cagccccatc ggtctatcca ctggcccctg tgtgtggaga tacaactggc      60
tcctcggtga ctctaggatg cctggtcaag ggttatttcc ctgagccagt gaccttgacc     120
tggaactctg gatccctgtc cagcggtgtg cacaccttcc cagctgtcct gcagtctgac     180
ctctacactc tgagcagctc agtgactgtc cctccagca cctggcccag cgagaccgtc     240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360 ccccaaagc ccaaggatgt gctcaccatt actctgactc ctaaggtcac gtgtgttgtg     420
gtagacatca gcaaggatga tcccgaggtc cagttcagct ggtttgtaga tgatgtggag     480
gtgcacacag ctcagacgca accccgggag gagcagttca acagcacttt ccgctcagtc     540
agtgaacttc ccatcatgca ccaggactgg ctcaatggaa aggagttcaa atgcagggtc     600
aacagtgcag ctttccctgc ccccatcgag aaaaccatct ccaaaaccaa aggcagaccg     660
```

```
aaggctccac aggtgtacac cattccacct cccaaggagc agatggccaa ggataaagtc    720
agtctgacct gcatgataac agacttcttc cctgaagaca ttactgtgga gtggcagtgg    780
aatgggcagc cagcggagaa ctacaagaac actcagccca tcatggacac agatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aaggc                                                    975
```

<210> SEQ ID NO 198
<211> LENGTH: 325
<212> TYPE: PRT
<213> ORGANISM: Mouse

<400> SEQUENCE: 198

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
```

```
305                 310                 315                 320
Ser Pro Gly Lys Gly
            325
```

<210> SEQ ID NO 199
<211> LENGTH: 20
<212> TYPE: DNA
<213> ORGANISM: Artificial sequence
<220> FEATURE:
<223> OTHER INFORMATION: Primer

<400> SEQUENCE: 199
tttggrggga agatgaagac                                              20

<210> SEQ ID NO 200
<211> LENGTH: 21
<212> TYPE: DNA
<213> ORGANISM: Artificial sequence
<220> FEATURE:
<223> OTHER INFORMATION: Primer

<400> SEQUENCE: 200
ttaacactct cccctgttga a                                            21

<210> SEQ ID NO 201
<211> LENGTH: 21
<212> TYPE: DNA
<213> ORGANISM: Artificial sequence
<220> FEATURE:
<223> OTHER INFORMATION: Primer

<400> SEQUENCE: 201
ttaacactca ttcctgttga a                                            21

<210> SEQ ID NO 202
<211> LENGTH: 21
<212> TYPE: DNA
<213> ORGANISM: Artificial sequence
<220> FEATURE:
<223> OTHER INFORMATION: Primer

<400> SEQUENCE: 202
tggacaggga tccagagttc c                                            21

<210> SEQ ID NO 203
<211> LENGTH: 21
<212> TYPE: DNA
<213> ORGANISM: Artificial sequence
<220> FEATURE:
<223> OTHER INFORMATION: Primer

<400> SEQUENCE: 203
tggacagggc tccatagttc c                                            21

<210> SEQ ID NO 204
<211> LENGTH: 20
<212> TYPE: DNA
<213> ORGANISM: Artificial sequence
<220> FEATURE:
<223> OTHER INFORMATION: Primer

<400> SEQUENCE: 204
actcgtcctt ggtcaacgtg                                              20

HUMAN ENDOTHELIN RECEPTOR ANTIBODY AND USE THEREOF

CROSS REFERENCE TO RELATED APPLICATIONS

This application is a continuation of U.S. application Ser. No. 15/537,190; which is a National Stage of International Application No. PCT/CN2016/090960, filed Jul. 22, 2016; which claims the benefit of the priority of Chinese Patent Application No. 201510867288.7, filed Dec. 1, 2015; the disclosure of each of which is incorporated herein by reference in its entirety.

REFERENCE TO A SEQUENCE LISTING

The present specification is being filed with a Sequence Listing in Computer Readable Form (CRF), which is entitled 14254-014-999_SEQLIST.txt of 91,739 bytes in size and was created Aug. 12, 2019; the content of which is incorporated herein by reference in its entirety.

FIELD

The present invention relates to an antibody, especially an antibody specifically binding to a human endothelin receptor, and uses thereof.

BACKGROUND

Endothelin (ET) is a vasoconstriction peptide hormone, important to the homeostasis and regulation of the biological functions of the cardiovascular system. ET is found not only in the endothelium but also in many other tissues and cell types (Barton et al., 2008, *Can. J. Physiol. Pharmacol.* 86:485-498). ET is a 2,400 Da peptide of 21 amino acids, having 2 disulfide bonds at its N-terminus, linking the 1st and 15th cysteine residues and the 3rd and 11th cysteine residues, respectively. Its C-terminus contains hydrophobic amino acid residues. Its N-terminal structure is important for binding to its receptor, while its C-terminal structure is important as to where on the receptor to bind. ET has three isoforms: ET-1, ET-2 and ET-3. They differ by a few amino acid residues. ET-1 plays a major role in the regulation of the biological functions of the cardiovascular system. Upon stimulation, endothelial cells synthesize and release ET-1. ET-1 is mainly regulated at the transcription level.

Endothelin receptors (ETR) has two isoforms: $ET_AR$ and $ET_BR$, which belong to the G protein coupled receptor (GPCR) family. Upon stimulation, $ET_AR$ activates membrane $Na^+/Ca^{2+}$ exchanger (NCX) and $Na^+/H^+$ exchanger (NHE) to increase cellular $Ca^{2+}$ concentrations and to sensitize muscle fibers to $Ca^{2+}$, resulting in the constriction of vascular smooth muscle and cardiac muscle (Neylon, 1999, *Clin. Exp. Pharmacol. Physiol.* 26:149-153). Unlike $ET_AR$, $ET_BR$ mainly relaxes the vascular smooth muscle cells and cardiac muscle cells (Nelson et al., 2003, *Nat. Rev. Cancer* 3:110-113).

Pulmonary artery hypertension (PAH) is due to the vasoconstriction of the lung or lung related vasculature, resulting in lung artery insufficiency and a compensatory increase in the blood pressure of the heart. On the microscopic scale, there appear to be changes in the small pulmonary arteries, including intimal fibrosis, medial hypertrophy, and plexiform lesions, causing in situ thrombosis of elastic and small pulmonary arteries, and resulting in increased blood circulation resistance in the whole lung vasculature (Simonneau et al., 2004, *J. Am. Coll. Cardiol.* 43:5S-12S; Barst et al., 2004, *J. Am. Coll. Cardiol.* 43:40S-47S). It has been shown that an $ET_AR$ antagonist can effectively block the vasoconstrictive signaling of ET-1, ameliorate PAH symptoms, and improve exercise capability and hemodynamics in PAH patients (Serasli et al., 2010, *Recent Pat. Cardiovasc. Drug Discov.* 5:184-95).

The present invention provides antibodies specifically binding to $ET_AR$, which can inhibit ET-1 signaling. The antibodies can be used as a monotherapy or combination therapy to treat PAH. The antibodies can also be used in diagnostic applications.

SUMMARY

The objective of the present invention is to provide an antibody specifically binding to a human endothelin receptor, which can inhibit its biological functions. The antibody of the present invention can be used for treating PAH.

$ET_AR$, a member of class A of the GPCR family, comprises seven transmembrane domains. Its extracellular domain is very small, only 1/7 of the complete protein sequence. However, GPCR antibodies focus on its extracellular domain. Because of the structural characteristics and low abundance of GPCR, it is difficult to prepare a biologically active GPCR immunogen. GPCR as a transmembrane protein is also difficult to purify. To obtain a GPCR monoclonal antibody, it cannot be accomplished by using its N-terminal peptide only, and a whole cell or cell membrane is usually used and followed by binding and functional characterization with whole cells. The present invention provides a unique immunization method with whole cells and cell membranes and a murine monoclonal antibody that can inhibit $ET_AR$ biological functions. The present invention further provides a method to humanize the murine monoclonal antibody for therapeutic applications in human.

The present invention provides:

An antibody specifically binding to a human endothelin receptor comprises an amino acid sequence selected from:
(a) a light chain CDR3 sequence selected from:
  light chain CDR3 sequences differing by no more than three amino acid additions, substitutions, and/or deletions in total from one of L1-L12 light chain CDR3 sequences: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68;
(b) a heavy chain CDR3 sequence selected from:
  heavy chain CDR3 sequences differing by no more than four amino acid additions, substitutions, and/or deletions in total from one of H1-H12 heavy chain CDR3 sequences: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136; and
(c) light chain CDR3 sequence (a) and heavy chain CDR3 sequence (b).

Preferably, the antibody further comprises one or more amino acid sequences selected from:
(a) a light chain CDR1 sequence selected from:
  light chain CDR1 sequences differing by no more than three amino acid additions, substitutions, and/or deletions from one of L1-L12 light chain CDR1 sequences: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30;

(b) a light chain CDR2 sequence selected from:
light chain CDR2 sequences differing by no more than two amino acid additions, substitutions, and/or deletions from one of L1-L12 light chain CDR2 sequences: SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, and SEQ ID NO: 48;

(c) a heavy chain CDR1 sequence selected from:
heavy chain CDR1 sequences differing by no more than two amino acid additions, substitutions, and/or deletions in total from one of H1-H12 heavy chain CDR1 sequences: SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90; and (d) a heavy chain CDR2 sequence selected from:
heavy chain CDR2 sequences differing by no more than three amino acid additions, substitutions, and/or deletions in total from one of H1-H12 heavy chain CDR2 sequences: SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO: 114.

An antibody specifically binding to a human endothelin receptor comprises an amino acid sequence selected from:

(a) one or more light chain variable regions selected from:
i. light chain CDR1 sequences: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30;
ii. light chain CDR2 sequences: SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, and SEQ ID NO: 48; and
iii. light chain CDR3 sequences: SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68;

(b) one or more heavy chain variable regions selected from:
i. heavy chain CDR1 sequences: SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, and SEQ ID NO: 90;
ii. heavy chain CDR2 sequences: SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, and SEQ ID NO: 114; and
iii. heavy chain CDR3 sequences: SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, and SEQ ID NO: 136; and (c) light chain variable region (a) and heavy chain variable region (b).

An antibody specifically binding to a human endothelin receptor comprises an amino acid sequence selected from:

(a) a light chain variable domain selected from:
i. amino acid sequences that are at least 80% identical to any of L1-L14 light chain variable domain sequences: SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, and SEQ ID NO: 164; and
ii. amino acid sequences encoded by polynucleotide sequences that are at least 80% identical to any of the polynucleotide sequences encoding for L1-L14 light chain variable domain sequences: SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, and SEQ ID NO: 163;

(b) a heavy chain variable domain sequence selected from:
i. amino acid sequences that are at least 80% identical to any of H1-H14 heavy chain variable domain sequences: SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, and SEQ ID NO: 192; and
ii. an amino acid sequences encoded by polynucleotide sequences that are at least 80% identical to any of the polynucleotide sequences encoding for H1-H14 heavy chain variable domain sequences: SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, and SEQ ID NO: 191; and (c) light chain variable domain sequence (a) and heavy chain variable domain sequence (b).

Preferably, the antibody comprises an amino acid sequence selected from:

(a) L1-L14 light chain variable domain sequences: SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, and SEQ ID NO: 164;

(b) H1-H14 heavy chain variable domain sequences: SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, and SEQ ID NO: 192 and (c) light chain variable domain sequence (a) and heavy chain variable domain sequence (b).

Preferably, combination (c) of light chain variable domain sequence (a) and heavy chain variable domain sequence (b) is selected from: L1H1, L2H2, L3H3, L4H4, L5H5, L6H6, L7H7, L8H8, L9H9, L10H10, L11H11, L12H12, L13H13, and L14H14.

Preferably, the antibody further comprises an amino acid sequence selected from:

(a) light chain constant region amino acid sequence: SEQ ID NO: 194;

(b) light chain constant region amino acid sequence: SEQ ID NO: 196;

(c) heavy chain constant region amino acid sequence: SEQ ID NO: 198;

(d) light chain constant region amino acid sequence: SEQ ID NO: 194 and heavy chain constant region amino acid sequence: SEQ ID NO: 198; and (e) light chain constant region amino acid sequence: SEQ ID NO: 196 and heavy chain constant region amino acid sequence of SEQ ID NO: 198;

Preferably, the antibody is selected from murine antibodies, human antibodies, humanized antibodies, chimeric antibodies, monoclonal antibodies, polyclonal antibodies, recombinant antibodies, antigen-binding antibody fragments, single-chain antibodies, double-chain antibodies, triple-chain antibodies, tetra-chain antibodies, Fab fragments, F(ab')x fragments, domain antibodies, IgD antibodies, IgE antibodies, IgM antibodies, IgG1 antibodies, IgG2 antibodies, IgG3 antibodies, and IgG4 antibodies.

Preferably, the antibody:
(a) has substantially the same $K_d$ as a reference antibody in binding to the human endothelin receptor;
(b) has substantially the same $IC_{50}$ as the reference antibody in inhibiting the activation of the human endothelin receptor; or (c) cross-competes with the reference antibody for binding to the human endothelin receptor.

Preferably, the reference antibody comprises a combination of a light chain variable domain sequence: SEQ ID NO: 138 and a heavy chain variable domain sequence: SEQ ID NO: 166.

Preferably, the antibody is a murine antibody or humanized antibody. When binding to a human endothelin receptor, the antibody:
(a) has an $IC_{50}$ of 500 nM or less in reducing the signal transduction of the human endothelin receptor;
(b) reduces pulmonary arterial hypertension in a rat or monkey pulmonary arterial hypertension model; or
(c) both (a) and (b).

A pharmaceutical composition comprises an antibody of the present invention that can be mixed with a pharmaceutically acceptable excipient.

Preferably, the antibody is a murine antibody or humanized antibody.

An isolated nucleic acid comprises a polynucleotide sequence encoding the light chain variable domain, the heavy chain variable domain, or both the light chain variable domain and the heavy chain variable domain of an antibody of the present invention.

Preferably, the polynucleotide sequence encoding the light chain variable domain of the antibody is selected from: SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, and SEQ ID NO: 163;
the polynucleotide sequence encoding the heavy chain variable domain of the antibody is selected from: SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, and SEQ ID NO: 191.

A recombinant expression vector comprises a nucleic acid of the present invention.

A host cell comprises a recombinant expression vector of the present invention.

A method for producing an antibody of the present invention, comprises culturing the host cells under the conditions that promotes the production of the antibody. A method of treating PAH in a human subject in need thereof comprises administering to the subject a therapeutically effective amount of the pharmaceutical composition of the present invention.

A kit for treating PAH, a disease associated with PAH, a disease associate with vascular smooth muscle, a disease associated with smooth muscle, sickle cell disease, cardiac inefficiency, heart failure, and a reproductive organ cancer, comprises the pharmaceutical composition of the present invention.

A pharmaceutical composition of the present invention is for use in the preparation of a medicament for treating PAH, a disease associated with PAH, a disease associate with vascular smooth muscle, a disease associated with smooth muscle, sickle cell disease, cardiac inefficiency, heart failure, and a reproductive organ cancer.

The present invention provides the following superior properties:
(a) The monoclonal antibody of the present invention has a high affinity and functional activity towards a human endothelin receptor.
(b) The antibody of the present invention is a new functional antibody against $ET_AR$. A humanized antibody of the murine antibody was obtained and ready for human therapeutic application.
(c) The antibody of the present invention is different from the existing small molecule drugs and offers the unique advantages of biological macromolecule drugs.

Therefore, the monoclonal antibody of the present invention with high affinity and specificity is valuable clinically.

BRIEF DESCRIPTION OF THE FIGURES

FIG. 1 shows the ELISA screening results of the supernatants of hybridomas for binding to CHO-DHFR-$ET_AR$ cells (labeled as CHO-$ET_AR$ in the figure), where anti-$ET_AR$ antibody A-1 was obtained from hybridoma clone 15F3.

DETAILED DESCRIPTION

Figure 2:
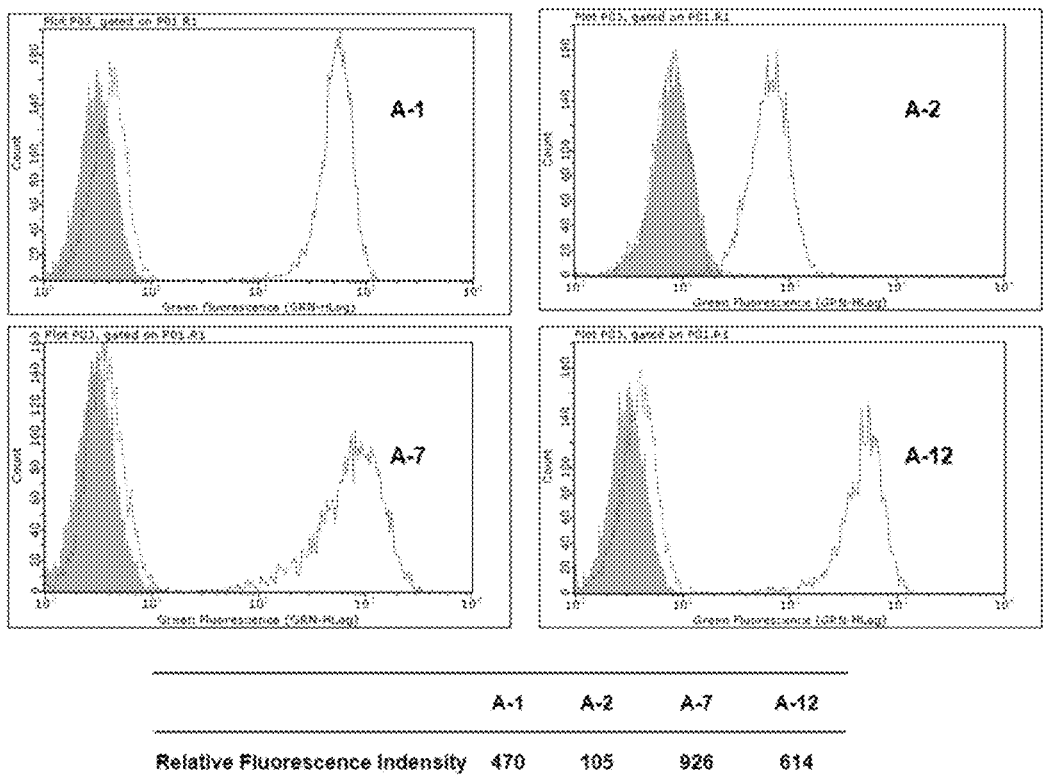
FIG. 2 shows the specific bindings of recombinant anti-$ET_AR$ antibodies (A-1, A-2, A-7, and A-12) to a human $ET_AR$ as determined by FACS, where the blue curves are the bindings of the anti-$ET_AR$ antibodies to CHO-DHFR- and the red curves are the bindings of the anti-$ET_AR$ antibodies to CHO-DHFR-$ET_AR$.

Through the following specific embodiments and examples in combination with figures, the present invention is further elaborated.

In this invention, unless specified otherwise, the raw materials and equipment are all available commercially or are commonly used. The methods described below, if not specified otherwise, are all conventional methods.

The present invention provides an antibody, for example, an antibody specifically binding to human $ET_AR$, including antibodies that inhibit or block the interaction between ET-1 and $ET_AR$, and downregulate the ET-1/$ET_AR$ single pathway. In one embodiment, the antibodies provided herein include an inhibitory murine antibody that can reduce the pulmonary artery pressure in a PAH animal model.

The present invention further provides a pharmaceutical composition, a kit, and a method, which comprise, contain, or employ an antibody that specifically binds to the human $ET_AR$. The present invention also provides a polynucleotide encoding the amino acid sequence of the antibody, or a fragment thereof; e.g., a polynucleotide encoding the complete amino acid sequence or a partial amino acid sequence of the antibody, a polynucleotide encoding the complete amino acid sequence or a partial amino acid sequence of a segment or a derivative of the antibody. Furthermore, the present invention provides a plasmid and a vector comprising such a polynucleotide; and a host cell line comprising such a plasmid and vector. The methods provided herein include, for example, preparation, purification, or characterization of the antibody that binds to the human $ET_AR$, such as a method for preparing an anti-$ET_AR$ antibody, a method for determining the binding of such an antibody to $ET_AR$, and a method for administering an antibody that binds to $ET_AR$ in an animal model.

Definitions

Polynucleotide and polypeptide sequences are described using standard one- or three-letter abbreviations. Unless otherwise specified, polypeptide sequences have their amino termini at the left and their carboxyl termini at the right, and single-stranded nucleic acid sequences and the top strands of double-stranded nucleic acid sequences have their 5' termini at the left and their 3' termini at the right. A particular section of a polypeptide can be designated by amino acid residue numbers such as amino acids 80 to 130, or in combination with the corresponding actual residues such as Lys80 to Lys130. A particular polypeptide or polynucleotide sequence also can be described by showing its differences from a reference sequence. Polynucleotide and polypeptide sequences of particular light and heavy chain variable domains may be expressed as L1 ("light chain variable domain 1") and H1 ("heavy chain variable domain 1"). An antibody comprising a light chain and heavy chain can be identified by combining the names of the light chain and heavy chain variable domains. For example, "L4H7" represents an antibody comprising light chain variable domain L4 and heavy chain variable domain H7.

Unless otherwise defined herein, scientific and technical terms used in the present invention shall have the meanings that are commonly understood by those of ordinary skill in the art. Further, unless otherwise required by context, singular terms shall include pluralities and plural terms shall include the singular. Generally, nomenclatures used herein in connection with, and techniques of, cell and tissue culture, molecular biology, immunology, microbiology, genetics and protein and nucleic acid chemistry and hybridization are those well-known and commonly used in the art. The methods and techniques of the present invention are generally performed according to conventional methods well-known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), each of which is incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

The following terms, unless otherwise specified, shall be understood to have the following meanings: The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also can be rendered substantially free of naturally associated components by isolation, using purification techniques well-known in the art. For example, the purity of a polypeptide sample can be assayed using polyacrylamide gel electrophoresis and staining of the gel to visualize the polypeptide using techniques well-known in the art. For certain purposes, higher resolution can be provided by using HPLC or other means well-known in the art for purification.

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxyl-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter susceptibility to form a protein complex, (4) alter binding affinities, and (4) confer or modify other physicochemical or functional properties. Analogs include muteins of a polypeptide. For example, single or multiple amino acid substitutions (e.g., conservative amino acid substitutions) can be made in the naturally occurring sequence (e.g., in the portion of the polypeptide outside the domain(s) forming intermolecular contacts). A "conservative amino acid substitution" is one that does not substantially change the structural characteristics of the parent sequence (e.g., replacement of an amino acid should not break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., 1991, Nature 354:105, each of which is incorporated herein by reference.

The present invention also provides non-peptide analogs of anti-$ET_AR$ antibodies. Non-peptide analogs are commonly used to provide drugs with properties analogous to those of the corresponding peptides. These types of non-peptide compounds are termed "peptide mimetics" or "peptidomimetics." Fauchere, 1986, *J. Adv. Drug Res.* 15:29-69; Veber and Preidinger, 1985, *Treads Neurosci.* 8:392-396; and Evans et al., 1987, *J. Med. Chem.* 30:1229-1239; each of which is incorporated herein by reference in its entirety. Peptide mimetics that are structurally similar to therapeutically useful peptides can be used to produce an equivalent therapeutic or prophylactic effect. Generally, a peptidomimetic is structurally similar to its corresponding polypeptide (i.e., a polypeptide with the desired biochemical properties or pharmacological parameters), such as a human antibody, but has one or more peptide linkages optionally replaced by a linkage selected from: —$CH_2NH$—, —$CH_2S$—, —$CH_2$—$CH_2$—, —CH=CH— (cis and trans), —$COCH_2$—, —CH(OH)$CH_2$—, and —$CH_2SO$— by the methods well-known in the art. Substitution of one or more amino acids or all of a peptide with a D-amino acid of the same type (e.g., D-lysine replacing L-lysine) may also be used to generate more stable peptides. In addition, methods known in the art can be applied (Rizo and Gierasch, 1992, *Ann. Rev. Biochem.* 61:387-418, which is incorporated herein by reference in its entirety), for example, by adding internal cysteine residues capable of forming intramolecular disulfide bridges which cyclize the peptide.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antibody" is a protein comprising a portion that binds to an antigen and optionally a scaffold or framework portion that allows the antibody to adopt a conformation that promotes the binding of the antibody to the antigen. Examples of antibodies include antibodies, antibody fragments (e.g., an antigen binding portion of an antibody), antibody derivatives, and antibody analogs. The antibody can comprise, for example, an alternative protein scaffold or artificial scaffold with grafted CDRs or CDRs derivatives. Such scaffolds include, but are not limited to, antibody-derived scaffolds comprising mutations introduced, for example, to stabilize the three-dimensional structure of the antibody as well as completely synthetic scaffolds comprising, for example, a biocompatible polymer. See, for example, Korndorfer et al., 2003, *Proteins: Structure, Function, and Bioinformatics*, 53:121-129; Roque et al., 2004, *Biotechnol. Prog.* 20:639-654. In addition, peptide antibody mimetics ("PAMs") can be used, as well as scaffolds based on antibody mimetics utilizing fibronectin components as a scaffold.

An antibody can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxyl terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, The heavy chain also includes a "D" region of about 10 more amino acids. See generally, Fundamental Immunology, Ch. 7 (Paul, W., ed., 2nd ed. Raven Press, N.Y. (1989)) (incorporated herein by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise regions FR1, CDR1, FR2, CDR2, FR3, CDR3 and FR4. The assignment of amino acids to each region is in accordance with the definitions of Kabat et al. in Sequences of Proteins of Immunological Interest, 5th Ed., US Dept. of Health and Human Services, PHS, NIH, NIH Publication No. 91-3242, 1991.

Unless otherwise specified, an "antibody" refers to an intact immunoglobulin or to an antigen binding portion thereof that competes with the intact antibody for specific binding. Antigen binding portions can be produced by recombinant DNA techniques or by enzymatic or chemical cleavage of intact antibodies. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, tribodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ regions; a F(ab')2 fragment is a bivalent fragment having two Fab fragments linked by a disulfide bridge at the hinge region; a Fd fragment has the $V_H$ and $C_{H1}$ regions; and a dAb fragment has a $V_H$ region, a $V_L$ region, or an antigen-binding fragment of a $V_H$ or $V_L$ region (U.S. Pat. Nos. 6,846,634, 6,6961,245, US App. Pub. Nos. 05/0202512, 04/0202995, 04/0038291, 04/0009507, 03/0039958, Ward et al., 1989, *Nature* 341:544-546).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ regions joined by a linker that is too short to allow for pairing between two regions on the same chain, thus allowing each region to pair with a complementary region on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and frame work regions (FR) of a given antibody can be identified using the system described by Kabat et al. in Sequences of Proteins of Immunological Interest, 5th Ed., US Dept. of Health and Human Services, PHS, NIH, NIH Publication no. 91-3242, 1991. One or more CDRs can be incorporated into a molecule either covalently or noncovalently to make it an antibody. An antibody can incorporate the CDR(s) as part of a larger polypeptide chain, can covalently link the CDR(s) to another polypeptide chain, or can incorporate the CDR(s) noncovalently. The CDRs permit the antibody to specifically bind to a particular antigen of interest.

An antibody can have one or more binding sites. If there are more than one binding sites, the binding sites can be identical to one another or can be different. For example, a naturally occurring human immunoglobulin typically has two identical binding sites, while a "bispecific" or "bifunctional" antibody has two different binding sites.

The term "murine antibody" includes all antibodies that have one or more variable and constant regions derived from a murine immunoglobulin sequence.

The term "humanized antibody" refers to an antibody that produced by grafting the complementarity determining region sequence of a murine antibody molecule into a human antibody variable region framework.

"Antigen-binding domain," "antigen-binding region," or "antibody-binding site" is a portion of an antibody that comprises amino acid residues (or other portion) interacting with an antigen and contributing to the specificity and affinity of the antibody for the antigen. For antibodies that specifically bind to their antigen, this will include at least a portion of at least one of its CDR regions.

An "epitope" is the portion of a molecule that is bound by an antibody (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antibody).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody of the invention, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps and without unpaired nucleotides at the 5' or the 3' end of either sequences. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vectors that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be an eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Endothelin Receptor

Endothelin A receptor ($ET_AR$) belongs to family A of 7-transmembrane receptors that are coupled to one or more intracellular signaling pathways via heterotrimeric guanine nucleotide-binding proteins (G proteins) (Jelinek et al., 1993, *Science* 259:1614-1616, Segre et al., 1993, *Trends Endocrinol. Metab.* 4:309-314). As used herein, "endothelin receptor" and "$ET_AR$" are used interchangeably.

In one embodiment, the antibody of the present invention can be selected to bind to membrane bound endothelin receptors as expressed on cells, and inhibit or block endothelin signaling through the endothelin receptors. In one embodiment, the antibody of the present invention specifically binds to the human endothelin receptor. In a further embodiment, the antibody binding to the human endothelin receptor can also bind to the endothelin receptors of other species, e.g., rat. The examples below provide one method of generating murine antibodies which bind to human membrane-bound endothelin receptors, and in a further embodiment, bind to endothelin receptors of other species.

The polynucleotide and polypeptide sequences for several species of the endothelin receptors are known. SEQ ID NO: 1-SEQ ID NO: 6 present sequences for human, monkey, and rat. The sequence data were obtained from the GeneBank database of the National Center for Biotechnology Information.

Endothelin A receptor
Human (*Homo sapiens*) polynucleotides (SEQ ID NO: 1)
Accession No. 563938.
Human (*Homo sapiens*) amino acid (SEQ ID NO: 2)
Accession No. AAB20278.
Cynomolgus (*Homo sapiens*) polynucleotides (SEQ ID NO: 3)
Accession No. JV635771.
Cynomolgus (*Homo sapiens*) amino acid (SEQ ID NO: 4)
Accession No. AFJ71111.
Rat (*Rattus norvegicus*) polynucleotides (SEQ ID NO: 5)
Accession No. M60786.
Rat (*Rattus norvegicus*) amino acid (SEQ ID NO: 6)
Accession No. AAA41114.

Antibodies

In one aspect, the present invention provides antibodies (e.g., antibodies, antibody fragments, antibody derivatives, antibody muteins, and antibody variants) that specifically bind to a human endothelin A receptor. In one embodiment the antibody is a murine antibody or a humanized antibody.

Antibodies in accordance with the present invention include antibodies that specifically bind to the human endothelin receptor and inhibit endothelin signaling through the endothelin receptor. In one embodiment, the $IC_{50}$ value of the antibody is 200 nM or less. In another aspect, the antibodies specifically bind the endothelin receptor, inhibit signaling, and exhibit therapeutic biological effects, such as lowering pulmonary hypertension in animal models. In one embodiment, the antibodies are murine antibodies that specifically bind the endothelin receptor, and inhibit signaling through the endothelin receptor. In another embodiment, the antibodies are murine antibodies that specifically bind to the endothelin receptor and inhibit signaling through the endothelin receptor, and can lower pulmonary hypertension.

In one embodiment, the antibody comprises a sequence that differs from a CDR sequence of one of A1-A14 listed in Table 1 below by 5, 4, 3, 2, 1, or 0 single amino acid addition(s), substitution(s), and/or deletion(s). As used herein, a CDR sequence that differs by no more than, for example, four amino acid additions, substitutions and/or deletions from a CDR sequence listed in Table 1 below refers to a sequence with 4, 3, 2, 1 or 0 single amino acid addition(s), substitution(s), and/or deletion(s) as compared with the sequence in Table 1.

In another embodiment, the antibody comprises one or more CDR consensus sequences shown below. Provided below are consensus sequences for light chain CDR1, CDR2, CDR3 and heavy chain CDR1, CDR2, and CDR3.

The light chain CDRs of antibodies A1/A14 and the heavy chain CDRs of exemplary antibodies A1/A14 are shown in Table 1. A-1 to A-14 correspond to L1 to L14 as well as H1 to H14 below. Also shown are polynucleotide sequences which encode the amino acid sequences of the CDRs.

In another aspect, the present invention provides antibodies that comprise a light chain variable region selected from the group consisting of L1-L14 or a heavy chain variable region selected from the group consisting of H1-H14, and fragments, derivatives, muteins, and variants thereof. Such an antibody can be designated using the nomenclature "LxHy", wherein "x" corresponds to the sequence number of the light chain variable region and "y" corresponds to the sequence number of the heavy chain variable region. For example, L2H1 refers to an antibody with a light chain variable region comprising the amino acid sequence of L2 and a heavy chain variable region comprising the amino acid sequence of H1 as shown in Table 2 below. Antibodies of the invention include, for example, antibodies having a combination of light chain and heavy chain variable regions selected from the combinations L1H1, L2H2, L3H3, L4H4, L5H5, L6H6, L7H7, L8H8, L9H9, L10H10, L11H11, L12H12, L13H13 and L14H14. In one embodiment, the antibodies are murine antibodies or humanized antibodies.

TABLE 1

| Ab | CDR1 | CDR2 | CDR3 |
|---|---|---|---|
| Light Chain L1-L12 | | | |
| A-1 Nucleic Acid | agggccagtcagaacattggcac aagcatacac (SEQ ID NO: 7) | tatgatctaagtctatatct (SEQ ID NO: 31) | caacatagttatagctggcc gtggacg (SEQ ID NO: 49) |
| Amino Acid | RASQNIGTSIH (SEQ ID NO: 8) | YASKSIS (SEQ ID NO: 32) | QHSYSWPWT (SEQ ID NO: 50) |
| A-2 Nucleic Acid | cgagcaagtgaaaatatttacagtt atttagca (SEQ ID NO: 9) | aatgcaaaaaccttagcagaa (SEQ ID NO: 33) | cagcatcattatggtattccgt tcacg (SEQ ID NO: 51) |

TABLE 1-continued

| Ab | CDR1 | CDR2 | CDR3 |
|---|---|---|---|
| Amino Acid | RASENIYSYLA (SEQ ID NO: 10) | NAKTLAE (SEQ ID NO: 34) | QHHYGIPFT (SEQ ID NO: 52) |
| A-3 Nucleic Acid | cagagcctcttgatattgatggaa agacatatttgaat (SEQ ID NO: 11) | ctggtgtctgaattggactct (SEQ ID NO: 35) | tggcaaggtacacattttccg ctcacg (SEQ ID NO: 53) |
| Amino Acid | QSLFDIDGKTYLN (SEQ ID NO: 12) | LVSELDS (SEQ ID NO: 36) | WQGTHFPLT (SEQ ID NO: 54) |
| A-4 Nuncleic Acid | cgggcaagtcaggacattggtgg tagcttaaac (SEQ ID NO: 13) | gccacatccagcttagattct (SEQ ID NO: 37) | ctacaatatgctagttctccgt atacg (SEQ ID NO: 55) |
| Amino Acid | RASQDIGGSLN (SEQ ID NO: 14) | ATSSLDS (SEQ ID NO: 38) | LQYASSPYT (SEQ ID NO: 56) |
| A-5 Nucleic Acid | agggccagccagactattagcga cttcttacac (SEQ ID NO: 15) | tatgatcccaatccatctct (SEQ ID NO: 39) | caaagtggtaacacctttccg tggacg (SEQ ID NO: 57) |
| Amino Acid | RASQTISDFLH (SEQ ID NO: 16) | YASQSIS (SEQ ID NO: 40) | QSGNTFPWT (SEQ ID NO: 58) |
| A-6 Nucleic Acid | agggcaagtgaggacatacacac tcaattagcc (SEQ ID NO: 17) | ggtgcagccagtttgaaaagt (SEQ ID NO: 41) | caacagtataggagtattcc gtggacg (SEQ ID NO: 59) |
| Amino Acid | RASEDIHTQLA (SEQ ID NO: 18) | GAASLKS (SEQ ID NO: 42) | QQYRSIPWT (SEQ ID NO: 60) |
| A-7 Nucleic Acid | agatctagtcagtacattgttcatag tactggaaccacctatttagaa (SEQ ID NO: 19) | aaagtttccaaccgatttct (SEQ ID NO: 43) | tttcaaggttcacattttccatt cacg (SEQ ID NO: 61) |
| Amino Acid | RSSQYIVHSTGTTYLE (SEQ ID NO: 20) | KVSNRFS (SEQ ID NO: 44) | FQGSHFPFT (SEQ ID NO: 62) |
| A-8 Nucleic Acid | agatctagtcattaccttgttcatga taacggaaacacctatgttgaa (SEQ ID NO: 21) | aaggtttccaaccgatttct (SEQ ID NO: 43) | tttcaaggttcacatttcccatt cacg (SEQ ID NO: 63) |
| Amino Acid | RSSHYLVHDNGNTYVE (SEQ ID NO: 22) | KVSNRFS (SEQ ID NO: 44) | FQGSHFPFT (SEQ ID NO: 62) |
| A-9 Nucleic Acid | agatctagtcagaacattgtccata gtactggaaacacctatttagaa (SEQ ID NO: 23) | aaagtttccaaccgatttct (SEQ ID NO: 43) | tttcaaggttcacattttccatt cacg (SEQ ID NO: 61) |
| Amino Acid | RSSQNIVHSTGNTYLE (SEQ ID NO: 24) | KVSNRFS (SEQ ID NO: 44) | FQGSHFPFT (SEQ ID NO: 62) |
| A-10 Nucleic Acid | agtgtcagctcaagtgtaagttaca tacac (SEQ ID NO: 25) | gacacatccaaactggcttct (SEQ ID NO: 45) | caccagtggagtactaaccc acccacg (SEQ ID NO: 63) |
| Amino Acid | SVSSSVSYIH (SEQ ID NO: 26) | DTSKLAS (SEQ ID NO: 46) | HQWSTNPPT (SEQ ID NO: 64) |
| A-11 Nucleic Acid | agtgccagctcaagtgtaagttac atgtgc (SEQ ID NO: 27) | gacacatccaaactggcttct (SEQ ID NO: 45) | cagcagtggagtagtaaccc acccacg (SEQ ID NO: 65) |
| Amino Acid | SASSSVSYMC (SEQ ID NO: 28) | DTSKLAS (SEQ ID NO: 46) | QQWSSNPPT (SEQ ID NO: 66) |
| A-12 Nucleic Acid | cagggcattaacaattat (SEQ ID NO: 29) | tatacatcaactttacagtca (SEQ ID NO: 47) | cagcagtttagtaaacttcgg aca (SEQ ID NO: 67) |
| Amino Acid | QGINNY (SEQ ID NO: 30) | YTSTLQS (SEQ ID NO: 48) | QQFSKLRT (SEQ ID NO: 68) |

TABLE 1-continued

| Ab | CDR1 | CDR2 | CDR3 |
|---|---|---|---|
| Heavy Chain H1-H12 | | | |
| A-1 Nucleic Acid | gggttctcactgaccacttct ggcttgggtgttgcc (SEQ ID NO: 69) | cacatttggtcggatggtgac acgcgctattacccagccctg aagaac (SEQ ID NO: 91) | atgaaggatgatagtctttactttga caac (SEQ ID NO: 115) |
| Amino Acid | GFSLTTSGLGVA (SEQ ID NO: 70) | HIWSDGDTRYYPA LKN (SEQ ID NO: 92) | MKDDSLYFDN (SEQ ID NO: 116) |
| A-2 Nucleic Acid | ggctacacctttactagctac tggatacac (SEQ ID NO: 71) | tacattaatcctgacactgatta tagtgagtacaat (SEQ ID NO: 93) | gcaagtgctggttattattMttgac ttc (SEQ ID NO: 117) |
| Amino Acid | GYTFTSYWIH (SEQ ID NO: 72) | YINPDTDYSEYN (SEQ ID NO: 94) | ASAGYYFFDF (SEQ ID NO: 118 |
| A-3 Nucleic Acid | ggcctcaacattaaagacat ctatattcac (SEQ ID NO: 73) | aggattgatcctgcgaacggt aagactgcatatgac (SEQ ID NO: 95) | ggtaggggggcccac (SEQ ID NO: 119) |
| Amino Acid | GLNIKDIYIH (SEQ ID NO: 74) | RIDPANGKTAYD (SEQ ID NO: 96) | GRGAH (SEQ ID NO: 120) |
| A-4 Nucleic Acid | ggttactcattcaccaactac tggatacac (SEQ ID NO: 75) | atgattgatccttccgatgctg aaactgggttaaat (SEQ ID NO: 97) | gcaagaattggcgattactataata tggactac (SEQ ID NO: 121) |
| Amino Acid | GYSFTNYWIH (SEQ ID NO: 76) | MIDPSDAETGLN (SEQ ID NO: 98) | ARIGDYYNMDY (SEQ ID NO: 122) |
| A-5 Nucleic Acid | ggattcactttcagtgactat cccatgtct (SEQ ID NO: 77) | gttagtgatggtggtggttcca cc (SEQ ID NO: 99) | acaagacatgcttcctactatagct acgaccattctatggactac (SEQ ID NO: 123) |
| Amino Acid | GFTFSDYPMS (SEQ ID NO: 78) | VSDGGGST (SEQ ID NO: 100) | TRHASYYSYDHSMD Y (SEQ ID NO: 124) |
| A-6 Nucleic Acid | ggattcactttcagtagcttt ggcatgtct (SEQ ID NO: 79) | attagtagtgctggtagtttcac c (SEQ ID NO: 101) | gcaagacgggggtacgacgttgg gtgctttgaccac (SEQ ID NO: 125) |
| Amino Acid | GFTFSSFGMS (SEQ ID NO: 80) | ISSAGSFT (SEQ ID NO: 102) | ARRGYDVGCFDH (SEQ ID NO: 126) |
| A-7 Nucleic Acid | ggattcactttcagtacctat ggcatgtct (SEQ ID NO: 81) | accattaatactaatggtggta ccacctattatcgagacagtgt gaagggc (SEQ ID NO: 103) | gcaagagactacggggctatgga ctac (SEQ ID NO: 127) |
| Amino Acid | GFTFSTYGMS (SEQ ID NO: 82) | TINTNGGTTYYRDS VKG (SEQ ID NO: 104) | ARDYGAMDY (SEQ ID NO: 128) |
| A-8 Nucleic Acid | ggattcactttcagtacctat ggcatgtct (SEQ ID NO: 81) | accataaatactaatggtggta acacctattattcagacaatgt gaagggc (SEQ ID NO: 105) | gcaagagactacggggctatgga ctac (SEQ ID NO: 127) |
| Amino Acid | GFTFSTYGMS (SEQ ID NO: 82) | TINTNGGNTYYSD NVKG (SEQ ID NO: 106) | ARDYGAMDY (SEQ ID NO: 128) |
| A-9 Nucleic Acid | ggattcactttcagtagttat ggcatgtct (SEQ ID NO: 83) | accattagtactaatggtgcca ccgccaattatccagacagtg tgaagggc (SEQ ID NO: 107) | gcaactgaaaagggagctatggg ctac (SEQ ID NO: 129) |
| Amino Acid | GFTFSSYGMS (SEQ ID NO: 84) | TISTNGATANYPDS VKG (SEQ ID NO: 108) | ATEKGAMGY (SEQ ID NO: 130) |
| A-10 Nucleic Acid | gggttttcactgaccacttct ggtatgggtgtaggc (SEQ ID NO: 85) | cacatttggtgggatgatgata agtactataatccatccctgaa gagc (SEQ ID NO: 109) | gctcgaagaactgagactatgatt acgacagtgctatattactatgctat ggactac (SEQ ID NO: 131) |

TABLE 1-continued

| Ab | CDR1 | CDR2 | CDR3 |
|---|---|---|---|
| Amino Acid | GFSLTTSGMGVG (SEQ ID NO: 86) | HIWWDDDKYYNPS LKS (SEQ ID NO: 110) | ARRTETMITTVLYYY AMDY (SEQ ID NO: 132) |
| A-11 Nucleic Acid | ggattttcactgagcacttct ggtttgggtgtaggc (SEQ ID NO: 87) | cacatttggtgggatgatgata agtactataatccatcccttaa gaga (SEQ ID NO: 111) | gctcgaaggagggaagttaacttc ggtattaactattactattctatgga ctac (SEQ ID NO: 133) |
| Amino Acid | GFSLSTSGLGVG (SEQ ID NO: 88) | HIWWDDDKYYNPS LKR (SEQ ID NO: 112) | ARRREVNFGINYYYS MDY (SEQ ID NO: 134) |
| A-12 Nucleic Acid | ggattcaccttcagtgattatt ac (SEQ ID NO: 89) | attagaaatcgggctaatggtt acacaaca (SEQ ID NO: 113) | gtaagagattcctatcactacgggt actttcgatgtc (SEQ ID NO: 135) |
| Amino Acid | GFTFSDYY (SEQ ID NO: 90) | IRNRANGYTT (SEQ ID NO: 114) | VRDSYHYGYFDV (SEQ ID NO: 136) |

Table 2 provides polynucleotide (DNA) sequences encoding the amino acid sequences of the variable light and variable heavy domains of exemplary $ET_AR$ antibodies. (SEQ ID NO: 137-192).

Polynucleotide and Amino Acid Sequences of Light Chain Variable Domains:

L1 (A-1): polynucleotide sequence SEQ ID NO: 137, amino acid sequence SEQ ID NO: 138.
L2 (A-2): polynucleotide sequence SEQ ID NO: 139, amino acid sequence SEQ ID NO: 140.
L3 (A-3): polynucleotide sequence SEQ ID NO: 141, amino acid sequence SEQ ID NO: 142.
L4 (A-4): polynucleotide sequence SEQ ID NO: 143, amino acid sequence SEQ ID NO: 144.
L5 (A-5): polynucleotide sequence SEQ ID NO: 145, amino acid sequence SEQ ID NO: 146.
L6 (A-6): polynucleotide sequence SEQ ID NO: 147, amino acid sequence SEQ ID NO: 148.
L7 (A-7): polynucleotide sequence SEQ ID NO: 149, amino acid sequence SEQ ID NO: 150.
L8 (A-8): polynucleotide sequence SEQ ID NO: 151, amino acid sequence SEQ ID NO: 152.
L9 (A-9): polynucleotide sequence SEQ ID NO: 153, amino acid sequence SEQ ID NO: 154.
L10 (A-10): polynucleotide sequence SEQ ID NO: 155, amino acid sequence SEQ ID NO: 156.
L11 (A-11): polynucleotide sequence SEQ ID NO: 157, amino acid sequence SEQ ID NO: 158.
L12 (A-12): polynucleotide sequence SEQ ID NO: 159, amino acid sequence SEQ ID NO: 160.
L13 (A-13): polynucleotide sequence SEQ ID NO: 161, amino acid sequence SEQ ID NO: 162.
L14 (A-14): polynucleotide sequence SEQ ID NO: 163, amino acid sequence SEQ ID NO: 164.

Polynucleotide and Amino Acid Sequences of Heavy Chain Variable Domains:

H1 (A-1): polynucleotide sequence SEQ ID NO: 165, amino acid sequence SEQ ID NO: 166.
H2 (A-2): polynucleotide sequence SEQ ID NO: 167, amino acid sequence SEQ ID NO: 168.
H3 (A-3): polynucleotide sequence SEQ ID NO: 169, amino acid sequence SEQ ID NO: 170.
H4 (A-4): polynucleotide sequence SEQ ID NO: 171, amino acid sequence SEQ ID NO: 172.
H5 (A-5): polynucleotide sequence SEQ ID NO: 173, amino acid sequence SEQ ID NO: 174.
H6 (A-6): polynucleotide sequence SEQ ID NO: 175, amino acid sequence SEQ ID NO: 176.
H7 (A-7): polynucleotide sequence SEQ ID NO: 177, amino acid sequence SEQ ID NO: 178.
H8 (A-8): polynucleotide sequence SEQ ID NO: 179, amino acid sequence SEQ ID NO: 180.
H9 (A-9): polynucleotide sequence SEQ ID NO: 181, amino acid sequence SEQ ID NO: 182.
H10 (A-10): polynucleotide sequence SEQ ID NO: 183, amino acid sequence SEQ ID NO: 184.
H11 (A-11): polynucleotide sequence SEQ ID NO: 185, amino acid sequence SEQ ID NO: 186.
H12 (A-12): polynucleotide sequence SEQ ID NO: 187, amino acid sequence SEQ ID NO: 188.
H13 (A-13): polynucleotide sequence SEQ ID NO: 189, amino acid sequence SEQ ID NO: 190.
H14 (A-14): polynucleotide sequence SEQ ID NO: 191, amino acid sequence SEQ ID NO: 192.

Particular embodiments of antibodies of the present invention comprise one or more amino acid sequences that are identical to the amino acid sequences of the CDRs and/or FRS (framework regions) illustrated above. In one embodiment, the antibody comprises a light chain CDR1 sequence illustrated above. In another embodiment, the antibody comprises a light chain CDR2 sequence illustrated above. In another embodiment, the antibody comprises a light chain CDR3 sequence illustrated above. In another embodiment, the antibody comprises a heavy chain CDR1 sequence illustrated above. In another embodiment, the antibody comprises a heavy chain CDR2 sequence illustrated above. In another embodiment, the antibody comprises a heavy chain CDR3 sequence illustrated above. In another embodiment, the antibody comprises a light chain FR1 sequence illustrated above. In another embodiment, the antibody comprises a light chain FR2 sequence illustrated above. In another embodiment, the antibody comprises a light chain FR3 sequence illustrated above. In another embodiment, the antibody comprises a light chain FR4 sequence illustrated above. In another embodiment, the antibody comprises a heavy chain FR1 sequence illustrated above. In another embodiment, the antibody comprises a heavy chain FR2 sequence illustrated above. In another embodiment, the antibody comprises a heavy chain FR3 sequence illustrated above. In another embodiment, the antibody comprises a heavy chain FR4 sequence illustrated above.

In another embodiment, a CDR3 sequence of the antibody differs from a CDR3 sequence of A-1 by no more than 6, 5, 4, 3, 2, 1 or 0 single amino acid addition(s), substitution(s), and/or deletion(s). In another embodiment, a light chain CDR3 sequence of the antibody differs from the light chain CDR3 sequence of A-1 described above by no more than 6, 5, 4, 3, 2, 1 or 0 single amino acid addition(s), substitution(s), and/or deletion(s) and the heavy chain CDR3 sequence of the antibody differs from a heavy chain CDR3 sequence of A-1/A-2 described above by no more than 6, 5, 4, 3, 2, 1 or 0 single amino acid addition(s), substitution(s), and/or deletion(s). In another embodiment, the antibody further comprises 1, 2, 3, 4, or 5 CDR sequences, each of which independently differs from a CDR sequence of A-1 by 6, 5, 4, 3, 2, 1, or 0 single amino acid addition(s), substitution(s), and/or deletion(s). In another embodiment, the antibody comprises the CDRs of a light chain variable domain and the CDRs of a heavy chain variable domain set forth above. In another embodiment, the antibody comprises 1, 2, 3, 4, 5, and/or 6 consensus CDR sequence(s) shown above. In one embodiment, the antibody is a murine antibody.

In one embodiment, the antibody (such as an antibody or antibody fragment) comprises an amino acid sequence of a light chain variable domain that differs from the sequence of light chain variable domain L1 by 15, 14, 13, 12, 11, 10, 9, 8, 7, 6, 5, 4, 3, 2, 1 or 0 single amino acid deletion(s), insertion(s), or substitution(s). In another embodiment, the light-chain variable domain comprises an amino acid sequence that is at least 70%, 75%, 80%, 85%, 90%, 95%, 97% or 99% identical to the sequence of light chain variable domain L1. In another embodiment, the light chain variable domain comprises an amino acid sequence that is encoded by a nucleotide sequence that is at least 70%, 75%, 80%, 85%, 90%, 95%, 97% or 99% identical to the L1 polynucleotide sequence listed above. In another embodiment, the light chain variable domain comprises an amino acid sequence encoded by a polynucleotide that hybridizes under moderately stringent conditions to the complement of a polynucleotide encoding light chain variable domain L1. In another embodiment, the light chain variable domain comprises an amino acid sequence encoded by a polynucleotide that hybridizes under stringent conditions to the complement of a polynucleotide encoding light chain variable domain L1.

In another embodiment, the present invention provides an antibody comprising a heavy chain variable domain that comprises an amino acid sequence that differs from the sequence of heavy chain variable domain H1 by 15, 14, 13, 12, 11, 10, 9, 8, 7, 6, 5, 4, 3, 2, 1 or 0 single amino acid deletion(s), insertion(s), or substitution(s). In another embodiment, the heavy chain variable domain comprises an amino acid sequence that is at least 70%, 75%, 80%, 85%, 90%, 95%, 97%, or 99% identical to the sequence of heavy chain variable domain H1. In another embodiment, the heavy chain variable domain comprises an amino acid sequence encoded by a polynucleotide that hybridizes under moderately stringent conditions to the complement of a polynucleotide encoding heavy chain variable domain H1. In another embodiment, the heavy chain variable domain comprises an amino sequence encoded by a polynucleotide that hybridizes under stringent conditions to the complement of a polynucleotide encoding heavy chain variable domain H1.

Antibodies (e.g., antibodies, antibody fragments, and antibody derivatives) of the invention can comprise any constant region known in the art. The light chain constant region can be, for example, a kappa- or lambda-type light chain constant region, e.g., a murine kappa- or lambda-type light chain constant region. The heavy chain constant region can be, for example, an alpha-, delta-, epsilon-, gamma-, or mu-type heavy chain constant regions, e.g., a murine alpha-, delta-, epsilon-, gamma-, or mu-type heavy chain constant region. In one embodiment, the light or heavy chain constant region is a fragment, derivative, variant, or mutein of a naturally occurring constant region.

Subclass switching techniques are known to derive an antibody of a different subclass or isotype. Thus, IgG antibodies can be derived from an IgM antibody, for example, and vice versa. Such techniques allow the preparation of new antibodies that possess the antigen-binding properties of a given antibody (the parent antibody), but also exhibit biological properties associated with an isotype or subclass different from that of the parent antibody. Recombinant DNA techniques can be employed. Cloned DNA encoding particular antibody polypeptides can be employed, e.g., DNA encoding the constant region of an antibody of the desired isotype. See also Lanitto et al., 2002, *Methods Mol. Biol.* 178:303-16.

In one embodiment, an antibody of the invention further comprises a constant light chain κ or λ region or a fragment thereof. Sequences of light chain constant regions and their coding polynucleotides are provided below.
Light Chain Constant Region:
polynucleotide (κ), (SEQ ID NO: 193)
amino acid (κ), (SEQ ID NO: 194)
polynucleotide (λ), (SEQ ID NO: 195)
amino acid (λ), (SEQ ID NO: 196)

In another embodiment, an antibody of the invention further comprises a heavy chain constant region or a fragment thereof as shown below.
Heavy Chain Constant Region:
Polynucleotide (IgG1), (SEQ ID NO: 197)
amino acid (IgG1), (SEQ ID NO: 198)

The antibodies of the present invention include those comprising, for example, combination L1H1, L2H2, L3H3, L4H4, L5H5, L6H6, L7H7, L8H8, L9H9, L10H10, L11H11, L12H12, L13H13 or L14H14; or an isotype thereof (for example, IgA, IgG1, IgG2a, IgG2b, IgG3, IgM, IgE, or IgD) or a Fab or F(ab')2 fragment thereof.

Antibodies and Antibody Fragments

In one embodiment, the antibody is an antibody. The term "antibody" refers to an intact antibody or an antigen binding fragment thereof, as described generally in the definition section. An antibody can comprise a complete antibody molecule (including polyclonal, monoclonal, chimeric, humanized, or human versions having full length heavy and/or light chains), or comprise an antigen binding fragment thereof. Antibody fragments include F(ab')2, Fab, Fab', Fv, Fc, and Fd fragments, and can be incorporated into single domain antibodies, single-chain antibodies, maxibodies, minibodies, intrabodies, diabodies, tribadies, tetrabodies, v-NAR and bis-scFv (see e.g., Hollinger and Hudson, 2005, *Nature Biotechnology*, 23, 9, 1126-1136). Also included are antibody polypeptides such as those disclosed in U.S. Pat. No. 6,703,199, including fibronectin polypeptide monobodies. Other antibody polypeptides are disclosed in U.S. Patent Publication 2005/0238646, which are single-chain polypeptides. In one embodiment, the antibodies of the present invention comprise at least one CDR or consensus CDR as set forth in Table 2 above.

In one embodiment, the variable regions of a gene expressing a monoclonal antibody of interest are amplified using nucleotide primers in a hybridoma. These primers can be synthesized by one of ordinary skill in the art, or can be purchased from commercially available sources (see, e.g., Stratagene, La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers can be used to amplify heavy or light chain variable regions, which can then be inserted into vectors such as ImmunoZAP™ H or ImmunoZAP™ L (Stratagene), respectively. These vectors can then be introduced into *E. coli*, yeast, or mammalian-based systems for expression. Large amounts of a single-chain protein containing a fusion of the $V_H$ and $V_L$ regions can be produced using these methods (see Bird el al., 1988, *Science* 242:423-426).

Once antibody-producing cells of the instant invention have been obtained using any above-described immunization and other techniques, the genes of the specific antibodies can be cloned by isolating and amplifying DNA or mRNA therefrom according to standard procedures described herein. The antibodies produced therefrom can be sequenced to identify CDRs, and the coding DNA of the CDRs can be manipulated as described above to generate other antibodies of the present invention.

Antibodies of the present invention preferably modulate endothelin signaling in the cell-based assay described herein and/or in the in vivo assay described herein and/or cross-block the binding of one of the antibodies described herein and/or are cross-blocked from binding $ET_AR$ by one of the antibodies described herein. Accordingly, such binding agents can be identified using the assays described herein.

In certain embodiments, antibodies are generated by first identifying antibodies that bind to cells overexpressing $ET_AR$ and/or neutralize in the cell-based and/or in vivo assays described herein and/or cross-block the antibodies described herein and/or are cross-blocked from binding $ET_AR$ by one of the antibodies described herein.

It should be understood by one skilled in the art that certain proteins, such as antibodies, can undergo a variety of post-translational modifications. The types and extents of these modifications often depend on the host cell lines used to express the protein as well as the culture conditions. Such modifications can include variations in glycosylation, methionine oxidation, diketopiperizine formation, aspartate isomerization and asparagine deamidation. A frequent modification is the loss of a carboxyl-terminal basic residue (such as lysine or arginine) due to the action of carboxypeptidases (as described in Harris, R. J., 1995, *Journal of Chromatography* 705:129-134).

An alternative method for production of a murine monoclonal antibody is to inject hybridoma cells into the peritoneal cavity of a syngeneic mouse, for example, a mouse that has been treated (e.g., pristine-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, e.g., Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). A monoclonal antibody can be purified by affinity chromatography using an appropriate ligand selected based on particular properties of the antibody (e.g., heavy or light chain isotype, binding specificity, etc.). Examples of suitable ligands immobilized on a solid support include Protein A, Protein G, an anti-constant region (light chain or heavy chain) antibody, an anti-idiotype antibody, and a TGF-β binding protein, or a fragment or variant thereof.

Molecular evolution of the complementarity determining regions (CDRs) in the center of the antibody binding site also has been used to isolate antibodies with increased affinities, for example, antibodies having increased affinities for c-erbB-2, as described by Schier et al., 1996, *J. Mol. Biol.* 263:551-567 Accordingly, such techniques are useful in preparing antibodies to human endothelin A receptor.

Antibodies against human endothelin A receptor can be used, for example, in assays to detect the presence of the endothelin A receptor, either in vitro or in vivo.

Antibodies can also be prepared by any of the conventional techniques. For example, they can be purified from cells that naturally express them (e.g., an antibody can be purified from a hybridoma that produces it) or produced in recombinant expression systems using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y, (1988). This is discussed in the nucleic acid section below.

Antibodies can be prepared and screened for desired properties by any known techniques. Some techniques relate to the isolation of nucleic acids encoding polypeptide chains (or portions thereof) of related antibodies (e.g., anti-$ET_AR$ antibodies) and manipulation of nucleic acid. Nucleic acids can be fused with another relevant nucleic acid or modified by recombinant DNA techniques (e.g., induced mutations or other conventional techniques) to add, delete or replace one or more amino acid residues.

Where it is desired to improve the affinity of antibodies according to the invention containing one or more of the above-mentioned CDRs, such antibodies can be obtained by a number of affinity maturation protocols, including maintaining the CDRs (Yang et al., 1995, *J. Mol. Biol.*, 254:392-403), chain shuffling (Marks et al., 1992, *Bio/Technology*, 10:779-783), use of mutation strains of *E. coli*. (Low et al., 1996, *J. Mol. Biol.*, 250:350-368), DNA shuffling (Patten et al., 1997, *Curr. Opin. Biotechnol.*, 8:724-733), phage display (Thompson et al., 1996, *J. Mol. Biol.*, 256:7-88) and additional PCR techniques (Crameri et al., 1998, *Nature*, 391:288-291). These methods or affinity maturation are discussed in Vaughan et al., 1998, *Nature Biotechnology*, 16:535-539).

Antibody Fragments

In another aspect, the present invention provides fragments of an anti-$ET_AR$ antibody of the invention. Such fragments can comprises entirely antibody-derived sequences or additional sequences. Examples of antigen binding fragments include Fab, F(ab')2, single chain antibodies, diabodies, tribodies, tetrabodies, and domain antibodies. Other examples are provided in Lunde et al., 2002, *Biochem. Soc. Trans.* 30:500-06.

Single chain antibodies can be formed by linking heavy and light chain variable domain (Fv region) fragments via an amino acid bridge (short peptide linker), resulting in a single polypeptide chain. Such single-chain Fvs (scFvs) have been prepared by fusion DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, multimeric scFvs that bind to different epitopes can be formed (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544; de Graaf et al., 2002, *Methods Mol. Biol.* 178:379-87. Single chain antibodies derived from antibodies provided herein including, but not limited to, scFvs comprising the variable domain combination L1H1, are encompassed by the present invention.

Antibodies derived from an antibody can also be obtained, for example, by proteolytic hydrolysis of the antibody, for example, pepsin or papain digestion of a whole antibody according to conventional methods. By way of example, antibody fragments can be produced by enzymatic cleavage of antibodies with pepsin to provide a 5S fragment termed F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoffet et al., 1960, *Arch. Biochem. Biophys.* 89:230; Porter, 1959, *Biochem. J.* 73:119; Edelman et al., Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques can also be used, so long as the fragments bind to the antigen that is recognized by the intact antibody.

Another form of an antibody fragment is a peptide comprising one or more complementarity determining regions (CDRs) of an antibody. CDRs can be obtained by constructing polynucleotides that encode the CDRs. Such polynucleotides are prepared, for example, by using the polymerase chain reaction to synthesize the variable region using mRNA or antibody-producing cells as a template (see, for example, Larrick et al., 1991, Methods: A Companion to Methods in Enzymology 2:106; Courtenay-Luck, "(Genetic Manipulation of Monoclonal Antibodies," in Monoclonal Antibodies: Production, Engineering and Clinical Application, Ritter et al. (eds.), page 166 (Cambridge University Press 1995); and Ward el al., "Genetic Manipulation and Expression or Antibodies," in Monoclonal Antibodies: Principles and Applications, Birch et al., (eds.), page 137 (Wiley-Liss, Inc. 1995). The antibody fragment further can comprise at least one variable region domain of an antibody described herein. Thus, for example, the V region domain can be monomeric and be a $V_H$ or $V_L$ domain, which can bind to $ET_AR$ with an affinity of $10^{-7}$ M or less as described below.

The variable region domain can be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain can be covalently attached at a C-terminal amino acid to at least one other antibody domain or a fragment thereof. Thus, for example, a $V_H$ domain that is present in the variable region domain can be linked to an immunoglobulin $C_{H1}$ domain or a fragment thereof. Similarly, a $V_L$ domain can be linked to a $C_K$ domain or a fragment thereof. In this way, for example, the antibody can be a Fab fragment, wherein the antigen binding domain contains associated $V_H$ and $V_L$ domains covalently linked at their C-termini to a $C_{H1}$ nd $C_K$ domain, respectively. The $C_{H1}$ domain can be extended with further amino acids, for example to provide a hinge region or a portion of a hinge region domain as found in a Fab' fragment, or to provide further domains, such as antibody $C_{H2}$ and $C_{H3}$ domains.

Derivatives and Variants of Antibodies

The nucleotide sequences of L1 and H1, encoding the corresponding amino acid sequences of A1/A2, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, *Gene* 42:133; Bauer et al., 1985, *Gene* 37:73; Craik, 1985, *BioTechniques,* 3:12-19; Smith et al., 1981, Genetic Engineering: Principles and Methods, Plenum Press; and U.S. Pat. Nos. 4,518,584 and 4,737,462. These and other methods can be used to make, for example, derivatives of anti-endothelin A receptor antibodies that have a desired property, for example, an increase in affinity, avidity, or specificity for an endothelin receptor or in vivo or in vitro stability, or reduced in vivo side-effects as compared to the underivatized antibody.

Other derivatives of anti-endothelin receptor antibodies within the scope or this invention include covalent or aggregative conjugates or anti-endothelin receptor antibodies, or fragments thereof, with other proteins or polypeptides, such as by expression or recombinant fusion proteins comprising heterologous polypeptides fused to the N-terminus or C-terminus or an anti-endothelin receptor antibody polypeptide. For example, the conjugated peptide can be a heterologous signal (or leader) polypeptide, e.g., the yeast alpha-factor leader or a peptide such as an epitope tag. An antibody containing fusion proteins can comprise peptides added to facilitate purification or identification of antigen binding protein (e.g., poly-His). An antibody also can be linked to the FLAG peptide as described in Hopp et al., 1988, *Bio/Technology* 6:1204, and U.S. Pat. No. 5,011,912. The FLAG peptide is highly antigenic and provides an epitope reversibly bound by a specific monoclonal antibody (mAb), enabling rapid assay and facile purification of an expressed recombinant protein. Reagents useful for preparing fusion proteins in which the FLAG peptide is fused to a given polypeptide are commercially available (Sigma, St. Louis, Mo.). In another embodiment, oligomers that contain one or more antibodies can be employed as endothelin receptor antagonists. Oligomers can be in the form of covalently-linked or non-covalently-linked dimers, trimers, or higher oligomers. Oligomers comprising two or more antibodies are contemplated for use, with one example being a homodimer. Other oligomers include heterodimers, homotrimers, heterotrimers, homotetramers, heterotetramers, etc.

One embodiment is directed to oligomers comprising multiple antibodies joined via covalent or non-covalent interactions between peptide moieties fused to the antibodies. Such peptides can be peptide linkers (spacers), or peptides that have the property of promoting oligomerization. Leucine zippers and certain polypeptides derived from antibodies are among the peptides that can promote oligomerization of antibodies attached thereto, as described in more detail below.

In particular embodiments, the oligomers comprise from two to four antibodies. The antibodies of the oligomer can be in any form, such as any of the forms described above, e.g., variants or fragments. Preferably, the oligomers comprise antibodies that have endothelin receptor binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *PNAS USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11. One embodiment of the present invention is directed to a dimer comprising two fusion proteins created by fusing an endothelin receptor binding fragment of an anti-endothelin A receptor antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon inter-chain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. In other embodiments, the variable portion of the heavy and/or light chains of an anti-endothelin receptor antibody can be substituted for the variable portion of an antibody heavy and/or light chain.

Alternatively, the oligomer is a fusion protein comprising multiple antibodies, with or without peptide linkers (spacer peptides). Among the suitable peptide linkers are those described in U.S. Pat. Nos. 4,751,180 and 4,935,233.

Another method for preparing oligomeric antibodies involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-78. In one method, recombinant fusion proteins comprising an anti-endothelin receptor antibody fragment or derivative fused to a leucine zipper peptide are expressed in suitable host cells, and the soluble oligomeric anti-endothelin receptor antibody fragments or derivatives that form are recovered from the culture supernatant.

In another embodiment, the antibody derivatives can comprise at least one of the CDRs disclosed herein. For example, one or more CDR can be incorporated into known antibody framework regions (IgG1, IgG2, etc.), or conjugated to a suitable vehicle to enhance the half-life thereof. Suitable vehicles include, but are not limited to Fc, albumin, transferrin, and the like. These and other suitable vehicles are known in the art. Such conjugated CDR peptides can be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody of the present invention can have at least one amino acid substitution, providing that the antibody retains binding specificity. Therefore, modifications to the antibody structures are encompassed within the scope of the invention. These can include amino acid substitutions, which may be conservative or non-conservative, that do not destroy the human endothelin receptor binding capability of an antibody. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution can also involve a substitution of a native amino acid residue with a normative residue such that there is little or no effect on the polarity or charge of the amino acid residue at that position. Non-conservative substitutions can involve the exchange of a member of one class of amino acids or amino acid mimetics for a member from another class with different physical properties (e.g., size, polarity, hydrophobicity, charge).

Moreover, one skilled in the art may generate variants to be tested, which contain a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure. Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. A number of scientific publications have been devoted to the prediction of secondary structure. See Moult, 1996, *Curr. Op. Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276 and Chou et al., *Biophys. J.* 26:367-384. Moreover, computer programs are currently available to assist with predicting secondary structure. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within the structure of a polypeptide or protein. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (see Holm, supra (1999), and Brenner, supra (1997)). In certain embodiments, variants of antibodies include glycosylation variants, wherein the number and/or type of glycosylation sites have been altered compared to the amino acid sequences of a parent polypeptide. In certain embodiments, variants comprise a greater or lesser number of N-linked glycosylation sites than the native protein. Alternatively, elimination of such a sequence by substitutions removes an existing N-linked carbohydrate chain. Also provided is a rearrangement of N-linked carbohydrate chains, wherein one or more N-linked glycosylation sites (typically those that are naturally occurring) are eliminated and one or more new N-linked sites are created. Additional preferred antibody variants include cysteine variants, wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to human endothelin receptor, or to increase or decrease the affinity of the antibodies to human endothelin receptor described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically cannot substantially change the structural characteristics of the parent sequence (e.g., a replacement amino acid should not break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (Branden and Tooze, Eds., Garland Publishing, New York, N.Y. (1991)); and Thornton et al., 1991, *Nature* 354:105, each of which is incorporated herein by reference.

In certain embodiments, antibodies of the invention can be chemically bonded with polymers, lipids, or other moieties.

The antigen binding agents can comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to present one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically, the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains can be used (see, e.g., Nygren and Uhlen, 1997, *Current Opinion in Structural Biology* 7:463-469).

Additionally, one skilled in the art will recognize that suitable binding agents include portions of these antibodies, such as one or more of heavy chain CDR1, CDR2, CDR3, light chain CDR1, CDR2 and CDR3 as specifically disclosed herein. At least one of the regions of heavy chain CDR1, CDR2, CDR3, CDR1, CDR2 and CDR3 can have at least one amino acid substitution, provided that the antibody retains the binding specificity of the non-substituted CDR. The non-CDR portion of the antibody can be a non-protein molecule, wherein the binding agent cross-blocks the binding of an antibody disclosed herein to human endothelin receptor and/or inhibits the activity of endothelin-1 signaling through the receptor. The non-CDR portion of the antibody can be a non-protein molecule in which the antibody exhibits a similar binding pattern to human endothelin receptor peptides in a competition binding assay as that exhibited by at least one of antibodies A1/A2, and/or neutralizes the activity of endothelin-1. The non-CDR portion of the antibody can be composed of amino acids, wherein the antibody is a recombinant binding protein or a synthetic peptide, and the recombinant binding protein cross-blocks the binding of an antibody disclosed herein to human $ET_AR$ and/or neutralizes endothelin-1 activity in vitro or in vivo. The non-CDR portion of the antibody can be composed of amino acids, wherein the antibody is a recombinant antibody, and the recombinant antibody exhibits a similar binding pattern to human $ET_AR$ peptides in a competition binding assay as exhibited by at least one of the antibodies A1/A2, and/or neutralizes endothelin-1 signaling.

Nucleic Acids

In one aspect, the present invention provides isolated nucleic acid molecules that encode the antibodies of the present invention. The nucleic acids comprise, for example, polynucleotides that encode all or part of an antibody, for example, one or both chains of an antibody of the invention, or a fragment, derivative, mutein, or variant thereof; polynucleotides sufficient for use as hybridization probes; PCR primers or sequencing primers for identifying, analyzing, mutating or amplifying a polynucleotide encoding a polypeptide; anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) can be isolated from B-cells of mice that have been immunized with $ET_AR$ antigen. The nucleic acid can be isolated by conventional procedures such as polymerase chain reaction (PCR).

Nucleic acid sequences encoding the variable regions of the heavy and light chain variable regions are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antibody of the invention.

The invention further provides nucleic acids that hybridize to other nucleic acids (e.g., nucleic acids comprising a nucleotide sequence of any of A-1/A-2) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., Eds., John Wiley & Sons, Inc., sections 2.10 and 6.3-6.4), and can be readily determined by those having ordinary skill in the art based on, for example, the length and/or base composition of the DNA. Changes can be introduced by mutation into a nucleic acid, thereby leading to changes in the amino acid sequence of a polypeptide (e.g., an antibody) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. No matter how it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at nonessential amino acid residues. In one embodiment, nucleotide sequences provided herein for L1 to L2 and H1 to H2, or fragments, variants, or derivatives thereof, are mutated such that they encode amino acid sequences provided herein for L1 to L2 and H1 to H2, comprising one or more deletions or substitutions of amino acid residues to result in sequences bearing two or more different amino acid residues. In another embodiment, the mutagenesis inserts an amino acid adjacent to one or more amino acid residues shown herein for L1 to L2 and H1 to H2 to result in sequences with two or more different amino acid residues. Alternatively, one or more mutations can be introduced into a nucleic acid that selectively change the biological activity. (e.g., binding to $ET_AR$) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., an $ET_AR$ binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, *Trends Biochem. Sci.* 11:287, Maniatis et al., 1987, *Science* 236:1237, the disclosure of each of which is incorporated by reference herein in its entirety), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see Id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell or eukaryotic cell. Prokaryotic host cells include gram negative or gram positive organisms, for example, *E. coli* or *bacilli*. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, *Cytotechnology* 28:31) or CHO strain DXB-11, which is deficient in DHFR (see Urlaub et al., 1980, *Proc. Natl. Acad. Sci. USA* 77:4216-20). Additional CHO cell lines include CHO-K1 (ATCC # CCL-61), EM9 (ATCC # CRL-1861), and W20 (ATCC # CRL-1862). Additional host cells include the COS-7 line of monkey kidney cells (ATCC # CRL-1651) (see Gluzman et al., 1981, Cell 23:175), L cells, C127 cells, 3T3 cells (ATCC CCL-163), AM-1/D cells (described in U.S. Pat. No. 6,210,924), HeLa cells, BHK (ATCC CRL-10) cell lines, the CV1/EBNA cell line derived from the African green monkey kidney cell line CV1 (ATCC CCL-70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, N.Y., 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells can integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of a polypeptide, and the polypeptide recovered by conventional protein purification procedures. One such purification procedure is described in the Examples below. Polypeptides contemplated for use herein include substantially homogeneous recombinant mammalian anti-endothelin receptor antibody polypeptides substantially free of contaminating endogenous materials.

Activity of Antibodies

In one aspect, the present invention provides murine or humanized antibodies that specifically bind to a human endothelin receptor. Such antibodies include antagonizing or neutralizing antibodies capable of reducing or neutralizing endothelin-1 signaling. In one embodiment, the antibodies, such as the antibodies of the present invention have an $IC_{50}$ of 100 nM or less, in another embodiment, an $IC_{50}$ of 80 nM or less, in another embodiment, 60 nM or less. In another embodiment, the antibodies such as the murine antibodies of the present invention are capable of specifically binding to a human endothelin receptor, and have an $IC_{50}$ that is substantially similar to that of a reference antibody. In another embodiment, the antibodies have a Kb (or Kd) as measured by the assay described in the examples below (or similar assays), that is substantially similar to that of a reference antibody. As used herein, the term "substantially similar" means comparable to, or about 100%, 99%, 98%, 97%, 95%, 90%, 85%, 80%, 75%, 70%, 65% or 50% identical to the $IC_{50}$ or Kb (or Kd) value of a reference antibody. Reference antibodies include, for example, antibodies having a heavy chain and light chain combination L1H1, L2H2. In one embodiment, the reference antibodies include A-1. In another embodiment, the antibodies such as the murine antibodies or humanized antibodies of the present invention are capable of specifically binding to a human endothelin receptor, and lowering pulmonary arterial pressure in an animal model. In one embodiment, the pulmonary arterial pressure is lowered by 2% compared with untreated animals, in another embodiment, the pulmonary arterial pressure is lowered by 5% compared with untreated animals, in another embodiment, the pulmonary arterial pressure is lowered by 10% compared to untreated animal, in another embodiment, the pulmonary arterial pressure is lowered by 15%, in another embodiment, by 20%, in another embodiment, by 25% or more. The amount of reduction of pulmonary arterial pressure is controlled by dosage. A therapeutically effective dosage is the dosage required to reduce pulmonary arterial pressure into the normal range for the animal or human patient.

Indications

Pulmonary arterial hypertension (PAH) is caused by various reasons and characteristic with a group of pathological or physiological symptoms. Under a resting state, PAH patients have a mean pulmonary arterial pressure (mPAP) higher than or equal to 25 mmHg. PAH results in alteration in the blood circulation hemodynamics of the lung vasculature and eventually leads to right heart failure, even death. PAH is a fairly common disease in China and the rates of disability and fatality among patients are fairly high. It is one of the most devastating diseases with a huge negative impact both on the patient's well beings and life, and it burdens the society with towering medical care and expense.

The severity of PAH depends on relevant cardiac deformities. Common congenital heart diseases that can cause secondary PAH include: aortic stenosis, aortopulmonary window, atrial septal defect, complete atrioventricular septal defect, arterial coarctation, dilated cardiomyopathy, right ventricular double outlet, hypertrophic cardiomyopathy, mitral stenosis, patent ductus arteriosus, persistent arterial trunk, ventricular septal defect. Pulmonary arterial hypertension mainly involves the pulmonary artery and right heart with right ventricular hypertrophy and right atrial dilatation. It can result in pulmonary artery dilatation and peripheral pulmonary artery sparse, proliferation of pulmonary arterial endothelial cells, hypertrophy of smooth muscle cells, thickening of vascular intimal fibrosis, mesenteric hypertrophy, stenosis, occlusion, distortion and plexiform changes. Intimal fibroelastosis and in-situ thrombosis in pulmonary small veins can occur as well.

The present invention provides antibodies that can specifically bind to human $ET_4R$, reduce the pulmonary arterial pressure in different animal models and significantly ameliorate their symptoms of PAH.

Methods of Treatment

In another aspect, provided herein is a method of treating a subject, comprising administering a therapeutically effective amount of an antibody of the present invention. In one embodiment, the antibody is a murine antibody or a humanized antibody. As used herein, the term "subject" refers to a mammal, including humans, and is used interchangeably with the term "patient." The murine antibody or humanized antibody, can be used to treat, control or prevent a disorder or condition characterized by an excessive level of pulmonary hypertension in a subject. The term "treatment" encompasses alleviation or prevention of at least one symptom or other aspect of a disorder, or reduction of disease severity, and the like. An antibody of the present invention needs not to provide a complete cure, or to eradicate every symptom or manifestation of a disease, to be an effective therapeutic agent. As is recognized in the pertinent field, therapeutic agents can reduce the severity of a given disease state, but need not to abolish every manifestation of the disease to be effective. Similarly, a prophylactic agent needs not to prevent the onset of a condition completely in order to be effective. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an antibody in an amount and for a time sufficient to induce a sustained improvement over baseline of an indicator that reflects the severity of a particular disorder.

As is understood in the pertinent field, a pharmaceutical composition comprising an antibody of the invention is administered to a subject in a manner appropriate to the indication and the composition. In one embodiment, a pharmaceutical composition comprises a murine antibody or a humanized antibody of the present invention. A pharmaceutical compositions can be administered by any suitable technique, including, but not limited to, parenterally, topically, or by inhalation. If injected, the pharmaceutical composition can be administered, for example, via an intraarticular, intravenous, intramuscular, intralesional, intraperitoneal or subcutaneous route, by bolus injection or continuous infusion. It is considered, for example, localized administration at the disease or injury site, such as transdermal administration and sustained release of an implant. Delivery by inhalation includes, for example, nasal or oral inhalation, use of a nebulizer, inhalation of an antibody in aerosol form, and the like. Other alternatives include oral preparations, including pills, syrups, or lozenges.

Advantageously, the antibodies of the invention, are administered in a composition comprising one or more additional components such as a physiologically acceptable carrier, excipient or diluent. The composition additionally comprises one or more physiologically active agents as described below. In many particular embodiments, the composition comprises one, two, three, four, five, or six physiologically active agents in addition to one or more antibodies (e.g., murine antibodies or humanized antibodies) of the present invention.

In one embodiment, the pharmaceutical composition comprises a murine antibody or humanized antibody of the invention together with one or more substances selected from the group consisting of a buffer suitable for the antibody at a suitable pH, an antioxidant such as ascorbic acid, a low molecular weight polypeptide (such as those having fewer than 10 amino acids), a protein, an amino acid, a carbohydrate such as dextrin, a chelating agent such as EDTA, glutathione, a stabilizer, and an excipient. In accordance with appropriate industry standards, preservatives can also be added. The composition can be formulated as a lyophilizate using appropriate excipient solutions as diluents. Suitable components are nontoxic to recipients at the dosages and concentrations employed. Further examples of components that can be employed in pharmaceutical formulations are presented in Remington's Pharmaceutical Sciences, 16th Ed. (1980) and 20th Ed. (2000). Mack Publishing Company kits for use by medical practitioners are provided, including one or more antibodies of the invention and a label or other instructions for use in treating any of the conditions discussed herein. In one embodiment, the kit includes a sterile preparation of one or more human antibodies, which can be in the form of a composition as disclosed above, and can be in one or more vials.

Dosages and the frequency of administration can vary according to such factors as the route of administration, the particular antibodies employed, the nature and severity of the disease to be treated, whether the condition is acute or chronic, and the size and general condition of the subject. Appropriate dosages can be determined by procedures known in the pertinent art, e.g., in clinical trials that can involve dose escalation studies.

An antibody of the invention can be administered, for example, once or more than once, e.g., at regular intervals over a period of time. In particular embodiments, a murine antibody or humanized antibody is administered over a period of at least once a month or more, e.g., for one, two, or three months or even indefinitely. For treating chronic conditions, long-term treatment is generally most effective. However, for treating acute conditions, administration for shorter periods, e.g., from one to six weeks, can be sufficient. In general, the humanized antibody is administered until the patient manifests a medically relevant degree of improvement over baseline for the chosen indicator or indicators.

One example of therapeutic regimens provided herein comprise subcutaneous injection of an antibody once a week, at an appropriate dosage, to treat a condition in which pulmonary arterial pressure levels play a role. Weekly or monthly administration of antibody would be continued until a desired result is achieved, e.g., the subject's symptoms subside. Treatment can resume as needed, or, alternatively, maintenance doses can be administered.

A subject's levels of pulmonary arterial pressure can be monitored before, during and/or after treatment with an antibody such as a humanized antibody, to detect changes, if any, in their levels. For some disorders, the incidence of elevated pulmonary arterial pressure can vary according to such factors as the stage of the disease. Known techniques can be employed for measuring pulmonary arterial pressure levels.

Particular embodiments of methods and compositions of the invention involve the use of an antibody and one or more $ET_AR$ antagonists for example, two or more antibodies of the invention, or an antibody of the invention and one or more other $ET_AR$ antagonists. In further embodiments, the antibody is administered alone or in combination with other agents useful for treating the condition with which the patient is afflicted. Examples of such agents include both proteinaceous and non-proteinaceous drugs. When multiple therapeutics are co-administered, dosages can be adjusted accordingly, as is recognized in the pertinent art. "Co-administration" and combination therapy are not limited to simultaneous administration, but also include treatment regimens in which an antibody is administered at least once during a course of treatment that involves administering at least one other therapeutic agent to the patient.

In another aspect, the present invention provides a method of preparing medicine for the treatment of pulmonary arterial hypertension and related disorders, including a mixture of an antibody of the present invention and pharmaceutically acceptable excipients. The pharmaceutical preparation method is as described above.

EXAMPLES

1. Construction of a Stable Antigen Cell Line for Immunization

CHO-DHFR-cells were seeded into a 6-well plate. After 24 h culture, the cells were transfected with a pIRES plasmid (Clontech, commercial) modified to carry $hET_AR$ gene (see SEQ ID NO: 1 for the nucleotide sequence, and SEQ ID NO: 2 for the amino acid sequence). The medium was changed before transfection and the transfection was carried out by following the transfection conditions recommended by Invitrogen for Lipofectamine 2000. Forty eight hours after transfection, the medium was replaced with a complete medium containing 10 nM MTX (methotrexate). The medium was changed every 3 days for about two weeks until stable clones appeared. The dispersed cell colonies were detached from the plate and collected. After cells grew to about 50% confluence, the concentration of MTX was graduately increased for pressure selection up to 10 µM. The constructed stable cell lines were analyzed by FACS using a polyclonal antibody (Abcam) against $hET_AR$ to identify cell clones after pressure selection. A large amount of $hET_AR$ expression were detected on the selected CHO-DHFR-$hET_AR$ cell membranes. Finally through subcloning, six high-$ET_AR$ expression and stable cell lines were identified and obtained.

2. Preparation of Antibodies

An emulsion of the CHO-DHFR-$hET_AR$ whole cells and Freund's adjuvant was injected subcutaneously into BALB/c mice (6-8 weeks) at $2 \times 10^6$ cells/mouse. After 2 weeks, the mice were boosted with incomplete Freund's adjuvant emulsified immunogen and then boosted once every week. After immunization for 6 times in total, blood samples were collected from the clipped tail ends and centrifuged to collect the serum. The serum was analyzed for serum titers by FACS. After the acceptable antibody titers were achieved, the mice were sacrificed and their spleen cells were harvested under aseptic conditions. SP2/0 cells were collected at the logarithmic phase of growth with 3 min centrifugation at 2,000 rpm. The cell pellets were resuspended with serum-free culture medium, then centrifuged, resuspended for a second time and counted. Spleen cells and SP2/0 cells were mixed at ratio of SP2/0 cells:spleen cells≥1:1, followed by 3 rounds of washing-centrifugation. After the pellets from the last centrifugation were detached, 1 mL of pre-warmed PEG-1350 was added dropwise (finished in 30 s), after pipette-mixing for 1 min, 30 mL of the pre-warmed serum-free medium (Invitrogen) was added slowly to terminate the PEG fusion. After 5 min centrifugation at 1,500 rpm, the cell pellets were resuspended in the fusion culture medium. Spleen cells (20,000) and feeder layer cells (5,000) in 100 µL were plated into each well of 96-well plates. Fused hybridoma cells and feeder layer cells were co-cultured in 96-well plates with HAT (sarcine, amethopterin and thymidine) selection to get rid of the non-fused cells. After 10 days, the supernatants of the hybridoma cells in the culture plates were collected for ELISA analysis.

3. ELISA Screening of Whole Cells

CHO-DHFR-hET$_4$R cells over-expressing hET$_4$R and CHO-DHFR-cells not expressing hET$_4$R were separately transferred into a 96-well plate and allowed to grow to 90% confluent. The supernatant of the culture medium was removed and attached cells were washed twice with PBS, then 100 μL, 100% methanol was added to fix the cells for 10 min at 4° C. Then 100 μL freshly made 0.6% H$_2$O$_2$-PBS was added, and after incubation at room temperature for 20 min, the cells were washed twice with PBS. After blocked with PBS-1% BSA solution, the hybridoma supernatant was added and incubated for 90 min at 4° C. After several washes, 100 μL of the secondary antibody GxM-HRP-Fc (Sigma-Aldrich) was added into each well and incubated at 37° C. for 0.5 h. After five washings, 100 μL of TMB chromogenic substrate was added into each well and incubated at 37° C. for 15 min, and then 2M H$_2$SO$_4$ was added to terminate, read for OD$_{450}$ values. The positive control was the mouse serum after immunization; the negative control was the cell culture supernatant. As shown in FIG. 1, after initial analysis by ELISA, several hybridoma clones secreting anti-hET$_4$R antibodies were selected, and the stable secretory cell lines against hET$_4$R were obtained after cell cloning. Lastly, antibody supernatant secreted by hybridoma was verified by FACS analysis.

4. Cloning and Subcloning of Antibody Genes

Hybridoma cells secreting antibodies were collected. Hybridoma mRNA was extracted according to the manufacturer protocol of QIAGEN mRNA extraction kit. Then the extracted mRNA was transcribed reversely into cDNA. The reverse transcription primers were specific primers for the light and heavy chain constant regions of a mouse, with the heavy chain reverse transcription primer being (5'-TTTGGRGGGAAGATGAAGAC-3') (SEQ ID NO: 199), the light chain reverse transcription primers being (5'-TTAACACTCTCCCCTGTTGAA-3') (SEQ ID NO: 200) and (5'-TTAACACTCATTCCTGTTGAA-3') (SEQ ID NO: 201). RT-PCR reaction conditions were as following: 25° C. for 5 min, 50° C. for 60 min, and 70° C. for 15 min. Reversely transcribed cDNA was diluted with 0.1 mM TE to 500 μL, added into the ultrafiltration centrifuge tube (Amicon Ultra-0.5) and centrifuged at 2,000 g for 10 min. The filtrate was removed, 500 μL of 0.1 mM TE were added and centrifuged at 2,000 g for 10 min. The filtrate was removed and the preparation tube was placed in inversion to the new centrifugal tube, and centrifuged at 2,000 g for 10 min to obtain the purified cDNA. Purified cDNA (10 μL) was taken as a template, followed by addition of 4 μL 5× tailing buffer (Promega), 4 μL dATP (1 mM) and 10 U terminal transferase (Promega), mixing uniformly, and incubation at 37° C. for 5 min and then at 65° C. for 5 min. The PolyA tail cDNA was used as a template and PCR was performed to amplify light and heavy chain variable region genes of antibodies. Upstream primers were all oligodT, with heavy chain downstream primers being (5'-TGGACAGGGATCCAGAGTTCC-3') (SEQ ID NO: 202) and (5'-TGGACAGGGCTCCATAGTTCC-3') (SEQ ID NO: 203), and light chain downstream primer being (5'-ACTCGTCCTTGGTCAACGTG-3') (SEQ ID NO: 204). The PCR reaction conditions were: 95° C. for 5 min; 95° C. for 30 s, 56° C. for 30 s, 72° C. for 1 min, 40 cycles; and 72° C. for 7 min. The PCR products were connected to the PMD 18-T vector (Takara Bio) for sequencing. The sequences of the antibody clones were listed in Table 2.

PCR primers were designed based on the DNA sequences of the antibodies, thus the complete light chain, heavy chain signal peptides and variable domains and mouse IgG1 constant region were ligated into expression vector pTM5.

5. Antibody Humanization and Optimization

First of all, the sequences of light and heavy chain variable regions of the screened mouse antibodies were aligned with the homologous antibodies, using NCBI online antibody variable region sequence alignment tool (Ig Blast) to search the germline gene sequences of a humanized antibody (Ig Germline Gene sequence) homologous to the selected antibodies variable region sequence for humanization, and the humanized gene sequence with highest homology except CDR sequences was used as a template for CDR grafting to obtain humanized antibody variable region sequences and to synthesize humanized antibody light and heavy chain genes through a CRO. According to the sequences, PCR primers were designed and appropriate restriction enzyme sites were introduced at the 5' ends and 3' ends. By PCR, the humanized antibody variable regions were amplified and then combined with the human IgG2 or IgG4 constant region sequence to obtain whole recombinant humanized antibody sequences. The expression of the recombinant antibodies was achieved according to step 7, and their affinities to ET$_4$R was analyzed by FACS as described in step 9. The best humanized antibody candidate retaining affinity to ET$_4$R was selected from the group, and its variable region sequence was further improved by site-specific mutagenesis for improved affinity to ET$_4$R.

6. Subcloning of Genes of a Humanized Anti-hET$_4$R Antibody

The heavy and light chain variable region gene sequences of an optimized humanized antibody were synthesized by Genscript Biotechnology CO., LTD by introducing two restriction sites of NheI at the 5'-end and SalI at the 3'-end. The whole heavy chain variable region was ligated with a heavy chain constant region in an expression vector of pTM5. Similarly, by introducing NheI at the 5'-end and BsiwI at the 3'-end, the light chain variable region was ligated with a light chain constant region in the expression vector of pTM5.

7. Transient Expression of Anti-$ET_A$R Antibodies

A suspension of a HEK293 or CHO expressing cell line ($5\times10^5$/mL) was inoculated to a shaker flask. After 24 h rotation at 37° C., the cell density reached $1\times10^6$/mL and were ready for transfection. Polyethylenimine (PEI) was used as a transfection reagent with an optimal mixing ratio of 3:1 for PEI to DNA (DNA amount, 0.5 μg/L$\times10^6$ cells; the ratio of the antibody light chain DNA and antibody heavy chain DNA, 3:2). A mixture of both was added into the cell culture after 15 min incubation. The cells after treated with the PEI/DNA mixture were rotated for more than 24 h at 37° C. and 5% $CO_2$. Then 0.5% of tryptone was added into the cell culture as a supplement required by expression, and after the completion of expression (more than 96 h), the cell supernatant was collected for the antibody purification and separation.

8. Purification and Preparation of Antibody

Cells and cellular debris were removed from the culture after centrifugation (8000 rpm, 15 min), and the supernatant was filtered through 0.45 μm filter for purification. The purification process was done through chromatography. First, the supernatant was passed through a G protein coupled affinity chromatography column, and antibodies bound to the G proteins remained in the column. The antibodies were eluted from the chromatography column using an eluent with pH of 3.0 or less. The low pH eluent was neutralized immediately with 1M Tris-HCl to keep the antibodies from denaturation and loss of activity. The antibody solution was then dialyzed over 16 h into a PBS buffer.

9. FACS Analysis of a Functional Antibody

PBS containing 10 mM EDTA was used to detach and collect $10^5$ CHO-DHFR-hET$_A$R cells into a 1.5 mL EP tube. The supernatant was removed after centrifugation and the negative control sample was resuspended with a loading buffer (PBS, 2% FBS). For the positive control, 200 µL antibody supernatant was added to resuspension cells and incubation at room temperature; the cells were then centrifuged at 1500 rpm to remove the supernatant, washed with a FACS loading buffer and centrifuged again. The cells were resuspended with addition (200 µL/well) of a FITC labeled goat anti-mouse fluorescent antibody at 1:50 dilution (BD Pharmingen) and incubated at room temperature for 30 min in the dark. Supernatant was removed after centrifugation, cells were washed with FACS loading buffer, centrifuged again and resuspended with the loading buffer for analysis. As shown in FIG. 2, the recombinant antibody supernatant and CHO-DHFR-hET$_A$R cells had specific binding: gray peak and dotted line peak were negative controls; the solid line peak, corresponding to the antibody supernatant, moved to the right significantly.

10. Calcium Influx Assay for a Functional Antibody

Figure 3:
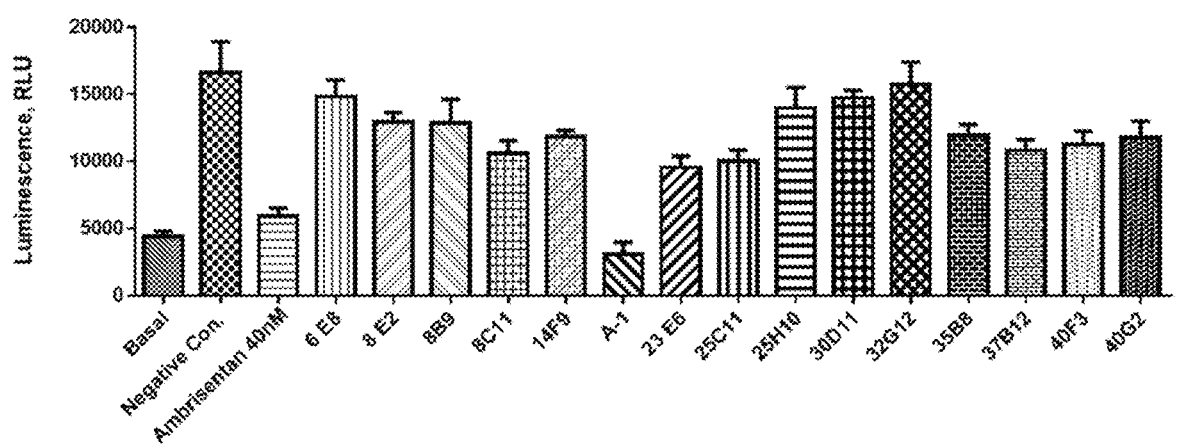
FIG. 3 shows the inhibitory effects of the supernatants of hybridomas on cellular $ET_AR$-mediated $Ca^{2+}$ changes as determined using a calcium flux assay.
Figure 4:
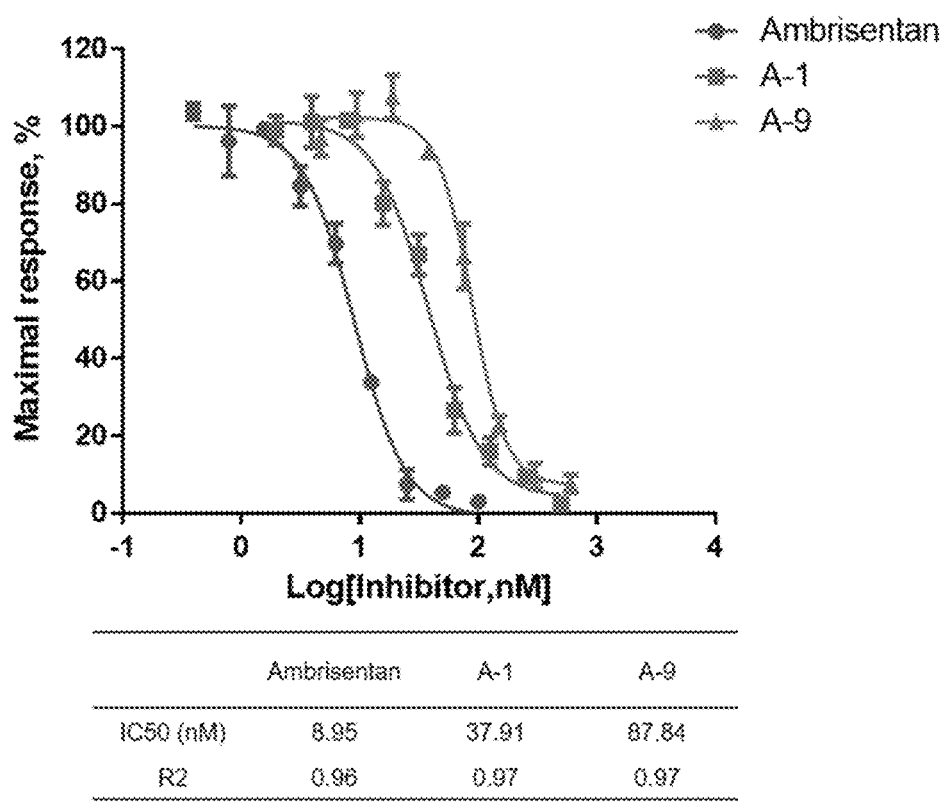
FIG. 4 shows the dose responses of recombinant anti-$ET_AR$ antibodies on the inhibition of human $ET_AR$ as determined using a calcium flux assay ($IC_{50}$=37.91 nM, $R^2$=0.97) (A-1); ($IC_{50}$=87.84 nM, $R^2$=0.97) (A-9).

CHO-DHFR cells co-expressing hET$_A$R-Aequorin were seeded into a 96-well cell culture plate with 25000 cells per well and cultured at 37° C. overnight. The next day the culture supernatant was removed. Coelenterazine (50 µL) (Promega) was added in the dark and incubated at 37° C. for 2 h, and then 50 µL of a hybridoma supernatant or a purified antibody were added and incubated at 37° C. for 30 min. After the incubation, 50 µL endothelin 1 was added and the changes of calcium influx within 40 s were recorded by a SpectraMax L microplate reader (Molecular Devices). As shown in FIG. 3, different hybridoma supernatants inhibited the calcium influx mediated through hET$_A$R differently, and A-1 antibody significantly inhibited the calcium influx mediated through hET$_A$R. As shown in FIG. 4, the recombinant anti-hET$_A$R functional antibody significantly inhibited calcium influx mediated through hET$_A$R, increasingly inhibitory with an increase in the antibody concentration.

Figure 5:
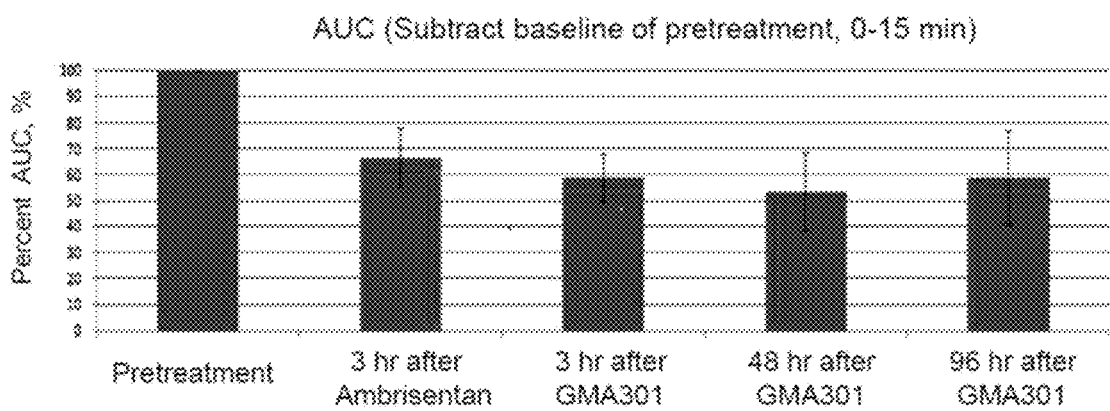
FIG. 5 shows the in vivo activity of the recombinant anti-$ET_AR$ (A-1) in a hypoxia-induced PAH monkey model. A1 was found to be able to reduce the systolic arterial pressure significantly, and also to be effective throughout the 96-hr window as measured by area under the curve of systolic arterial pressure versus time.

11. Establishment of Hypoxia-Induced PAH Cynomolgus Model to Study the In Vivo Activity of an Antibody The acute hypoxia-induced pulmonary arterial hypertension (PAH) model of cynomolgus was codeveloped with Crown Bioscience Inc. (Taicang), and the efficacy of A-1 antibody as a single intravenous injection was evaluated in this PAH model. All animals were fasted overnight and weighed, and then received a single intravenous injection of 10 mg/kg of A-1 antibody. Three hours later, the animals were anesthetized. The tricuspid regurgitation velocity by Doppler color echocardiography along with heart rate and oxygen saturation were monitored simultaneously. The baseline was obtained and the induction of 12% hypoxia was followed and at the same time the tricuspid regurgitation velocity was measured; Analysis was made to determine if the antibody would improve hypoxia-induced pulmonary arterial pressure under 12% hypoxia. After 48 h of administration, the tests were performed again. The animals were anesthetized, the tricuspid regurgitation velocity by Doppler color echocardiography along with heart rate and oxygen saturation were monitored simultaneously. The baseline was obtained and the induction of 12% hypoxia was followed and at the same time the tricuspid regurgitation velocity was measured. Analysis was made to determine if the antibody would still improve hypoxia-induced pulmonary arterial pressure. If the efficacy maintained after 48 h, 96 h later, hypoxia induction experiment was performed again. As shown in FIG. 5, the area under the curve of pulmonary artery systolic pressure versus time was calculated, and by comparing the area under the curve, it was found that A-1 maintained the efficacy of reducing pulmonary artery pressure within 96 h.

The examples set forth above are to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims.

What is claimed is:

1. An antibody that specifically binds to a human endothelin receptor comprising:
   light chain CDR1 amino acid sequence: SEQ ID NO: 24;
   light chain CDR2 amino acid sequence: SEQ ID NO: 44;
   light chain CDR3 amino acid sequence: SEQ ID NO: 62;
   heavy chain CDR1 amino acid sequence: SEQ ID NO: 84;
   heavy chain CDR2 amino acid sequence: SEQ ID NO: 108; and
   heavy chain CDR3 amino acid sequence: SEQ ID NO: 130.

2. The antibody of claim 1, comprising
   light chain variable domain amino acid sequence: SEQ ID NO: 154; and
   heavy chain variable domain amino acid sequence: SEQ ID NO: 182.

3. The antibody of claim 2, further comprising an amino acid sequence selected from:
   (a) light chain constant region amino acid sequence: SEQ ID NO: 194;
   (b) light chain constant region amino acid sequence: SEQ ID NO: 196;
   (c) heavy chain constant region amino acid sequence: SEQ ID NO: 198;
   (d) light chain constant region amino acid sequence: SEQ ID NO: 194 and heavy chain constant region amino acid sequence: SEQ ID NO: 198; and
   (e) light chain constant region amino acid sequence: SEQ ID NO: 196 and heavy chain constant region amino acid sequence: SEQ ID NO: 198.

4. The antibody of claim 1, wherein the antibody comprises:
   a light chain variable domain amino acid sequence encoded by a polynucleotide sequence that is at least 80% identical to SEQ ID NO: 153; and a heavy chain variable domain amino acid sequence encoded by a polynucleotide sequence that is at least 80% identical to SEQ ID NO: 181.

5. The antibody of claim 1, wherein the antibody is a murine antibody, a human antibody or a humanized antibody.

6. A pharmaceutical composition comprising the antibody of claim claim 1 and a pharmaceutically acceptable excipient.

7. The pharmaceutical composition of claim 6, wherein the antibody is a murine antibody or a humanized antibody.

8. A kit of treating pulmonary arterial hypertension, a disease associated with pulmonary arterial hypertension, and a reproductive organ cancer, comprising the pharmaceutical composition of claim 6 and a label or instructions for use.

9. A method of treating pulmonary arterial hypertension in a subject in need thereof, comprising administering to the subject a therapeutically effective amount of the pharmaceutical composition of claim 6.

* * * * *